US010722541B2

(12) United States Patent
Aberman et al.

(10) Patent No.: US 10,722,541 B2
(45) Date of Patent: Jul. 28, 2020

(54) METHODS FOR TREATING RADIATION OR CHEMICAL INJURY

(71) Applicant: PLURISTEM LTD., Haifa (IL)

(72) Inventors: Zami Aberman, Tel-Mond (IL); Raphael Gorodetsky, Jerusalem (IL)

(73) Assignee: PLURISTEM LTD., Hiafa (IL)

( * ) Notice: Subject to any disclaimer, the term of this patent is extended or adjusted under 35 U.S.C. 154(b) by 0 days.

(21) Appl. No.: 15/643,144

(22) Filed: Jul. 6, 2017

(65) Prior Publication Data

US 2017/0368106 A1 Dec. 28, 2017

Related U.S. Application Data

(63) Continuation of application No. 14/006,580, filed as application No. PCT/IB2012/000664 on Mar. 22, 2012, now abandoned, which is a continuation-in-part of application No. 13/161,334, filed on Jun. 15, 2011, now abandoned, which is a continuation-in-part of application No. 13/069,130, filed on Mar. 22, 2011, now abandoned.

(60) Provisional application No. 61/595,485, filed on Feb. 6, 2012, provisional application No. 61/497,400, filed on Jun. 15, 2011.

(51) Int. Cl.
| | | |
|---|---|---|
| *A01N 63/00* | (2020.01) | |
| *A01N 65/00* | (2009.01) | |
| *A61K 35/50* | (2015.01) | |
| *A61K 35/28* | (2015.01) | |
| *A61K 35/35* | (2015.01) | |
| *C12N 5/073* | (2010.01) | |
| *C12N 5/0775* | (2010.01) | |
| *A61K 35/12* | (2015.01) | |

(52) U.S. Cl.
CPC .............. *A61K 35/50* (2013.01); *A61K 35/28* (2013.01); *A61K 35/35* (2013.01); *C12N 5/0605* (2013.01); *C12N 5/0663* (2013.01); *C12N 5/0667* (2013.01); *C12N 5/0668* (2013.01); *A61K 2035/124* (2013.01); *C12N 2513/00* (2013.01); *C12N 2531/00* (2013.01)

(58) Field of Classification Search
CPC ...................................................... A61K 35/50
See application file for complete search history.

(56) References Cited

U.S. PATENT DOCUMENTS

| | | | |
|---|---|---|---|
| 4,963,489 A | 10/1990 | Naughton et al. | |
| 5,266,476 A | 11/1993 | Sussman et al. | |
| 5,962,325 A | 10/1999 | Naughton et al. | |
| 6,291,240 B1 | 9/2001 | Mansbridge et al. | |
| 6,355,239 B1 | 3/2002 | Bruder et al. | |
| 6,875,605 B1 | 4/2005 | Ma | |
| 6,911,201 B1 | 6/2005 | Merchav et al. | |
| 7,045,148 B2 | 5/2006 | Hariri | |
| 7,255,879 B2 | 8/2007 | Hariri | |
| 7,311,904 B2 | 12/2007 | Hariri | |
| 7,311,905 B2 | 12/2007 | Hariri | |
| 7,468,276 B2 | 12/2008 | Hariri | |
| 7,498,171 B2 | 3/2009 | Hariri et al. | |
| 7,534,609 B2 | 5/2009 | Merchav et al. | |
| 7,638,141 B2 | 12/2009 | Hariri | |
| 7,678,573 B2 | 3/2010 | Merchav et al. | |
| 7,790,456 B2 | 9/2010 | Terstegge et al. | |
| 8,524,496 B2 | 9/2013 | Meiron et al. | |
| 8,529,888 B2 | 9/2013 | Meiron et al. | |
| 9,096,827 B2 | 8/2015 | Meiron et al. | |
| 9,512,393 B2 | 12/2016 | Kasuto et al. | |
| 2002/0045260 A1 | 4/2002 | Hung et al. | |
| 2002/0058025 A1 | 5/2002 | Prockop et al. | |
| 2002/0076400 A1 | 6/2002 | Katz et al. | |
| 2002/0160510 A1 | 10/2002 | Hariri | |
| 2003/0032179 A1 | 2/2003 | Hariri | |
| 2003/0161817 A1 | 8/2003 | Young et al. | |
| 2003/0235563 A1 | 12/2003 | Strom et al. | |
| 2004/0005300 A1 | 1/2004 | Ildstad | |
| 2004/0023370 A1 | 2/2004 | Yu et al. | |
| 2004/0258670 A1 | 12/2004 | Laughlin et al. | |
| 2005/0058631 A1 | 3/2005 | Kihm et al. | |
| 2005/0176143 A1 | 8/2005 | Merchav et al. | |
| 2005/0181504 A1 | 8/2005 | Merchav et al. | |
| 2005/0265980 A1 | 12/2005 | Chen et al. | |
| 2007/0253931 A1 | 11/2007 | Varney et al. | |
| 2007/0275362 A1 | 11/2007 | Edinger et al. | |
| 2009/0004738 A1 | 1/2009 | Merchav et al. | |
| 2010/0209403 A1 | 8/2010 | Meiron et al. | |
| 2011/0129447 A1 | 6/2011 | Meretzki et al. | |
| 2011/0129486 A1 | 6/2011 | Meiron | |

(Continued)

FOREIGN PATENT DOCUMENTS

| | | |
|---|---|---|
| EP | 1845154 A1 | 10/2007 |
| JP | 5733894 B2 | 1/2009 |

(Continued)

OTHER PUBLICATIONS

Francois Moria et al. Mesenchymal Stromal Cells Accelerate Hematopoietic Reconstitution and Mediate an IL6-Dependent Regeneration of the Intestinal Epithelium of Lethally Irradiated Mice. Blood 2010 116:3846.

Barlow et al. "Comparison of Human Placenta- and Bone Marrow-Derived Multipotent Mesenchymal Stem Cells", Stem Cells and Development, XP002563129, 17(6): 1095-1107, Dec. 2008. p. 1096-1100, Fig.4.

Brooke et al. "Therapeutic Applications of Mesenchymal Stromal Cells", Seminars in Cell & Developmental Biology, XP022372977, 18(6): 846-858, Dec. 1, 2007.

Fibbe et al. "Mesenchymal Stem Cells and Hematopoietic Stem Cell; Transplantation", Annals of the New York Academy of Sciences, 996: 235-244,; 2003.

(Continued)

Primary Examiner — Valarie E Bertoglio
(74) Attorney, Agent, or Firm — Lando & Anastasi, LLP

(57) ABSTRACT

Methods for treating radiation or chemical injury are described that comprise administering to a subject a therapeutically effective amount of adherent stromal cells. Methods of preparing adherent stromal cells and pharmaceutical compositions comprising the cells are also described.

28 Claims, 38 Drawing Sheets

(56) References Cited

U.S. PATENT DOCUMENTS

| | | |
|---|---|---|
| 2011/0171182 A1 | 7/2011 | Abelman |
| 2011/0256108 A1 | 10/2011 | Meiron et al. |
| 2011/0256159 A1 | 10/2011 | Meiron et al. |
| 2011/0256160 A1 | 10/2011 | Meiron et al. |
| 2011/0293583 A1 | 12/2011 | Aberman |
| 2012/0122220 A1 | 5/2012 | Merchav et al. |
| 2013/0004465 A1 | 1/2013 | Aberman |
| 2013/0039892 A1 | 2/2013 | Aberman |
| 2013/0259843 A1 | 10/2013 | Duda et al. |
| 2013/0323213 A1 | 12/2013 | Meiron et al. |
| 2013/0337558 A1 | 12/2013 | Meiron et al. |
| 2014/0030805 A1 | 1/2014 | Kasuto et al. |
| 2014/0242039 A1 | 8/2014 | Meiron et al. |
| 2015/0125138 A1 | 5/2015 | Karnieli et al. |
| 2015/0216907 A1 | 8/2015 | Chajut et al. |
| 2015/0232797 A1 | 8/2015 | Kasuto et al. |
| 2016/0022738 A1 | 1/2016 | Meretski et al. |
| 2016/0058799 A1 | 3/2016 | Aberman |
| 2018/0008649 A1 | 1/2018 | Aberman et al. |

FOREIGN PATENT DOCUMENTS

| | | |
|---|---|---|
| JP | 2009/531059 A | 9/2009 |
| WO | 2002-064755 A2 | 8/2002 |
| WO | 2003/080801 A2 | 10/2003 |
| WO | 2003-105908 A2 | 12/2003 |
| WO | 2005/001076 A2 | 1/2005 |
| WO | 2006/027229 A1 | 3/2006 |
| WO | 2006/138552 A2 | 12/2006 |
| WO | 2007/108003 A2 | 9/2007 |
| WO | 2008/100498 A2 | 8/2008 |
| WO | 2009/037690 A1 | 3/2009 |
| WO | 2009/111030 A1 | 9/2009 |
| WO | 2010/033285 A2 | 3/2010 |
| WO | 2010/060031 A1 | 5/2010 |
| WO | 2011/132087 A1 | 10/2011 |
| WO | 2012/127320 A1 | 9/2012 |

OTHER PUBLICATIONS

Gimble et al., Differentiation potential of adipose derived adult stem (ADAS) cells. Curr Top Dev Biol. 2003;58:137-60.
Horwitz et al. "Clarification of the Nomenclature for MSC: The International Society for Cellular Therapy Position Statement," Cytotherapy, 7(5): 393-395, 2005.
Iwase et al "Comparison of Angiogenic Potency Between Mesenchymal Stem Cells and Mononuculear Cells in a Rat Model of Hindlimb Ischemia," Cardiovascular Research, 66: 543-551, 2005.
Koc et al., Rapid hematopoietic recovery after coinfusion of autologous-bood stem cells and culture-expanded marrow mesenchymal stem cells in advanced breast cancer patients receiving high-dose chemotherapy. J clin Oncol. Jan. 2000;18(2):307-16.
Lange et al., Radiation rescue: mesenchymal stromal cells protect from lethal irradiation. PLoS One. Jan. 5, 2011;6(1):e14486. doi: 10.1371/journal.pone.0014486.
Le Blanc et al. "HLA Expression and Immunologic Properties of Differentiated and Undifferentiated Mesenchymal Stem Cells", Experimental Hematology, 31: 890-896, 2003.
Le Blanc et al., Transplantation of mesenchymal stem cells to enhance engraftment of hematopoietic stem cells. Leukemia. Aug. 2007;21(8):1733-8. Epub May 31, 2007.
Li et al. "Mesenchymal Stem Cells Derived From Human Placenta Suppress Allogeneic Umbilical Cord Blood Lymphocyte Proliferation", Cell Research, XP009080356, 15(7): 539-547, Jul. 1, 2005. p. 541-542, Fig.2, Table 2.
Minguell et al "Mesenchymal Stem Cells", Minireview, Experimental and Biological Medicine, 226(6): 507-520, 2001.
Moon et al. "Human Adipose Tissue-Derived Mesenchymal Stem Cells Improve Postnatal Neovascularization in a Mouse Model of Hindlimb Ischemia", Cellular Physiology and Biochemistry, 17: 279-290, Mar. 2006.
Nakagami et al "Adipose Tissue-Derived Stromal Cells as a Novel Option for Regenerative Cell Therapy", Journal of Atherosclerosis and Thrombosis, 13(2): 77-81, Dec. 2005.
Parolini et al., Review: Preclinical studies on placenta-derived cells and amniotic membrane: an update. Placenta. Mar. 2011;32 Suppl 2:S186-95. doi: 10.1016/j.placenta.2010.12.016. Epub Jan. 19, 2011.
Pluristem "Pluristem Demonstrates the Potential of Its PLX Cells to Treat Crohn's Disease and Ulcerative Colitis", Pluristem Home Page, Press Releases, XP002553068, p. 1-2, May 28, 2008. Abstract.
Prather et al. "Placental-Derived and Expanded Mesenchymal Stromal Cells (PLX-I) to Enhance the Engraftment of Hematopoietic Stem Cells Derived From Umbilical Cord Blood", Expert Opinion on Biological Therapy, XP009128193, 8(8): 1241-1250, Aug. 2008.
Prather et al. "The Role of Placental-Derived Adherent Stromal Cell (PLX-PAD) in the Treatment of Critical Limb Ischemi", Cytotherapy, XP009127935, 11(4): 427-434, Jan. 1, 2009.
Prather, Pluristem Therapeutics, Inc. Regen Med. Jan. 2008;3(1):117-22.
Ramot et al. "Safety and Biodistribution Profile of Placental-Derived Mesenchymal Stromal Cells (PLX-PAD) Following Intramuscular Delivery", Toxicologic Pathology, XP009127728, 37(5): 606-616, Aug. 1, 2009.
Response dated May 4, 2010 to Search Report and the Written Opinion dated Dec. 8, 2009 From the Intellectual Property Office of Singapore Issued by the Danish Patent and Trademark Office Re.: Application No. 200807095-5.
Tyndall et al. "Multipotent Mesenchymal Stromal Cells for Autoimmune Diseases: Teaching New Dogs Old Tricks", Bone Marrow Transplantation, XP002553067, 43(11): 821-828, Jun. 1, 2009.
Ventura et al. "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, 282(19):14243-14252, May 2007.
Wulf et al. "Mesemgenic Progenitor Cells Derived From Human Placenta", Tissue Engineering, XP001206075, 10(7/8):1136-1147, Jul. 1, 2004. Table 1.
Yen et al. "Isolation of Multipotent Cells From Human Term Placenta", Stem Cells, 23: 3-9, 2005.
Zhang et al. "Human Placenta-Derived Mesenchymal Progenitor Cells Support Culture Expansion of Long-Term Culture-Initiating Cells From Cord Blood CD34+ Cells", Experimental Hematology, 32: 657-664, 2004.
Zhao et al. "Perfusion Bioreactor System for Human Mesenchymal Stem Cell Tissue Engineering: Dynamic Cell Seeding and Construct Development", Biotechnology and Bioengineering, XP002457538, 91(4): 482-493, Aug. 1, 2005.
Zhou et al."Therapeutic Neovascularization for Peripheral Arterial Diseases: Advances and Perspectives", Histology and Histopathology, XP009127650, 22(6): 677-686, Jun. 1, 2007. Abstract.
Zimmet et al. "Emerging Role for Bone Marrow Derived Mesenchymal Stem Cells in Myocardial Regenerative Therapy", Basic Research in Cardiology, 100(6): 471-481, 2005.
Aschan, Allogeneic haematopoietic stem cell transplantation: current status and future outlook. Br Med Bull. 2006;77-78:23-36. Epub Sep. 11, 2006.
Corell, HLA matching in unrelated stem cell transplantation: what to type for? Immunologia. 2002; 21(3):169-177.
Finke et al., Matched and mismatched allogeneic stem-cell transplantation from unrelated donors using combined graft-versus-host disease prophylaxis including rabbit anti-T lymphocyte globulin. K Clin Oncol. Feb. 1, 2003; 21(3):506-13.
Jessop et al., Preparation, preservation, recovery and use of irradiated feeder layers in cell culture research. TCA manual/ Tissue Culture Association, 1979; vol. 5(3):1137-1139.
Katz et al., Cell surface and transcriptional characterization of human adipose-derived adherent stromal (hADAS) cells. Stem Cells. Mar. 2005; 23(3):412-23.
Kern et al., Comparative analysis of mesenchymal stem cells from bone marrow, umbilical cord blood, or adipose tissue. Stem Cells May 2006; 24(5):1294-301. Epub Jan. 12, 2006.

(56) References Cited

OTHER PUBLICATIONS

Li et al., Effects of three-dimensional scaffolds on cell organization and tissue development. Biotech Bioprocess Eng. Oct. 2001; 6(5): 311-325.

Meinel et al., Bone tissue engineering using human mesenchymal stem cells: effects of scaffold material and medium folw. Ann Biomed Eng. Jan. 2004; 32(1):112-22.

Mizokami et al., Preferential expansion of human umbilical cord blood-derived CD34-positive cells on major histocompatibility complex-matched amnion-derived mesenchymal stem cells. Hematologica. May 2009;94(5):618-28. doi 10.3324/heamatol.2008.004705. Epub Mar. 31, 2009.

Portmann-Ianz et al., Placental mesenchymal stem cells as potential autologous graft for pre- and perinatal neuroregeneration. Am J Obstet Gtnecol. Mar. 2006; 194(3):664-73.

Wu et al., [Cultivation of human mesenchymal ctem cells on macroporous CultiSphere G microcarrieirs]. Zhonoggou Shi Yan Xue Za Zhi. J Exp Hem. Feb. 2003; 11(1):15-21. Chinese.

Zhang et al., Comparison of mesenchymal stem cells from human placenta and bone marrow. Chin Med J (Engl). Jun. 2004;117(6):882-7.

Hu wt al. "The radiation Projection and Therapy Effects of Mesenchymal Stem Cells in Mice with Acute Radiation Injury", British Journal of Radiology, XP55023063, 83(985): 52-58, Jan. 1, 2010.

Freshney et al. "Culture of Animal Cells: A Manual of Basic Technique and Specialized Applications", Sixth Edition. 11:163-186 2010.

Shabbir et al. "Heart Failure therapy mediated by the trophic activities of bone marrow mwswnchymal stem cells: a noninvasive thrapeutic regimen", American Journal of Phisiology, Heart and Circulatory Phsiology, Apr. 2009, 296(6), pp. 1-22.

Breitbach et al. "Potential risks of bone marrow cell transplantation into infarced hearts", Blood, Aug. 2007, vol. 110, No. 4, pp. 1362-1369.

Yoon et al., "Unexpected Severe calcification After Transplantation of Bone Marrow Cells in Acute Myocardinal Infarction", Circulation, 2004, vol. 109, pp. 3154-3157.

Salem et al. "Mesenchymal Stormal cells: Current Understanding and Clinical Status", Stem Cells, 2010, vol. 28, pp. 585-596.

Maitra et al., "Human mesenchymal stem cells support unrelated donor hematopoietic stem cells and suppress T-cell activation", Bone Marrow Transplantation, 2004, vol. 33, pp. 597-604.

Mourcin et al., "Mesenchymal Stem cells Support Expansion of in Vitro Irradiated CD34+ Cells in the Presence of SCF, FLT3 Ligand, TPO and IL3: Potential Application to Autologous Cells Therapy in accidental Irradiated Victims", Radiation Research, 2005, vol. 164 No. 1, pp. 1-9.

Bryan Leigh et al. "Stem Cell Factor Enhances the Survival of Murine Intestinal Stem Cells after Photon Irradiation". Radiation Research 142: 12-15 (1995).

Bhatt et al., "Hematopoietic Cell Transplantation for Myelodysplastic Syndromes," Journal of Oncology Practice (2016) vol. 12, Issue 9, pp. 786-792.

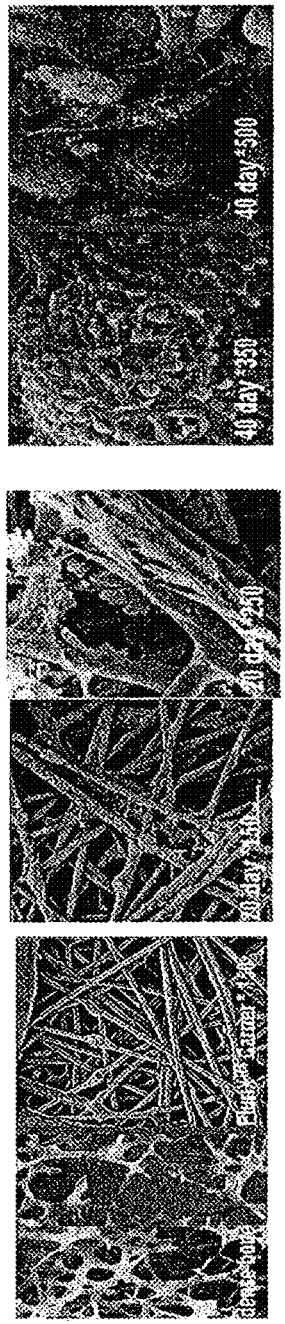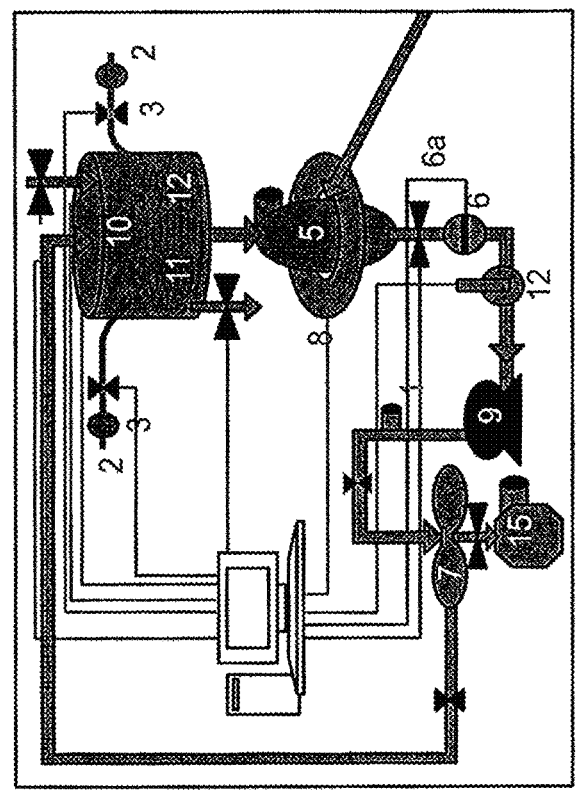
Fig. 1A  Fig. 1B  Fig. 1C  Fig. 1D  Fig. 1E  Fig. 1F  Fig. 1G

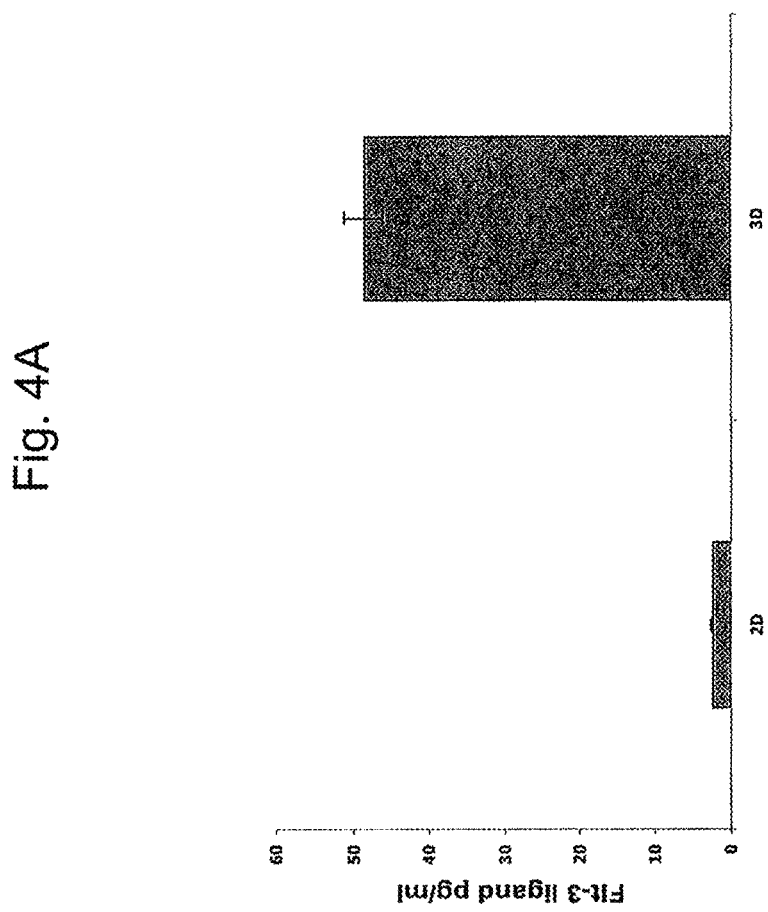

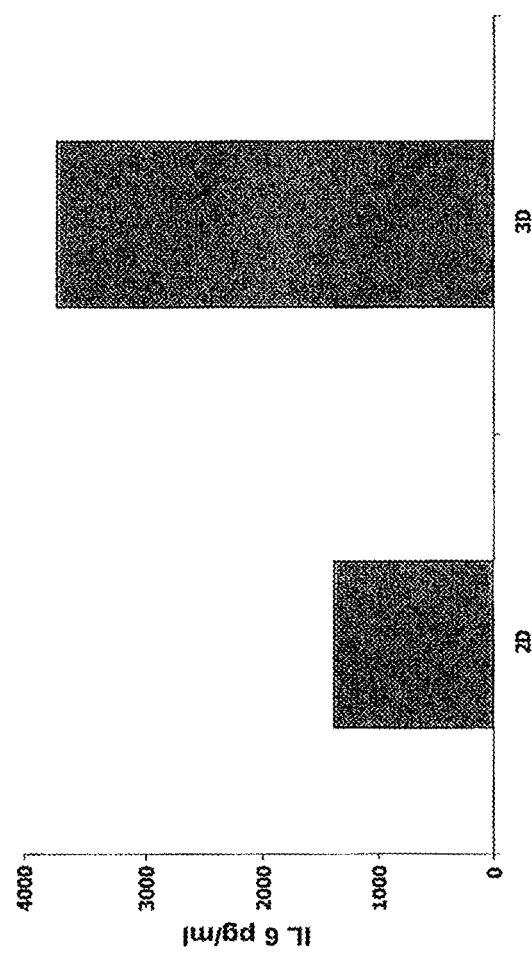

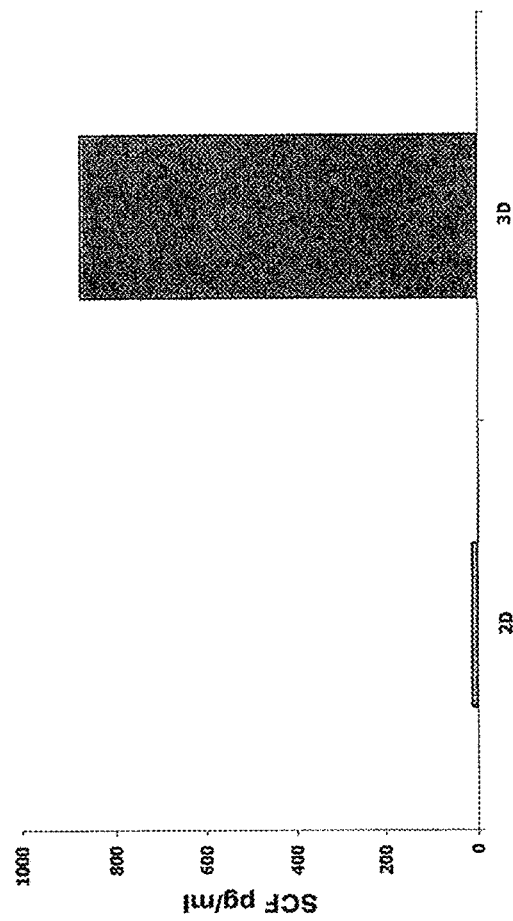

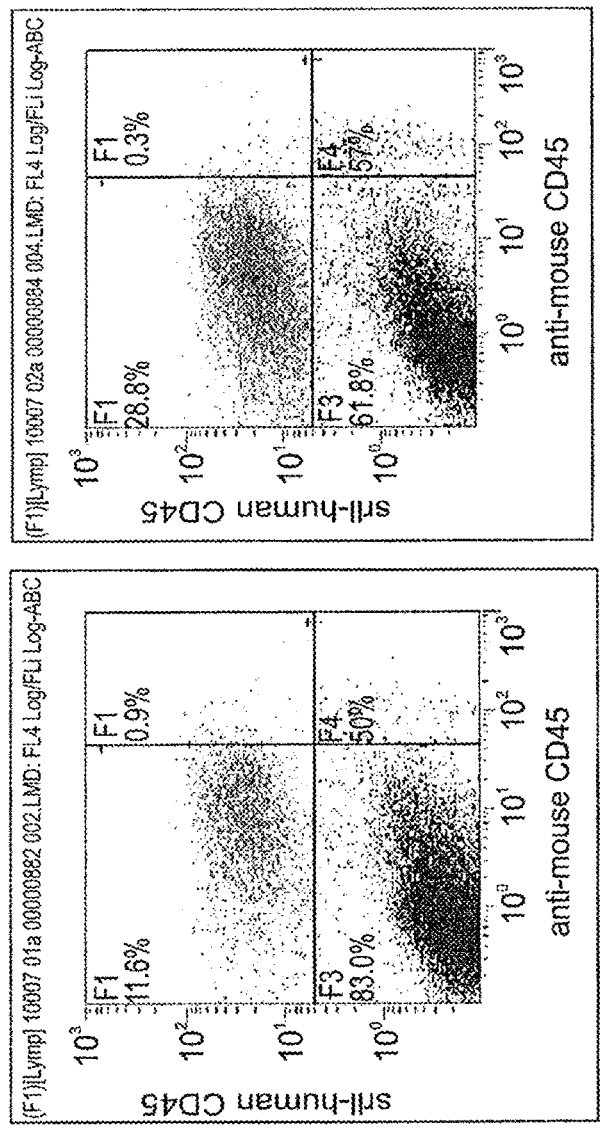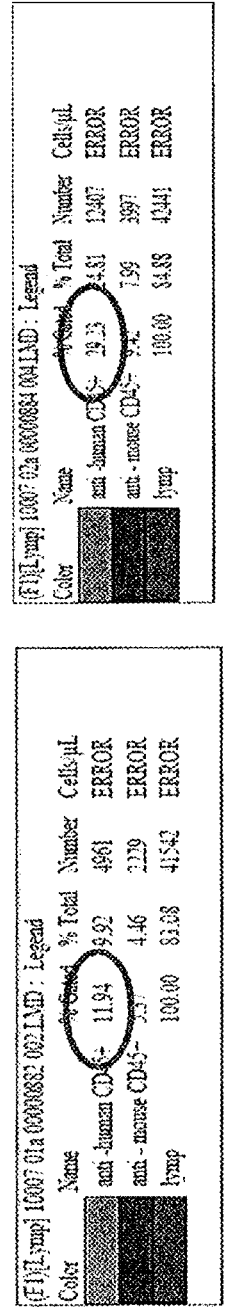
Fig. 6A
Fig. 6B
Human CD45+ (%)
Mouse CD45+ (%)

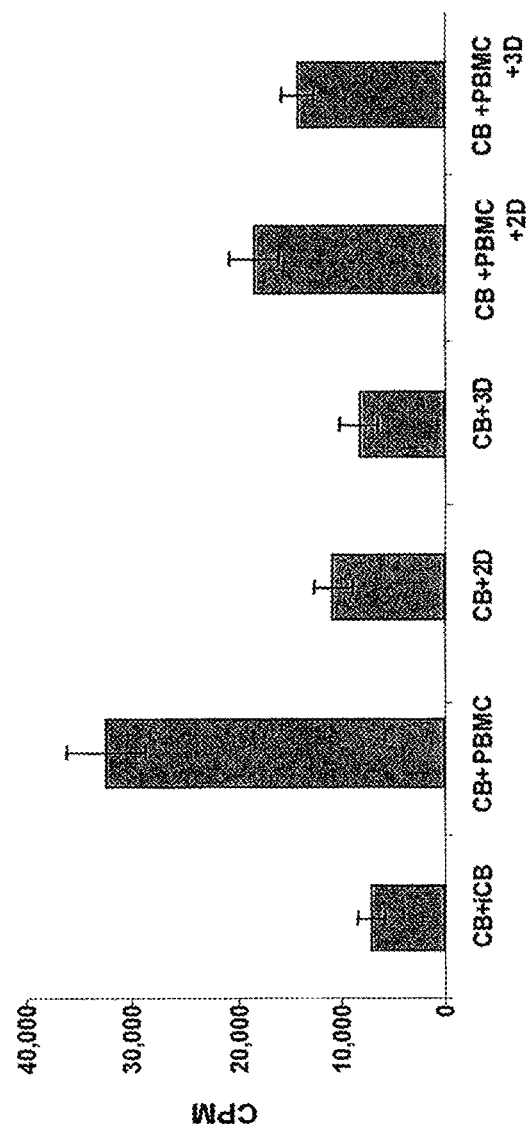

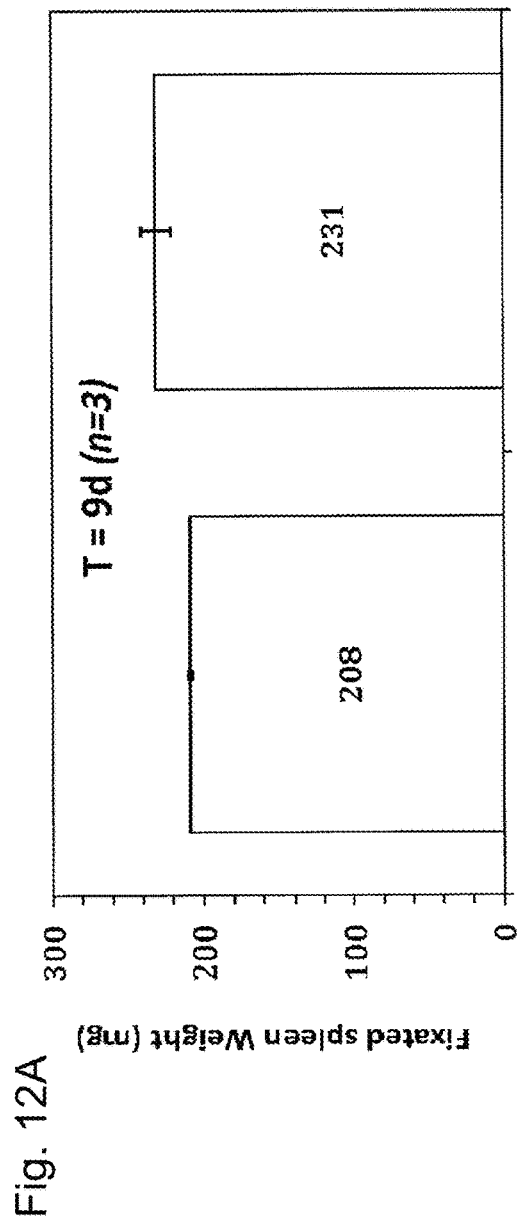
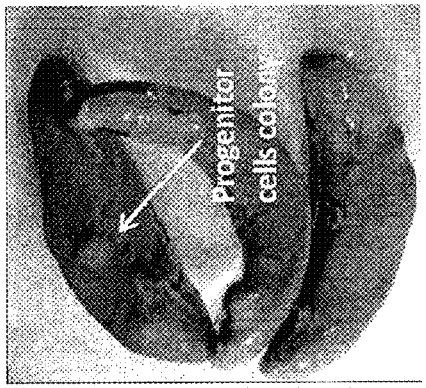
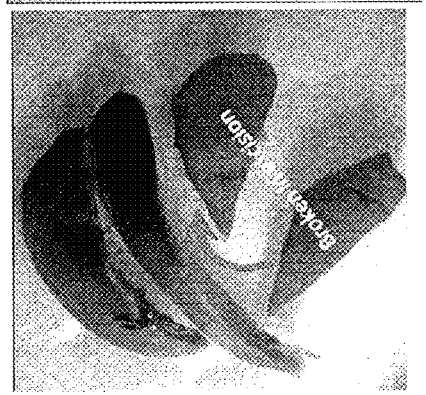
Fig. 12A — Spleen Colony Formation
Fig. 12B — Irradiated; Spleen colonies: 0, 0, 0
Fig. 12C — Irradiated + PLX; Spleen colonies: 3, 2, 1

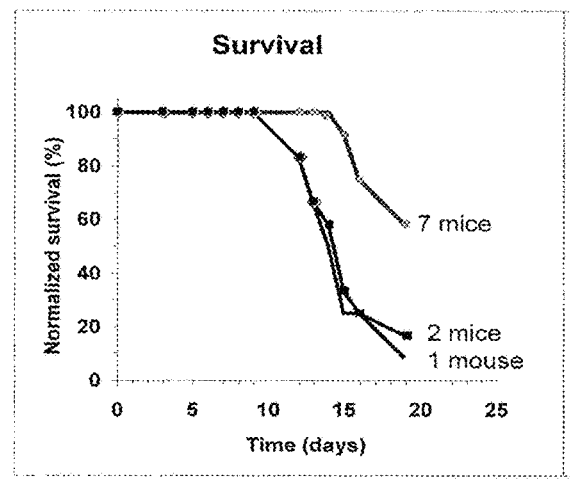 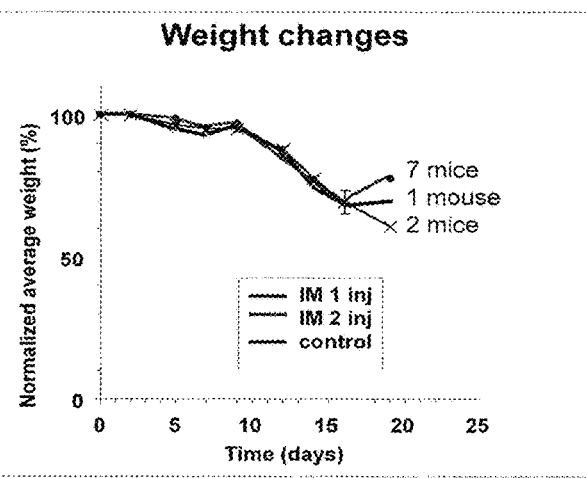
Fig. 27A Survival
Fig. 27B Weight changes

Major hematopoietic parameters of all survivors at the termination of the experiment

White blood cells

Red blood cells

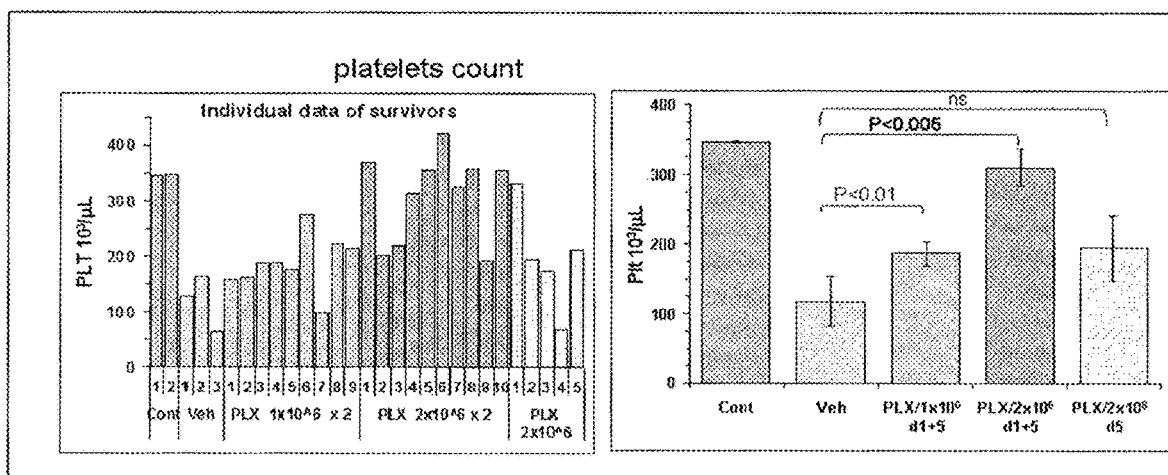

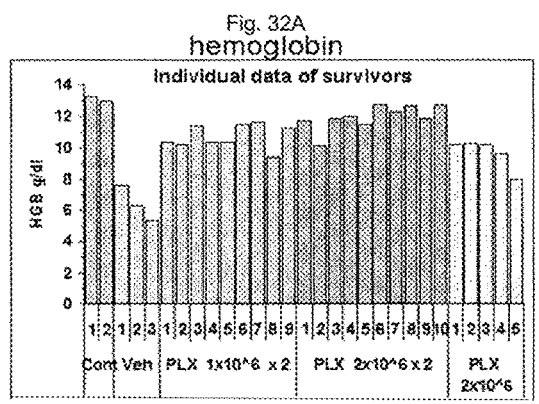
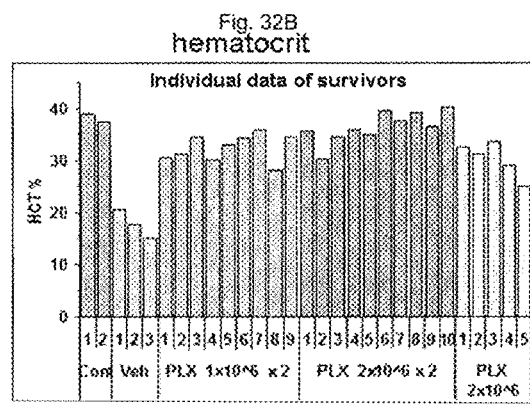
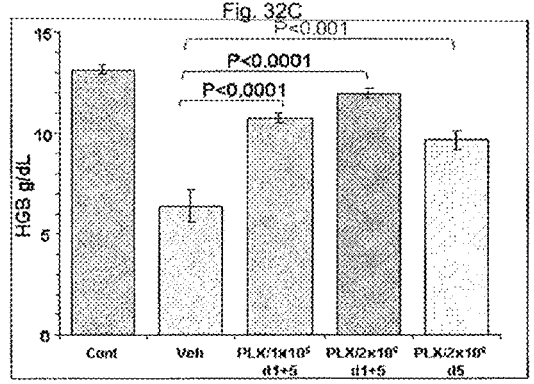
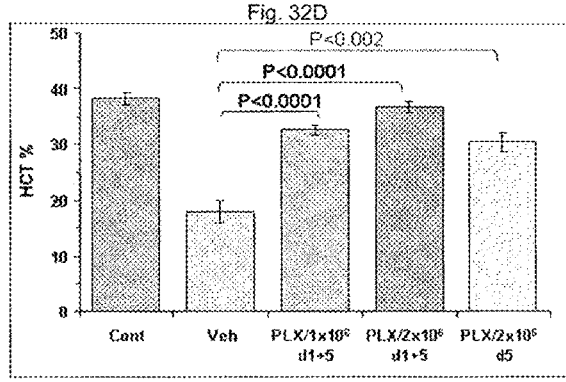

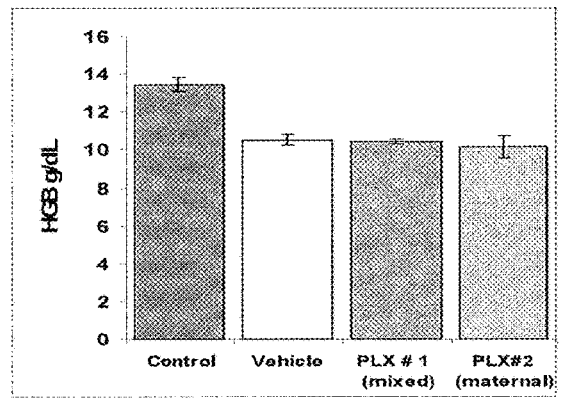
Fig. 38A
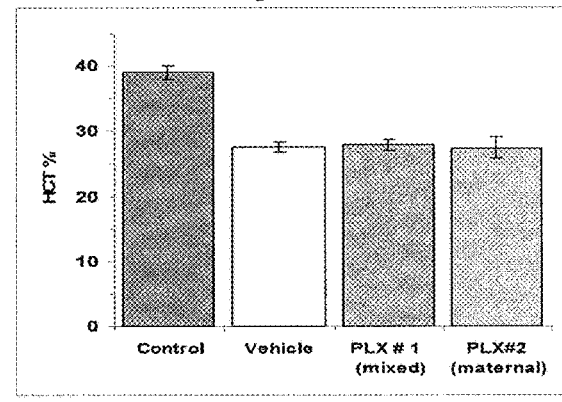
Fig. 38B
Fig. 39
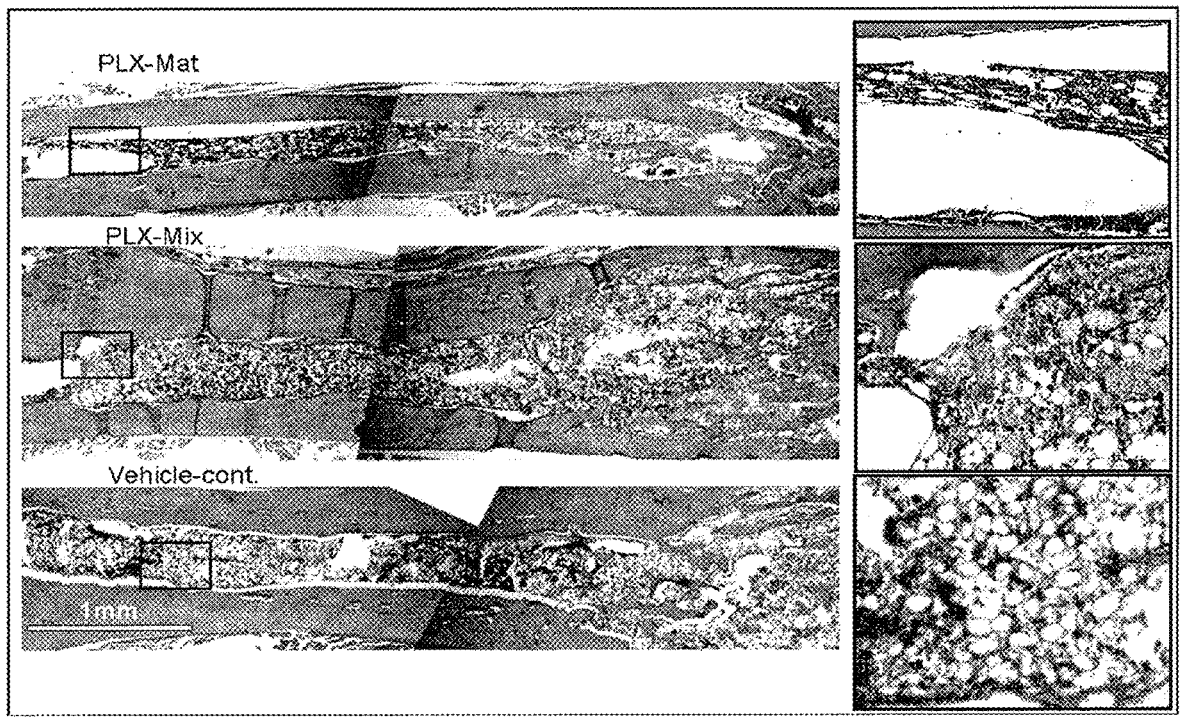

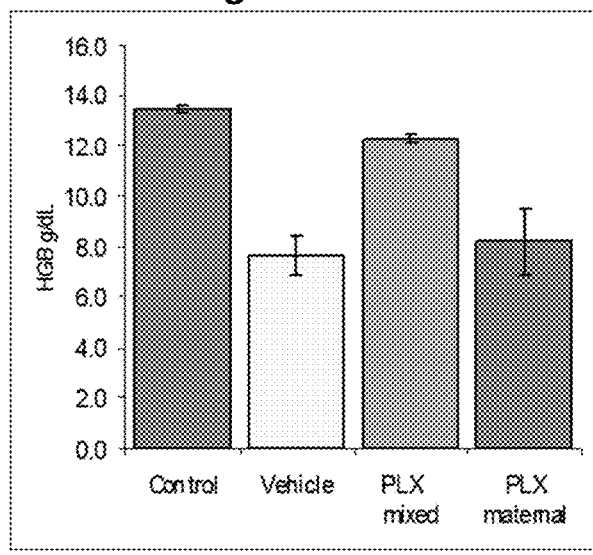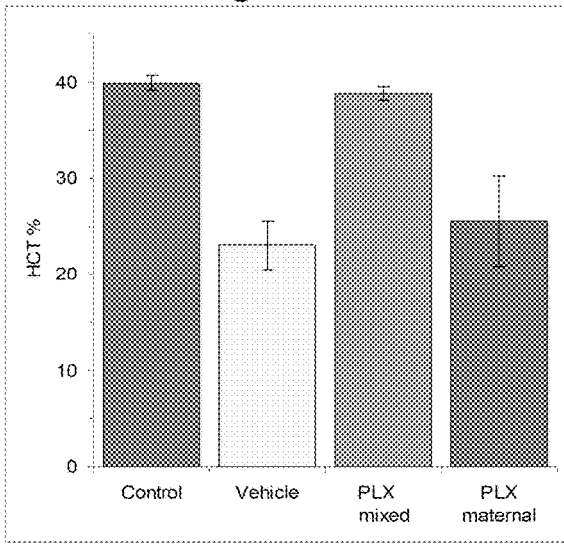

METHODS FOR TREATING RADIATION OR CHEMICAL INJURY

CROSS-REFERENCE TO RELATED APPLICATIONS

This application is a Continuation of U.S. application Ser. No. 14/006,580, which is the National Phase of International Application No. PCT/IB2012/000664, filed Mar. 22, 2012, said PCT/IB2012/000664 is a Continuation-in-part of U.S. application Ser. No. 13/069,130, filed Mar. 22, 2011; is a Continuation-in-part of U.S. application Ser. No. 13/161,334, filed Jun. 15, 2011; and claims the benefit of U.S. Provisional Application No. 61/497,400, filed Jun. 15, 2011; and U.S. Provisional Application No. 61/595,485, filed Feb. 6, 2012, the disclosures of which are incorporated herein by reference.

FIELD AND BACKGROUND OF THE INVENTION

The present invention relates to methods of treating injury from exposure to radiation or chemicals.

Hematopoietic stem cells (HSCs) are precursor cells that give rise to all blood cell types of both the myeloid and lymphoid lineages. Thus, HSC are necessary for the production of red blood cells, platelets, and lymphocytes, as well as most other blood cells. HSCs are intimately associated in vivo with discrete niches in the bone marrow, which provide molecular signals that collectively mediate HSC differentiation and self-renewal, via cell-cell contacts or short-range interactions. These niches are part of the hematopoietic inductive microenvironment, or stroma, that includes marrow cells, i.e. macrophages, fibroblasts, adipocytes and endothelial cells. The marrow cells maintain the functional integrity of the microenvironment by providing extra cellular matrix (ECM) proteins and basement membrane components that facilitate cell-cell contact. They also provide various soluble or resident cytokines needed for controlled hematopoietic cell differentiation and proliferation. The interactions between the HSC and the stroma are required to preserve the viability of the HSCs and to prevent their differentiation.

HSCs may be lost due to disease or exposure to substances that are toxic for this rapidly dividing population of cells. For example, exposure to harmful levels of radiation causes HSC death. Chemicals, including those used in cancer chemotherapy, may also kill HSCs. Patients deficient in HSCs no longer produce sufficient numbers of blood cells needed for functions ranging from oxygen transport (red blood cells), to clotting (platelets), to immunity (T cells, B cells). A complete loss of HSCs results in death in a matter of days if the patient is not treated by HSC transplantation. But even patients in which the number of HSCs is reduced but not completely lost are at grave risk of anemia, bleeding, infection, and other life-threatening conditions.

Although HSC transplantation can be used to treat conditions in which a subject has an insufficient number of HSCs, the low survival rate of the transplanted cells is a major problem. It is well documented that HSC transplanted intravenously are cleared from the circulation and visualized in the bone marrow within minutes after their transfusion. Three to five hours after HSCs transplantation, no donor cells are detected in the peripheral blood of the recipients. [Askenasy et al., Stem Cells 2002; 20:301-10.] But the vast majority of the transplanted cells are destroyed shortly after being transfused. Consequently, the colonization of the recipient's marrow is of low efficiency and only 1-5% of the transfused cells are detected in the recipient bone marrow 2-3 days post transplantation [Kerre et al., J Immunol. 2001; 167:3692-8; Jetmore et al., Blood 2002; 99:1585-93].

Several publications have demonstrated higher engraftment efficiencies of HSC when co-transplanted with mesenchymal stem cells. [Gurevitch et al., Transplantation 1999; 68:1362-8; Fan et al., Stem Cells 2001; 19:144-50.] It was also demonstrated that co-transplantation of human mesenchymal stem cells in a human-sheep engraftment model resulted in the enhancement of long-term engraftment of human HSC chimeric bone marrow in the animals. [Almeida-Porada et al., Blood 2000; 95:3620-7.] Simultaneous injection of HSC and mesenchymal stem cells can accelerate hematopoiesis. [Zhang et al., Stem Cells 2004; 22:1256-62; Liu et al., Zhonghua Xue Ye Xue Za Zhi. 2005; 26:385-8.] Mesenchymal stem cells have been used to promote engraftment of HSC in human subjects. [Koc O N, J Clin Oncol. 2000; 18:307-316; Lazarus H M, Biol Blood Marrow Transplant. 2005; 11:389-98.]. Apparently the mesenchymal stem cells contribution to hematopoietic engraftment by producing supporting cytokines that help mediate and balance the homing, self-renewal and commitment potentials of the transplanted HSCs, by rebuilding the damaged hematopoietic microenvironment needed for the homing and proliferation of the HSCs, and by inhibiting donor derived T cells, which may cause Graft vs. Host Disease (GvHD). [Charbord & Moore, Ann. N. Y. Acad. Sci 2005; 1044: 159-67; U.S. Pat. Nos. 6,010,696; 6,555,374.]

Although mesenchymal stem cells may facilitate HSC engraftment, they are not widely available in sufficient numbers for routine clinical application. Similarly, it can be difficult to provide an adequate supply of HSC, particularly HSC that are matched with the recipient and so less likely to be destroyed. Accordingly, there remains an unmet clinical need for alternatives therapies that may be used to treat subjects in which the hematopoietic system has been damaged, such as by exposure to radiation or chemicals.

SUMMARY OF THE INVENTION

According to one aspect of the invention, there is provided a method for treating a subject following exposure to radiation, comprising administering to the subject a therapeutically effective amount of adherent stromal cells to mitigate one or more effects of exposure to the radiation. In certain embodiments, the radiation is ionizing radiation. In certain embodiments, the ionizing radiation is radiotherapy. In certain embodiments, the exposure is accidental exposure to ionizing radiation.

In some of the embodiments, the effect of exposure to radiation can be one or more of nausea, vomiting, diarrhea, headache, fever, weight loss, a neurological symptom, leukopenia, anemia, thrombocytopenia, fatigue, weakness, purpura, hemorrhage, epilation, or shock. Likewise, in some of the embodiments of this aspect of the invention, the effect of exposure to radiation can be one or more of damage to the respiratory system, damage to the nervous system, damage to the gastrointestinal system, damage to the cardiovascular system, damage to the skin, or damage to the renal system. In certain embodiments, the neurological symptom is cognitive impairment, seizure, tremor, ataxia, or lethargy.

In some of the embodiments, the exposure to radiation may be ongoing.

In some of the embodiments, the subject is also receiving chemotherapy.

In some of the embodiments, the administration may be by intravascular injection, intramuscular injection, intraperitoneal injection, intrathecal injection, subcutaneous injection, or inhalation. In certain embodiments, the administration is by intramuscular injection or intravenous injection.

In some of the embodiments, exogenous hematopoietic stem cells are not administered to the subject.

In some of the embodiments, the invention may further comprise administering at least one additional therapeutically effective amount of adherent stromal cells about 2 to about 21 days following the first administration.

In some of the embodiments, the administration of the first therapeutically effective amount and the at least one additional therapeutically effective amount may be by intramuscular injection.

In some of the embodiments, the first therapeutically effective amount is administered about 0 to about 1, 2, or 3 days after exposure and the a least one additional therapeutically effective amount is administered about 2, about 3, about 4, or about 5 days later.

In some of the embodiments, the first therapeutically effective amount is administered before exposure to radiation. In some of the embodiments of this further aspect of the invention, the first therapeutically effective amount is administered about 1, about 2, about 3, about 4, or about 5 days prior to exposure. In some embodiments, at least part of the at least one additional therapeutically effective amount is also administered prior to exposure.

According to another aspect of the invention, there is provided a method for treating a subject receiving chemotherapy, comprising administering to the subject a therapeutically effective amount of adherent stromal cells to mitigate one or more effects of the chemotherapy.

In some of the embodiments, the effect of chemotherapy can be one or more of nausea, vomiting, diarrhea, headache, fever, weight loss, a neurological symptom, leukopenia, anemia, thrombocytopenia, fatigue, weakness, purpura, hemorrhage, epilation, or shock. Likewise, in some of the embodiments, the effect of chemotherapy can be one or more of damage to the respiratory system, damage to the nervous system, damage to the gastrointestinal system, damage to the cardiovascular system, damage to the skin, or damage to the renal system. In certain embodiments, the neurological symptom is cognitive impairment, seizure, tremor, ataxia, or lethargy.

In some of the embodiments, the chemotherapy may be ongoing.

In some of the embodiments, the subject is also exposed to radiation.

In some of the embodiments, the administration may be by intravascular injection, intramuscular injection, intraperitoneal injection, intrathecal injection, subcutaneous injection, or inhalation. In certain embodiments, the administration is by intramuscular injection or intravenous injection.

In some of the embodiments, exogenous hematopoietic stem cells are not administered to the subject.

In some of the embodiments, the invention may further comprise administering at least one additional therapeutically effective amount of adherent stromal cells about 2 to about 21 days following the first administration.

In some of the embodiments, the administration of the first therapeutically effective amount and the at least one additional therapeutically effective amount may be by intramuscular injection.

In some of the embodiments, the first therapeutically effective amount is administered about 0 to about 1, 2, or 3 days after exposure and the a least one additional therapeutically effective amount is administered about 2, about 3, about 4, or about 5 days later.

In some of the embodiments, the first therapeutically effective amount is administered before chemotherapy. In some of the embodiments of this further aspect of the invention, the first therapeutically effective amount is administered about 1, about 2, about 3, about 4, or about 5 days prior to chemotherapy. In some embodiments, at least part of the at least one additional therapeutically effective amount is also administered prior to chemotherapy.

According to another aspect, there is provided a method for treating a subject with a compromised endogenous hematopoietic system, comprising administering to the subject a therapeutically effective amount of adherent stromal cells to induce repopulation of endogenous hematopoietic cells and/or to mitigate reduction in the number of endogenous hematopoietic cells.

In some of the embodiments, repopulation of endogenous hematopoietic cells may comprise increasing the number of endogenous hematopoietic cells. In one embodiment, repopulation of endogenous hematopoietic cells may comprises increasing the number of hematopoietic cells expressing CD45.

In some of the embodiments, the endogenous hematopoietic system is compromised due to exposure to radiation or chemotherapy.

In some of the embodiments, the exposure to radiation or chemotherapy is ongoing.

In some of the embodiments, the effect of exposure to radiation or chemotherapy can be one or more of nausea, vomiting, diarrhea, headache, fever, weight loss, a neurological symptom, leukopenia, anemia, thrombocytopenia, fatigue, weakness, purpura, hemorrhage, epilation, or shock. Likewise, in some of the embodiments of this aspect of the invention, the effect of radiation or chemotherapy can be one or more of damage to the respiratory system, damage to the nervous system, damage to the gastrointestinal system, damage to the cardiovascular system, damage to the skin, or damage to the renal system. In certain embodiments, the neurological symptom is cognitive impairment, seizure, tremor, ataxia, or lethargy.

In some of the embodiments, the administration may be by intravascular injection, intramuscular injection, intraperitoneal injection, intrathecal injection, subcutaneous injection, or inhalation. In certain embodiments, the administration is by intramuscular injection or intravenous injection.

In some of the embodiments, exogenous hematopoietic stem cells are not administered to the subject.

In some of the embodiments, the invention may further comprise administering at least one additional therapeutically effective amount of adherent stromal cells about 2 to about 21 days following the first administration.

In some of the embodiments, the administration of the first therapeutically effective amount and the at least one additional therapeutically effective amount may be by intramuscular injection.

In some of the embodiments, the first therapeutically effective amount is administered about 0 to about 1, 2, or 3 days after exposure and the a least one additional therapeutically effective amount is administered about 2, about 3, about 4, or about 5 days later.

In some of the embodiments, the first therapeutically effective amount is administered before exposure to radiation. In some embodiments, the first therapeutically effective amount is administered about 1, about 2, about 3, about 4, or about 5 days prior to exposure.

According to another aspect, there is provided a method of treating a subject suffering from a compromised endogenous hematopoietic system due to exposure to radiation or chemotherapy, comprising: administering to the subject a first therapeutically effective amount of adherent stromal cells within a specified period after the exposure to radiation or chemotherapy, for inducing repopulation of endogenous hematopoietic cells and/or for mitigating reduction in the number of endogenous hematopoietic cells, and administering to the subject at least one additional therapeutically effective amount of adherent stromal cells to further induce repopulation of endogenous hematopoietic cells and/or for mitigating reduction in the number of endogenous hematopoietic cells.

In some of the embodiments, repopulation of endogenous hematopoietic cells may comprise increasing the number of endogenous hematopoietic cells. In one embodiment, repopulation of endogenous hematopoietic cells may comprises increasing the number of hematopoietic cells expressing CD45.

In some of the embodiments, the exposure to radiation or chemotherapy is ongoing.

In some of the embodiments, the effect of exposure to radiation or chemotherapy can be one or more of nausea, vomiting, diarrhea, headache, fever, weight loss, a neurological symptom, leukopenia, anemia, thrombocytopenia, fatigue, weakness, purpura, hemorrhage, epilation, or shock. Likewise, in some of the embodiments of this aspect of the invention, the effect of radiation or chemotherapy can be one or more of damage to the respiratory system, damage to the nervous system, damage to the gastrointestinal system, damage to the cardiovascular system, damage to the skin, or damage to the renal system. In certain embodiments, the neurological symptom is cognitive impairment, seizure, tremor, ataxia, or lethargy.

In some of the embodiments, the specified period is within 0-10 days. In certain embodiments, the specified period is within 7-10 days. In still other embodiments, the specified period is within 5-6 days. In yet other embodiments, the specified period is within 2-4 days. In additional embodiments, the specified period is within 1-2 days. In some embodiments, the specified period is within about 1 day.

In some of the embodiments, the first therapeutically effective amount is administered before exposure to radiation or chemotherapy. In some of the embodiments, the first therapeutically effective amount is administered about 1, about 2, about 3, about 4, or about 5 days prior to exposure.

In some of the embodiments, the administration of the at least one second therapeutically effect amount may be about 2 to about 21 days after administration of the first therapeutically effective amount. In certain embodiments, administration of the at least one second therapeutically effect amount is about 2 to about 10 days after administration of the first therapeutically effective amount. In other embodiments, administration of the at least one second therapeutically effect amount is about 2 to about 5 days after administration of the first therapeutically effective amount.

In some of the embodiments, administration of the first therapeutically effective amount may be by intravascular injection, intramuscular injection, intraperitoneal injection, subcutaneous injection, or inhalation.

In some of the embodiments, administration of the at least one additional therapeutically effective amount may be by intravascular injection, intramuscular injection, intraperitoneal injection, subcutaneous injection, or inhalation.

In some embodiments, administration of the first therapeutically effective amount and the at least one second therapeutically effective amount is by intramuscular injection.

According to yet another aspect, there is provided a method for treating a subject with a compromised endogenous hematopoietic system due to exposure to radiation or chemotherapy, comprising: administering to the subject a first therapeutically effective amount of adherent stromal cells within a specified period after the exposure to radiation or chemotherapy, for inducing repopulation of endogenous hematopoietic cells and/or for mitigating reduction in the number of endogenous hematopoietic cells, and administering to the subject at least one second therapeutically effective amount of adherent stromal cells together with exogenous hematopoietic stem cells after a matching period following the exposure, for further enhancing the repopulation of endogenous hematopoietic cells. The period of time required to find exogenous hematopoietic stem cells that match the subject is referred to as the "matching period."

In some of the embodiments, repopulation of endogenous hematopoietic cells may comprise increasing the number of endogenous hematopoietic cells. In one embodiment, repopulation of endogenous hematopoietic cells may comprises increasing the number of hematopoietic cells expressing CD45.

In some of the embodiments of this aspect of the invention, the exposure to radiation or chemotherapy is ongoing.

In some of the embodiments, the effect of exposure to radiation or chemotherapy can be one or more of nausea, vomiting, diarrhea, headache, fever, weight loss, a neurological symptom, leukopenia, anemia, thrombocytopenia, fatigue, weakness, purpura, hemorrhage, epilation, or shock. Likewise, in some of the embodiments, the effect of radiation or chemotherapy can be one or more of damage to the respiratory system, damage to the nervous system, damage to the gastrointestinal system, damage to the cardiovascular system, damage to the skin, or damage to the renal system. In certain embodiments, the neurological symptom is cognitive impairment, seizure, tremor, ataxia, or lethargy.

In some of the embodiments, the specified period is within 0-10 days. In certain embodiments, the specified period is within 7-10 days. In still other embodiments, the specified period is within 5-6 days. In yet other embodiments, the specified period is within 2-4 days. In additional embodiments, the specified period is within 1-2 days. In some embodiments, the specified period is within about 1 day.

In some of the embodiments, the first therapeutically effective amount is administered before exposure to radiation or chemotherapy. In some of the embodiments, the first therapeutically effective amount is administered about 1, about 2, about 3, about 4, or about 5 days prior to exposure.

In some of the embodiments, the administration of the at least one second therapeutically effect amount may be about 2 to about 21 days after administration of the first therapeutically effective amount. In certain embodiments, administration of the at least one second therapeutically effect amount is about 2 to about 10 days after administration of the first therapeutically effective amount. In other embodiments, administration of the at least one second therapeutically effect amount is about 2 to about 5 days after administration of the first therapeutically effective amount.

In some of the embodiments, administration of the first therapeutically effective amount may be by intravascular injection, intramuscular injection, intraperitoneal injection, subcutaneous injection, or inhalation.

In some of the embodiments, administration of the at least one additional therapeutically effective amount may be by intravascular injection, intramuscular injection, intraperitoneal injection, subcutaneous injection, or inhalation.

In some embodiment, administration of the first therapeutically effective amount and the at least one second therapeutically effective amount is by intramuscular injection.

In some of the embodiments, the invention may further comprise matching the exogenous hematopoietic stem cells to the subject. The period of time required to find exogenous hematopoietic stem cells that match the subject is referred to as the "matching period."

In some of the embodiments, the exogenous hematopoietic stem cells are matched allogeneic cord blood or bone marrow cells.

In some of the embodiments, the exogenous hematopoietic stem cells are matched with the subject but the adherent stromal cells are not matched with the hematopoietic stem cells and/or the adherent stromal cells are not matched with the recipient subject.

According to another aspect, there is provided a kit for treating a subject suffering from a compromised endogenous hematopoietic system due to exposure to radiation or chemotherapy, comprising: a therapeutically effective amount of adherent stromal cells in a sterile package, for inducing repopulation of endogenous hematopoietic cells and/or for mitigating reduction in the number of endogenous hematopoietic cells, and instructions for administration of the therapeutically effective amount.

In some of the embodiments, the sterile package is configured for intravascular injection, intramuscular injection, intraperitoneal injection, subcutaneous injection, or inhalation.

In some of the embodiments, the invention may further comprise a second therapeutically effective amount of adherent stromal cells in a second sterile package, for further enhancing repopulation of endogenous hematopoietic cells.

In some of the embodiments, the second therapeutically effective amount of adherent stromal cells is packaged together with exogenous hematopoietic stem cells in the second sterile package.

In some of the embodiments, the exogenous hematopoietic stem cells are allogeneic cord blood or bone marrow cells.

In some of the embodiments, the first and the second sterile packages are configured for intravascular injection, intramuscular injection, intraperitoneal injection, subcutaneous injection, or inhalation.

According to still another aspect, there is provided adherent stromal cells for treating a subject following exposure to radiation to mitigate effects of exposure to the radiation.

According to another aspect, there is provided adherent stromal cells for treating a subject receiving chemotherapy to mitigate effects of the chemotherapy.

According to still another aspect, there is provided adherent stromal cells for treating a subject following exposure to radiation and chemotherapy to mitigate effects of exposure to radiation and chemotherapy.

According to yet an additional aspect, there is provided adherent stromal cells for treating a subject with a compromised endogenous hematopoietic system to induce repopulation of endogenous hematopoietic cells and/or to mitigate reduction in the number of endogenous hematopoietic cells.

According to another aspect, there is provided adherent stromal cells for treating a subject suffering from a compromised endogenous hematopoietic system due to exposure to radiation or chemotherapy, comprising: administering to the subject a first therapeutically effective amount of adherent stromal cells within a specified period after the exposure to radiation or chemotherapy, for inducing repopulation of endogenous hematopoietic cells and/or to mitigate reduction in the number of endogenous hematopoietic cells, and administering to the subject at least one additional therapeutically effective amount of adherent stromal cells to further induce repopulation of endogenous hematopoietic cells and/or to mitigate reduction in the number of endogenous hematopoietic cells.

According to yet an additional aspect, there is provided adherent stromal cells for treating a subject with a compromised endogenous hematopoietic system due to exposure to radiation or chemotherapy, comprising: administering to the subject a first therapeutically effective amount of adherent stromal cells within a specified period after the exposure to radiation or chemotherapy, for inducing repopulation of endogenous hematopoietic cells and/or for mitigating reduction in the number of endogenous hematopoietic cells, and administering to the subject a second therapeutically effective amount of adherent stromal cells together with exogenous hematopoietic stem cells after a matching period following the exposure, for further enhancing the repopulation of endogenous hematopoietic cells. The period of time required to find exogenous hematopoietic stem cells that match the subject is referred to as the "matching period."

There is provided in another aspect a pharmaceutical composition comprising a therapeutically effective amount of any of the disclosed adherent stromal cells.

In an additional aspect, there is provided a kit comprising any of the disclosed pharmaceutical compositions in a sterile package and instructions for administering the pharmaceutical composition.

Another aspect provides for the use of adherent stromal cells in the preparation of a medicament for the practice of any of the disclosed methods.

According to one aspect, there is provided use of adherent stromal cells in the preparation of a medicament for treating a subject following exposure to radiation, wherein the treatment comprises administering to the subject a therapeutically effective amount of adherent stromal cells to mitigate effects of exposure to the radiation.

According to one aspect, there is provided use of adherent stromal cells in the preparation of a medicament for treating a subject receiving chemotherapy, wherein the treatment comprises administering to the subject a therapeutically effective amount of adherent stromal cells to mitigate effects of the chemotherapy.

According to one aspect, there is provided use of adherent stromal cells in the preparation of a medicament for treating a subject with a compromised endogenous hematopoietic system, wherein the treatment comprises administering to the subject a therapeutically effective amount of adherent stromal cells to induce repopulation of endogenous hematopoietic cells and/or to mitigate reduction in the number of endogenous hematopoietic cells.

According to one aspect, there is provided use of adherent stromal cells in the preparation of a medicament for treating a subject suffering from a compromised endogenous hematopoietic system due to exposure to radiation or chemotherapy, wherein the treatment comprises: administering to the subject a first therapeutically effective amount of adherent stromal cells within a specified period after the exposure to radiation or chemotherapy, for inducing repopulation of endogenous hematopoietic cells and/or for mitigating reduction in the number of endogenous hematopoietic cells, and administering to the subject at least one additional therapeutically effective amount of adherent stromal cells to further induce repopulation of endogenous hematopoietic cells.

According to one aspect, there is provided use of adherent stromal cells in the preparation of a medicament for treating a subject with a compromised endogenous hematopoietic system due to exposure to radiation or chemotherapy, wherein the treatment comprises: administering to the subject a first therapeutically effective amount of adherent stromal cells within a specified period after the exposure to radiation or chemotherapy, for inducing repopulation of endogenous hematopoietic cells and/or for mitigating reduction in the number of endogenous hematopoietic cells, and administering to the subject a second therapeutically effective amount of adherent stromal cells together with exogenous hematopoietic stem cells after a matching period following the exposure, for further enhancing the repopulation of endogenous hematopoietic cells. The period of time required to find exogenous hematopoietic stem cells that match the subject is referred to as the "matching period."

In certain embodiments of any of the several foregoing aspects, the origin of the adherent stromal cells is placenta, adipose tissue, or bone marrow.

In certain embodiments of any of the several foregoing aspects, the adherent stromal cells are cultured under three dimensional culturing conditions supporting cell expansion.

In certain embodiments of any of the several foregoing aspects, the origin of the adherent stromal cells is placenta, adipose tissue, or bone marrow, and the adherent stromal cells are cultured under three dimensional culturing conditions that support cell expansion without differentiation.

In certain embodiments of any of the several foregoing aspects, the adherent stromal cells are placental adherent stromal cells that have been cultured in a bioreactor under three dimensional culturing conditions that support cell expansion without differentiation.

In certain embodiments of any of the several foregoing aspects, less than about 60% of the placental adherent stromal cells are positive for the marker CD200, as detected by flow cytometry compared to an isotype control.

In certain embodiments of any of the several foregoing aspects, less than about 60% of the placental adherent stromal cells are positive for the marker OCT-4, as detected by immunofluorescence compared to an isotype control.

In certain embodiments of any of the several foregoing aspects, the adherent stromal cells secrete Flt-3 ligand, IL-6, and SCF.

In certain embodiments of any of the several foregoing aspects, exogenous hematopoietic stem cells are not administered to the subject.

According to a further aspect, there is provided a method for treating a subject suffering from a compromised endogenous hematopoietic system, comprising administering to the subject at least one therapeutically effective amount of adherent cells for inducing repopulation of endogenous hematopoietic cells and/or for mitigating reduction in the number of endogenous hematopoietic cells in the endogenous hematopoietic system.

According to a further aspect, there is provided a use of adherent cells for the manufacture of a medicament for use in the treatment at a specified dosage regime, of a compromised endogenous hematopoietic system due to exposure to radiation or chemotherapy, characterized in that the specified dosage regime comprises: a therapeutically effective amount of adherent cells for administration within ten days after exposure to radiation or chemotherapy.

According to a further aspect, there is provided a kit for treating a subject suffering from a compromised endogenous hematopoietic system due to exposure to radiation or chemotherapy, comprising: a therapeutically effective amount of adherent cells within a sterile package, for administration within a specified period after exposure to radiation or chemotherapy.

According to still further features of the described embodiments, the adherent cells induce repopulation of endogenous hematopoietic cells and/or mitigate reduction in the number of endogenous hematopoietic cells in the endogenous hematopoietic system.

According to still further features of the described embodiments, the endogenous hematopoietic cells were produced by the subject's hematopoietic system.

According to still further features of the described embodiments, repopulation of endogenous hematopoietic cells comprises increasing the number of hematopoietic cells in the endogenous hematopoietic system of the subject.

According to still further features of the described embodiments, repopulation of endogenous hematopoietic cells comprises increasing the number of hematopoietic cells expressing the CD45 marker.

According to still further features of the described embodiments, the subject has been exposed to radiation.

According to still further features of the described embodiments, the radiation exposure is ongoing.

According to still further features of the described embodiments, the subject has been exposed to chemicals that damage the hematopoietic system.

According to still further features of the described embodiments, the subject has been treated with chemotherapy.

According to still further features of the described embodiments, the chemotherapy is ongoing.

According to still further features of the described embodiments, the origin of the adherent cells is placenta, adipose tissue, or bone marrow.

According to still further features of the described embodiments, the adherent cells were cultured under three dimensional culturing conditions supporting cell expansion.

According to still further features of the described embodiments, less than about 60% of the placental adherent stromal cells are positive for the marker CD200, as detected by flow cytometry compared to an isotype control.

According to still further features of the described embodiments, less than about 60% of the placental adherent stromal cells are positive for the marker OCT-4, as detected by immunofluorescence compared to an isotype control.

According to still further features of the described embodiments, the adherent stromal cells secrete Flt-3 ligand, IL-6, and SCF.

According to still further features of the described embodiments, the origin of the adherent cells is placenta, adipose tissue, or bone marrow, and the adherent cells were cultured under three dimensional culturing conditions supporting cell expansion without differentiation.

According to still further features of the described embodiments, the origin of the adherent cells is placenta and the adherent cells were cultured under three dimensional culturing conditions supporting cell expansion without differentiation.

According to still further features of the described embodiments, the adherent cells are administered by intramuscular injection.

According to still further features of the described embodiments, the adherent cells are administered at least two times, three times, four times, five times, or up to ten times.

According to still further features of the described embodiments, the adherent cells are administered at least two times and are administered 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days apart.

According to still further features of the described embodiments, the adherent cells are administered intramuscularly at least two times and are administered 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days apart.

According to another aspect, there is provided a pharmaceutical composition comprising a therapeutically effective amount of adherent cells for inducing repopulation of endogenous hematopoietic cells and/or for mitigating reduction in the number of endogenous hematopoietic cells in the endogenous hematopoietic system in a subject suffering from a compromised hematopoietic system.

According to a further aspect, there is provided a method for treating a subject suffering from a compromised endogenous hematopoietic system due to exposure to radiation or chemicals, comprising: administering to the subject a first therapeutically effective amount of adherent cells within a specified period after the exposure to radiation or chemicals, and administering to the subject a second therapeutically effective amount of adherent cells together with exogenous hematopoietic stem cells after a matching period following the exposure. The period of time required to find exogenous hematopoietic stem cells that match the subject is referred to as the "matching period." In some embodiments, the hematopoietic stem cells are matched allogeneic cord blood or bone marrow cells. In some embodiments, the therapy induces repopulation of endogenous hematopoietic cells in the subject. In some embodiments, the therapy mitigates reduction in the number of endogenous hematopoietic cells in the subject. In some embodiments, the chemical exposure is chemotherapy. In some embodiments, the radiation is ionizing radiation.

According to yet another aspect, there is provided a method for treating a subject suffering from a compromised endogenous hematopoietic system due to exposure to radiation or chemicals, comprising: administering to the subject a first therapeutically effective amount of adherent cells within a specified period after the exposure to radiation or chemicals, and administering to the subject at least one additional therapeutically effective amount of adherent cells. In some embodiments, the origin of each of the therapeutically effective amounts of adherent cells is placenta, adipose tissue, or bone marrow, and the adherent cells were cultured under three dimensional culturing conditions supporting cell expansion. In some embodiments, the therapy induces repopulation of endogenous hematopoietic cells in the subject. In some embodiments, the therapy mitigates reduction in the number of endogenous hematopoietic cells in the subject. In some embodiments, the chemical exposure is chemotherapy. In some embodiments, the radiation is ionizing radiation.

According to a further aspect, there is provided a kit for treating a subject suffering from a compromised endogenous hematopoietic system due to exposure to radiation or chemicals, comprising: a first therapeutically effective amount of adherent cells within a first sterile package, for administration within a specified period after the exposure to radiation or chemicals, a second therapeutically effective amount of adherent cells that is optionally provided together with hematopoietic stem cells, within a second sterile package, for administration after a matching period following the exposure, and instructions for administration of the first and second therapeutically effective amounts. In those embodiments in which hematopoietic stem cells are provided as part of the kit, in certain embodiments the hematopoietic cells are provided as matched allogeneic cord blood or bone marrow cells. In some embodiments, the therapy induces repopulation of endogenous hematopoietic cells in the subject. In some embodiments, the therapy mitigates reduction in the number of endogenous hematopoietic cells in the subject. In some embodiments, the chemical exposure is chemotherapy. In some embodiments, the radiation is ionizing radiation.

According to a further aspect, there is provided a use of adherent cells for the manufacture of a medicament for use in the treatment at a specified dosage regime, of a compromised endogenous hematopoietic system due to exposure to radiation or chemicals, characterized in that the specified dosage regime comprises: a first therapeutically effective amount of adherent cells within ten days after the exposure to radiation or chemotherapy, and at least one second therapeutically effective amount of adherent cells after a second specified period. In some embodiments, the therapy induces repopulation of endogenous hematopoietic cells in the subject. In some embodiments, the therapy mitigates reduction in the number of endogenous hematopoietic cells in the subject. In some embodiments, the chemical exposure is chemotherapy. In some embodiments, the radiation is ionizing radiation.

According to still further features in the described embodiments the at least one second therapeutically effective amount further comprises matched allogeneic cord blood or bone marrow cells and wherein the second specified period is a matching period of matching the matched cells to the subject.

According to still further aspects, there is provided a method of treating a subject that has been exposed to radiation or chemicals comprising administering to the exposed subject a therapeutically effective amount of adherent stromal cells. In some embodiments, the chemical exposure is chemotherapy. In some embodiments, the radiation is ionizing radiation. In some embodiments, the exposure is such that, if left untreated, it would generally be lethal to the subject within about 1-2 days (e.g., exposures of greater than 30 Gy ionizing radiation (IR)), 2 days to 2 weeks (e.g., exposures of about 8-30 Gy IR), or about 2-4 weeks (e.g., exposures of about 2-8 Gy IR).

According to yet another aspect, there is also provided a method of reducing symptoms associated with radiation sickness or exposure to toxic chemicals comprising administering to an exposed subject a therapeutically effective amount of adherent stromal cells. In some embodiments, the radiation sickness is acute. In some embodiments, the toxic chemicals are administered as part of a chemotherapy. In either of these embodiments, symptoms include, but are not limited to, nausea and vomiting, diarrhea, headache, fever, weight loss, neurological symptoms (e.g., cognitive impairment, seizures, tremor, ataxia, lethargy), leukopenia, anemia, thrombocytopenia, fatigue, weakness, purpura, hemorrhage, epilation, and shock. In some embodiments, the radiation or chemotherapy results in damage to the respiratory system, damage to the nervous system, damage to the gastrointestinal system, damage to the cardiovascular system, damage to the skin, or damage to the renal system.

In some of the various embodiments of these aspects, the timing of the administration, the number of doses, and the route(s) of administration are as described above.

In certain embodiments of these various aspects, exogenous hematopoietic stem cells are not administered to the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1G depict the bone-like microenvironment created in the bioreactor system containing 3-D carriers. FIGS. 1A-1B are electron micrographs depicting the comparison of natural bone (FIG. 1A) and the structure of the PluriX™ 3D carrier 7 days after seeding Adherent Stromal Cells (3D-ASC), imitating the bone micro-environment (FIG. 1B). FIGS. 1C-1F are electron micrographs depicting the PluriX™ 3D matrix seeded with 3D-ASC, produced from bone marrow, 20 days (FIGS. 1C-1D, magnified ×150 and 250 respectively) and 40 days (FIGS. 1E-1F, magnified ×350 and 500 respectively) after seeding. FIG. 1G is a diagram of the Plurix 3D plug flow bioreactor with separate parts defined by numbers: Culture medium reservoir (1), gas mixture supply (2), filter (3), injection point (4), column in which the 3D carriers are placed (5) flow monitor (6), flow valve (6a), separating container (7), cell growth analyzers (8); peristaltic pump (9), sampling point (10), dissolved $O_2$ measurement electrode (11), pH measurement electrode (12), control system (13), fresh growth media (14), used growth media (15).

FIGS. 4A-4D are bar graphs depicting a comparison of protein levels in ASCs produced from the placenta cultured under 2D and 3D Conditions or conditioned media of same. FIGS. 4A-4C depict levels of Flt-3 ligand (FIG. 4A), IL-6 (FIG. 4B) and SCF (FIG. 4C) in pg/ml, normalized for $1\times10^6$ cells/ml, as analyzed by ELISA, in the conditioned media of 2D and 3D cultured ASCs. Results represent one of three independent experiments. FIG. 4D shows the expression levels of different cellular proteins, as analyzed by mass spectrometry with iTRAQ reagents labeled protein samples compared therebetween. Protein samples were taken from ASCs grown under 2D (white bars) and 3D (grey bars) conditions. The figure represents one of two replica experiments. Note the difference in expression level of some of the proteins in cells and conditioned media of 2D and 3D culture conditions.

FIGS. 6A-6B are FACS analyses of human graft CD45+ cells in mice transplanted with CD34+ cells only (FIG. 6A) in comparison to CD34+ cells together with adipose tissue derived ASCs. (FIG. 6B). Note the significantly higher percentage of human hematopoietic population (hCD45+) (FIG. 6A—29%) in a mouse co-transplanted with adipose tissue derived ASC in comparison to a mouse treated with human CD34+ alone (FIG. 6B—12%).

FIG. 7 is a bar graph depicting a mixed lymphocyte reaction conducted between human cord blood mononuclear cells (CB), and equal amounts of irradiated (3000 Rad) cord blood cells (iCB), human peripheral blood derived monocytes (PBMC), 2D cultured (2D) or 3D cultured (3D) placental ASC, or a combination of PBMC and 2D and 3D cultured placental ASCs (PBMC+2D and PBMC+3D). Size of CB cell population is represented by the $^3$H-thymidine uptake (measured in CPM) which was measured during the last 18 hours of culturing. Elevation in stimulated CB cell proliferation indicates an immune response of a higher level. Note the lower level of immune response exhibited by cells incubated with adherent cells, and, in particular, the reduction of CB immune response to PBMCs when co-incubated with adherent cells. Three replicates were made of each reaction.

FIGS. 12A-12C illustrate spleen weight (FIG. 12A) in irradiated mice either untreated (left) or treated (right) with PLX cells and further visually illustrates exemplary prepared spleens from the corresponding groups of mice (FIGS. 12B and 12C, respectively). The preparation was carried out 9 days after C3H mice were exposed to sub-lethal irradiation, followed by 3D-ASC (PLX) injection, BM cell regeneration was tested by the spleen colony formation assay. The colonies originated from progenitor cells re-suspended in BM.

FIGS. 27A-27B illustrate survival (FIG. 27A) and normalized weight changes (FIG. 27B) following exposure of mice to radiation. Irradiated mice treated intramuscularly (IM) with one (squares) or two (circles) doses of adherent stromal cells (ASC) are shown compared to control mice not treated with ASC.

FIG. 30C (WBC) and FIG. 30D (RBC) present the pooled data for each group.

FIGS. 31A-31B present the day 23 platelet counts for individual mice (FIG. 31A) and the averaged groups (FIG. 31B).

FIGS. 32A-32D present the day 23 results for hemoglobin (FIG. 32A, FIG. 32C) and hematocrit (FIG. 32B, FIG. 32D) for individual mice (FIG. 32A, FIG. 32B) and values averaged by group (FIG. 32C, FIG. 32D).

FIG. 34A presents the total bone marrow counts. FIG. 34B presents the white blood cell counts. FIG. 34C presents the red blood cell counts. FIG. 34D presents the platelet counts.

FIGS. 38A-38B show the hematocrit (FIG. 38A) and hemoglobin (FIG. 38B).

FIG. 39 illustrates histology for decalcified femurs.

FIG. 41A presents the total bone marrow counts. FIG. 41B the white blood cell counts. FIG. 41C the red blood cell counts. FIG. 41D presents the platelet counts.

FIG. 42A-42B present the day 23 hemoglobin (FIG. 42A) and hematocrit (FIG. 42B).

DETAILED DESCRIPTION OF EMBODIMENTS

Figure 2:
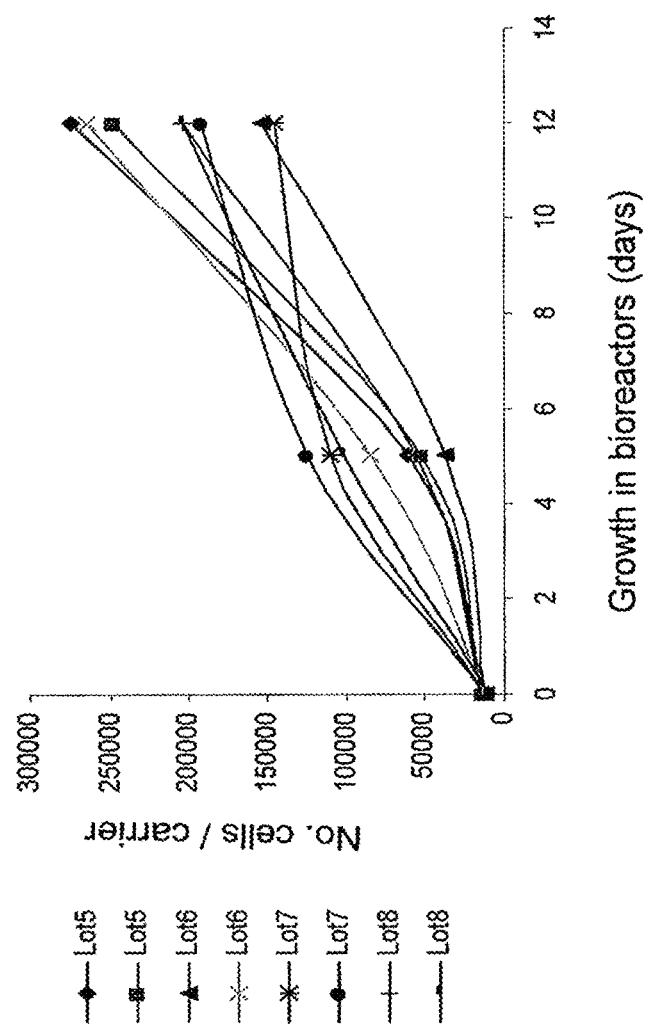
FIG. 2 is a graph depicting different production lots of adherent stromal cells (3D-ASC; Lots 5-8) originating from placenta, grown in 3D growth conditions within the bioreactor systems. ASCs ($2\times10^6$) were seeded in the bioreactor at a density of 10000-15000 cells/a carrier. Following a 12 day culture 3D-ASCs reached a density of between 150,000-250,000 cells/carrier or $22.5-37.5\times10^6$ in a bioreactor containing 150 carriers.

The present invention includes methods of cell expansion and uses of cells and conditioned medium produced thereby. Encompassed within the invention are methods of treating a subject following exposure to harmful levels of radiation, comprising administering to the subject a therapeutically effective amount of adherent stromal cells to mitigate effects of exposure to the radiation. Also encompassed within the invention are methods for treating a subject receiving chemotherapy, comprising administering to the subject a therapeutically effective amount of adherent stromal cells to mitigate effects of the chemotherapy. These methods derive from the inventor's recognition that adherent stromal cells administered to a subject following irradiation or chemotherapy promotes survival of the subject and that in a subject with a compromised hematopoietic system the adherent stromal cells facilitate the recovery of the subject's endogenous hematopoietic system and/or mitigate reduction in the number of endogenous hematopoietic cells.

The principles and operation of the present invention may be better understood with reference to the drawings and accompanying descriptions. Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered that adherent cells from placenta, adipose tissue, or bone marrow can be efficiently propagated in 3D culturing conditions. Accordingly, the adherent cells from placenta, adipose tissue, or bone marrow, and the conditioned medium produced therefrom, can be used for therapies such as transplantation, tissue regeneration and in vivo HSC support.

As is illustrated herein below and in the Examples section which follows, the present inventors were able to expand adipose, bone marrow, and placenta-derived adherent cells in 3D settings. Cells expanded accordingly were found viable, following cryo-preservation, as evidenced by adherence and re-population assays (see Example 1). Flow cytometry analysis of placenta-derived adherent cells uncovered a distinct marker expression pattern and (see FIGS. 3A-3B). Most importantly, adipose and placenta derived adherent cells propagated on 2D or 3D settings were able to support HSC engraftment (see Example 2), substantiating the use of the cells of the present invention in the clinic.

Thus, according to one aspect of the present invention, there is provided a method of cell expansion, the method comprising culturing adherent cells from placenta, adipose tissue, or bone marrow under three-dimensional (3D) culturing conditions which support cell expansion.

As used herein the terms "expanding" and "expansion" refer to substantially differentiationless maintenance of the cells and ultimately cell growth, i.e., increase of a cell population (e.g., at least 2 fold) without differentiation accompanying such increase.

As used herein the terms "maintaining" and "maintenance" refer to substantially differentiationless cell renewal, i.e., substantially stationary cell population without differentiation accompanying such stationarity.

As used herein the phrase "adherent cells" refers to a homogeneous or heterogeneous population of cells which are anchorage dependent, i.e., require attachment to a surface in order to grow in vitro.

As used herein the phrase "adipose tissue" refers to a connective tissue which comprises fat cells (adipocytes).

As used herein the term "placenta tissue" refers to any portion of the mammalian female organ which lines the uterine wall and during pregnancy envelopes the fetus, to which it is attached by the umbilical cord. Following birth, the placenta is expelled (and is referred to as a post partum placenta).

As used herein the phrase "three dimensional culturing conditions" refers to disposing the cells to conditions which are compatible with cell growth while allowing the cells to grow in more than one layer. It is well appreciated that the in situ environment of a cell in a living organism (or a tissue) as a three dimensional architecture. Cells are surrounded by other cells. They are held in a complex network of extra cellular matrix nanoscale fibers that allows the establishment of various local microenvironments. Their extracellular ligands mediate not only the attachment to the basal membrane but also access to a variety of vascular and lymphatic vessels. Oxygen, hormones and nutrients are ferried to cells and waste products are carried away. The three dimensional culturing conditions of the present invention are designed to mimic such as environment as is further exemplified below.

Placenta derived adherent stromal cells may be obtained from both fetal (i.e., amnion or inner parts of the placenta) and maternal (i.e., decidua basalis, and decidua parietalis) parts of the placenta. Thus, "maternal" adherent stromal cells from a placenta comprise at least about 70%, 75%, 80%, 85%, 90%, 92%, 94%, 95%, 96%, 98%, 99% or even 100% of cells from a maternal portion of placenta. Similarly, "fetal" adherent stromal cells comprise at least about 70%, 75%, 80%, 85%, 90%, 92%, 94%, 95%, 96%, 98%, 99% or even 100% adherent cells from a fetal portion of placenta.

Methods of preparing and characterizing maternal-derived and fetal-derived adherent stromal cells are described in WO 2011/064669, which is incorporated by reference. In some embodiments, maternal and fetal placental adherent stromal cells are identified based on genotype and/or karyotype (e.g., FISH) analysis. For example, adherent stromal cells from a placenta of a male embryo can be separated into fetal and maternal cells based on karyotype analysis (i.e., XX cells are maternal while XY cells are fetal). In some embodiments, adherent stromal cells derived from a fetal portion of the placenta (e.g., consisting of or comprising chorionic villi) express CD200. That is, at least about 50%, 55%, 60%, 65%, 70%, 75%, 80%, 85%, 90%, 95%, 96%, 97%, 98%, 99% or 100% of the cells express CD200 as measured by flow cytometry using an isotype control to define negative expression. In some embodiments, not more than 3.5%, not more than 3%, not more than 2%, or not more than 1% of the adherent stromal cells from a maternal portion express CD200 as measured by flow cytometry using an isotype control to define negative expression.

Irrespective of whether maternal, fetal, or mixed maternal and fetal-derived placental adherent cells are being prepared, tissue specimens are washed in a physiological buffer [e.g., phosphate-buffered saline (PBS) or Hank's buffer). Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

Adipose tissue derived adherent stromal cells may be isolated by a variety of methods known to those skilled in the art. For example, such methods are described in U.S. Pat. No. 6,153,432. The adipose tissue may be derived from omental/visceral, mammary, gonadal, or other adipose tissue sites. A preferred source of adipose tissue is omental adipose. In humans, the adipose is typically isolated by liposuction.

Isolated adherent stromal cells from adipose tissue may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 800 microns. The cells are then subjected to differential centrifugation directly in media or over a Ficoll or Percoll or other particulate gradient. Cells are centrifuged at speeds of between 100 to 3000×g for periods of between 1 minutes to 1 hour at temperatures of between 4-50° C. (see U.S. Pat. No. 7,078,230).

In addition to placenta or adipose tissue derived adherent stromal cells, the present invention also envisages the use of adherent stromal cells from other cell sources. For example, in certain embodiments, the adherent stromal cells are obtained from bone marrow. Other tissue sources from which adherent stromal cells can be retrieved include, but are not limited to, cord blood, hair follicles [e.g. as described in Us Pat. App. 20060172304], testicles [e.g., as described in Guan K., et al., Nature. 2006 Apr. 27; 440(7088): 1199-203], human olfactory mucosa [e.g. as described in Marshall, C T., et al., Histol Histopathol. 2006 June; 21(6):633-43], embryonic yolk sac [e.g., as described in Geijsen N, Nature. 2004 Jan. 8; 427(6970):148-54] and amniotic fluid [Pieternella et al. (2004) Stem Cells 22:1338-1345]. Adherent stromal cells from these tissue sources can be isolated by culturing the cells on an adherent surface, thus isolating adherent stromal cells from other cells in the initial population.

Regardless of the origin (e.g., placenta, adipose tissue, or bone marrow), cell retrieval generally effected under sterile conditions. Once isolated cells are obtained, they are allowed to adhere to an adherent material (e.g., configured as a surface) to thereby isolate adherent stromal cells. This may be effected prior to (see Example 1) or concomitant with culturing in 3D culturing conditions.

As used herein "an adherent material" refers to a synthetic, naturally occurring or a combination of same of a non-cytotoxic (i.e., biologically compatible) material having a chemical structure (e.g., charged surface exposed groups) which may retain the cells on a surface.

Examples of adherent materials which may be used in accordance with this aspect of the present invention include, but are not limited to, a polyester, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, chondronectin, laminin), a collagen, a poly L lactic acid and an inert metal fiber.

Further steps of purification or enrichment for cells expressing particular markers may be effected using methods which are well known in the art (such as by FACS using adherent stromal cell marker expression, as further described herein below).

Non-limiting examples of base media useful in culturing according to the present invention include Minimum Essential Medium Eagle, ADC-I, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E– with Earle's sale base), Medium M 199 (M 199H– with Hank's salt base), Minimum Essential Medium Eagle (MEM-E– with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or other species, and optionally or alternatively, growth factors, cytokines, and hormones (e.g., growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between pigogram/ml to milligram/ml levels.

It is further recognized that additional components may be added to the culture medium. Such components may be antibiotics, antimycotics, albumin, amino acids, and other components known to the art for the culture of cells.

Additionally, components may be added to enhance the differentiation process when needed (see further below).

Adherent stromal cells may be propagated in vitro by conventional two dimensional (2D) culture conditions or under three dimensional (3D) culture conditions. The phrase "two dimensional culture" or "2D" refers to a culture in which the cells grow primarily in one plane, as in a tissue culture dish.

Once adherent stromal cells are at hand they may be passaged to three dimensional settings (see Example 1 of the Examples section which follows). It will be appreciated though, that the cells may be transferred to a 3D-configured matrix immediately after isolation (as mentioned hereinabove).

The phrase "three dimensional culture" or "3D" refers to a culture in which the cells are cultured under conditions that are compatible with cell growth and that include a scaffold that allows cell to cell contacts in three dimensions.

Thus, the adherent material of the 3D aspect of the present invention is configured for 3D culturing thereby providing a growth matrix that substantially increases the available attachment surface for the adherence of the adherent stromal cells so as to mimic the infrastructure of the tissue (e.g., placenta).

For example, for a growth matrix of 0.5 mm in height, the increase is by a factor of at least from 5 to 30 times, calculated by projection onto a base of the growth matrix. Such an increase by a factor of about 5 to 30 times, is per unit layer, and if a plurality of such layers, either stacked or separated by spacers or the like, is used, the factor of 5 to 30 times applies per each such structure. When the matrix is used in sheet form, it may be non-woven fiber sheets, or sheets of open-pore foamed polymers. The thickness of the sheet can be about 50 to 1000 μm or more, there being provided adequate porosity for cell entrance, entrance of nutrients and for removal of waste products from the sheet. According to one embodiment, the pores have an effective diameter of 10 μm to 100 μm. Such sheets can be prepared from fibers of various thicknesses. In some embodiments, the fiber thickness or fiber diameter range from about 0.5 μm to 20 μm. For example, the fibers can be in the range of 10 μm to 15 μm in diameter.

The structures of the invention may be supported by, or bonded to, a porous support sheet or screen providing for dimensional stability and physical strength. Such matrix sheets may also be cut, punched, or shredded to provide particles with projected area of the order of about 0.2 mm2 to about 10 mm2, with the same order of thickness (about 50 to 1000 μm).

The adherent surface may have a shape selected from the group consisting of squares, rings, discs, and cruciforms. In some embodiements, culturing is effected in a 3D bioreactor.

Examples of such bioreactors include, but are not limited to, a plug flow bioreactor, a continuous stirred tank bioreactor and a stationary-bed bioreactor. As shown Example 1 of the Examples section, a three dimensional (3D) plug flow bioreactor (as described in U.S. Pat. No. 6,911,201) is capable of supporting the growth and prolonged maintenance of adherent stromal cells. In this bioreactor, adherent stromal cells are seeded on porrosive carriers made of a non woven fabric matrix of polyester, packed in a glass column, thereby enabling the propagation of large cell numbers in a relatively small volume.

Other 3D bioreactors can be used with the present invention. Another non-limiting example is a continuous stirred tank bioreactor, where a culture medium is continuously fed into the bioreactor and a product is continuously drawn out, to maintain a time-constant steady state within the reactor. A stirred tank bioreactor with a fibrous bed basket is available for example at New Brunswick Scientific Co., Edison, N.J. Other examples include, but are not limited to, a stationary-bed bioreactor, an air-lift bioreactor, [where air is typically fed into the bottom of a central draught tube flowing up while forming bubbles, and disengaging exhaust gas at the top of the column], a cell seeding perfusion bioreactor with Polyactive foams [as described in Wendt, D. et al., Biotechnol Bioeng 84: 205-214, (2003)], and tubular poly-L-lactic acid (PLLA) porous scaffolds in a Radial-flow perfusion bioreactor [as described in Kitagawa et al., Biotechnology and Bioengineering 93(5): 947-954 (2006)]. Other bioreactors which can be used in accordance with the present invention are described in U.S. Pat. Nos. 6,277,151, 6,197, 575, 6,139,578, 6,132,463, 5,902,741 and 5,629,186.

The matrix used in the bioreactor can, for example, be in the form of a sheet. This sheet may be a non-woven fiber sheet, or a sheet of open-pore foamed polymers. The thickness of the sheet is, in some embodiments, from about 50 to 1000 μm or more, there being provided adequate porosity for cell entrance, entrance of nutrients and for removal of waste products from the sheet.

In some embodiments, cell seeding is effected 100,000-1,500,000 cells/mm at seeding.

In some embodiments, cells are harvested once reaching at least about 40% confluence, 60% confluence or 80% confluence while avoiding uncontrolled differentiation and senescence.

In some embodiment, culturing is effected for at least about 2 days, 3 days, 5 days, 10 days, 20 days, a month or even more. It will be appreciated that culturing in a bioreactor may prolong this period. Passaging may also be effected to increase cell number.

The cells of the present invention are adherent stromal cells (ASC). Thus, for example, the cells may have a spindle shape. Alternatively or additionally the cells may express a marker or a collection of markers (e.g. surface marker) typical to adherent stromal cells. Examples of adherent stromal cell surface markers (positive and negative) include but are not limited to CD105+, CD29+, CD44+, CD73+, CD90+, CD34−, CD45−, CD80−, CD19−, CD5−, CD20−, CD11B−, CD14−, CD19−, CD79−, HLA-DR−, and FMC7−. Other adherent stromal cell markers include but are not limited to tyrosine hydroxylase, nestin and H-NF.

Examples of functional phenotypes typical of adherent stromal cells include, but are not limited to, T cell suppression activity (don't stimulate T cells and conversely suppress same) and hematopoietic stem cell support activity.

In some embodiments, the adherent stromal cells do not differentiate. In alternative embodiments, the cells possess one or more of adipogenic, hepatogenic, osteogenic and neurogenic differentiation potential, but the cells do not possess all of these potentials. In one embodiment, the adherent stromal cells do not possess osteogenic differentiation potential. In one embodiment, the adherent stromal cells do not posses neurogenic differentiation potential. In one embodiment, the adherent stromal cells do not differentiate into cells of all three germ layers. Any of these structural or functional features can be used to qualify the cells of the present invention (see Examples 1-2 of the Examples section which follows).

In contrast to the adherent stromal cells of the invention, mesenchymal stem (stromal) cells are adherent cells that are capable of all of osteoblastic, adipogenic, and chondrogenic differentiation (Dominici et al., Cytotherapy 8(4):315-17 (2006)). Accordingly, in some of the various aspects and embodiments of the invention, the term "adherent stromal cell" or "ASC" excludes mesenchymal stem (stromal) cells.

As noted elsewhere, ASC may be prepared from a variety of tissue sources, including, but not limited to, placenta, adipose tissue, and bone marrow. When the cells are grown in 3D culture, they are referred to as "3D-ASC." When the cells are placental ASC produced in 3D culture, they may also be referred to as "PLX" cells.

In some embodiments, populations of cells according to the present teachings are characterized by a unique protein expression profile as is shown in Example 1 of the Examples section. Thus for example, adherent stromal cells of placenta, adipose tissue, or bone marrow generated according to the present teachings, are capable of expressing and/or secreting high levels of selected factors. For example, such cells express or secrete SCF, Flt-3, H2AF or ALDH X at least 2, 3, 4, 5, 6, 7, 8, 9, 10, 11, or even 12 fold higher than that expressed or secreted by adherent stromal cells of placenta, adipose tissue, or bone marrow grown in a 2D culture. Additionally or alternatively, population of cells of the present invention secrete or express IL-6, EEEF2, RCN2 or CNN1 at a level least 2, 3, or 5 fold higher than that expressed or secreted by adherent stromal cells of placenta, adipose tissue, or bone marrow grown in a 2D culture. Additionally or alternatively, population of cells of the present invention are characterized by lower level of expression of various other proteins as compared to 2D cultured cells. Thus for example, secrete or express less than 0.6, 0.5, 0.25 or 0.125 of the expression level of Hnrphl, CD44 antigen isoform 2 precursor, Papss2 or rpL7a expressed or secreted by adherent stromal cells of placenta, adipose tissue, or bone marrow grown in a 2D culture.

In some embodiments, an isolated population of placental adherent stromal cells produced by culture under 3D conditions is less than about 1%, 5%, 10%, 15%, 20%, 25%, 30%, 35%, 40%, 45%, 50%, 55%, or 60% positive for the marker CD200, as detected by flow cytometry compared to an isotype control. In some embodiments, an isolated population of adherent stromal cells produced by culture under 3D conditions is less than about 1%, 5%, 10%, 20%, 30%, 40%, 50%, 60%, positive for the marker HLA-G, as detected by flow cytometry compared to an isotype control. In some embodiments, an isolated population of placental adherent stromal cells produced by culture under 3D conditions is less than about 1%, 5%, 10%, 20%, 30%, 40%, 50%, or 60% positive for the marker OCT-4, as detected by immunofluorescence compared to an isotype control.

While further reducing the present invention to practice the present inventors have realized that adherent stromal cells, and particularly 3D cultured adherent stromal cells (3D-ASCs), showed immunosuppressive activity. As is shown in Example 2 of the Examples section which follows, adherent stromal cells, and particularly 3D-ASCs, were found to suppress the immune reaction of human cord blood mononuclear cells in an MLR assay. Thus, the cells of the present invention may comprise biological activities which may be preferentially used in the clinic (e.g., T cell suppression activity, hematopoietic stem cell support activity).

The conditioned medium of the cells also comprise biological activities which may be preferentially used in the clinic (e.g., T cell suppression activity, hematopoietic stem cell support activity).

Thus, the present invention further envisages collection of conditioned medium and its use as is or following further steps of concentration, enrichment or fractionation using methods which are well known in the art. In some embodiments, a conditioned medium of the present invention is obtained from a high viability mid-log culture of cells.

As mentioned hereinabove, cells and conditioned media of the present invention are characterized by at least one adherent stromal cell phenotype and as such can be used in any research and clinical application which may benefit from the use of such cells. One such exemplary application is providing hematopoietic stem cell (HSC) support.

As used herein the phrase "stem cell" refers to a cell which is capable of self-renewal and which can differentiate to more than one cell type (i.e., is multipotent). A "hematopoietic stem cell" (HSC) is a stem cell which may, for example, be derived from cord blood (CB) or bone marrow (BM). An HSC can differentiate to multiple blood cell types. In the future, it may be possible to derive HSC from other sources, such as from embryonic stem cells.

Engraftment and initiation of hematopoiesis by transplanted HSCs depend on complex processes which include homing, following a gradient of chemokines across the endothelial cell barrier, to the bone marrow and lodging in the appropriate niches, while establishing physical contacts between transplanted cells, the ECM and the mesenchymal cells of the niches. All these processes involve a complex array of molecules, such as cytokines, hormones, steroids, extra cellular matrix proteins, growth factors, cell-to-cell interaction and adhesion proteins, and matrix proteins.

It is known that only 1-5% of transfused HSCs are detected in the recipient BM 2-3 days post transplantation [Kerre et al, J Immunol. 167:3692-8. (2001); Jetmore et al., Blood. 99:1585-93 (2002)]. Mesenchymal stem cells (MSCs) contribution to hematopoietic engraftment is in part by the inhibition of donor derived T cell production, which cause graft vs. host disease [GvHD, Charbord P., and Moore, K., Ann. K Y. Acad. ScL 1044: 159-167 (2005); Maitra B, et al., Bone Marrow Transplant. 33(6):597-604. (2004); U.S. Pat. Nos. 6,010,696; 6,555,374]; and part by providing a hematopoietic stem cell (HSC) support (i.e., sustaining and aiding the proliferation, maturation and/or homing of hematopoietic stem cells). Without being bound by theory, it is possible that the adherent stromal cells of the invention mediate their beneficial effects in patients with a compromised endogenous hematopoietic system at least in part by mechanisms similar to those of MSCs.

As shown in the Examples section which follows, placenta and adipose tissue-derived adherent stromal cells were surprisingly found to be supportive of HSC engraftment even after chemotherapy or irradiation. Adherent stromal cells from other sources, such as bone marrow, are therefore also potentially supportive of HSC engraftment.

Given these results it is conceivable that cells or media of the present invention may be used in any clinical application in which stem cell transplantation is used.

Thus, according to another aspect of the present invention there is provided a method of treating a medical condition (e.g., pathology, disease, syndrome) which may benefit from adherent stromal cell transplantation in a subject in need thereof.

As used herein the term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. The term "treating" refers to alleviating or diminishing a symptom associated with a cancerous disease. In one embodiment, treating cures, e.g., substantially eliminates, the symptoms associated with the medical condition. But unless specified that a cure is the intended end result, "treating" does not require "curing" the subject.

As used herein "a medical condition which may benefit from adherent stromal cell transplantation" refers to any medical condition which may be alleviated by administration of cells/media of the present invention.

The term or phrase "transplantation" refers to the introduction of cells to a subject.

As used herein the term "subject" refers to any subject (e.g., mammal), for example, a human subject.

The method of this aspect of the present invention comprises administering to the subject a therapeutically effective amount of the cells or media of the present invention (described hereinabove), thereby treating the medical condition which may benefit from adherent stromal cell transplantation in the subject.

Cells which may be administered in accordance with this aspect of the present invention include the above-described adherent stromal cells which may be cultured in either two-dimensional or three-dimensional settings.

In alternative embodiments, mesenchymal and nonmesenchymal partially or terminally differentiated derivatives of stem cells may be used, in combination with the adherent stromal cells. Methods of deriving lineage specific cells from the stem cells are well known in the art. See for example, U.S. Pat. Nos. 5,486,359, 5,942,225, 5,736,396, 5,908,784 and 5,902,741. The cells may be naive or genetically modified such as to derive a lineage of interest (see U.S. Pat. Appl. No. 20030219423).

The cells and media of the invention may be of autologous or non-autologous source (i.e., allogeneic or xenogeneic) of fresh or frozen (e.g., cryo-preserved) preparations.

Depending on the medical condition, the subject may be administered with additional chemical drugs (e.g., immunomodulatory, chemotherapy etc.) or cells.

Thus, for example, for improving stem cell engraftment (e.g., increasing the number of viable HSC in the recipient BM and optimally improve normal white blood cell count) the cells/media of the present invention may be administered prior to, concomitantly with or following HSC transplantation.

In some embodiments, the HSCs and adherent stromal cells do not share common HLA antigens. In other embodiments, the HSCs and adherent stromal cells share common HLA antigens.

In some embodiments, the HSCs and adherent stromal cells are from a single individual. Alternatively, the HSCs and adherent stromal cells are from different individuals.

In some embodiments, the number of viable HSC in the recipient BM is increased at least in part because the adherent stromal cells/media mitigate the death of endogenous HSC. Alternatively, or in addition, the number of viable HSC in the recipient BM is increased at least in part because of expansion of endogenous cells of the recipient following administration of the cells/media of the present invention.

It has been surprisingly found that the adherent stromal cells described herein, for example, the 3D-adherent stromal cells, in certain instances may play an important stimulatory role in enhancing and supporting the re-population of the endogenous hematopoietic system of the recipient in need thereof. Administration of the adherent stromal cells to an immune deficient or an immune compromised subject resulted in an elevated endogenous hematopoiesis. Thus, the below results and findings provide additional clinical benefits of using adherent stromal cells for their now discovered immunologic properties including rebuilding the endogenous hematopoietic system.

Two attributes of the disclosed 3D adherent stromal cells (3D-ASC) make them especially appropriate for mass treatment of radiation exposure in a population that may be caused by a catastrophe such as an accident in a nuclear plant or a terrorist attack. First, the low immunogenicity of the 3D-ASC cells produced in the disclosed method and 3D bioreactor allow using the same type of cells for all patients, without having to specifically match the administered cells to the patients individually during the immediate period after exposure. Second, the 3D bioreactor allows mass production of the 3D-ASC cells, thereby providing a sheer quantity of cells that enables large scale treatment.

As shown in the Examples, endogenous hematopoiesis is induced by administration of ASC, including 3D-ASC and PLX cells. In the examples, expression of endogenous CD45 demonstrates a sharp increase indicating an upregulation of the endogenous hematopoietic cell proliferation and/or repopulation.

This hematopoiesis-promoting effect on the recipient is an unrecognized function of these ASC, including 3D-ASC and PLX, occurring even without co-transplantation with umbilical cord blood or HSCs.

Thus, as described in more detail elsewhere, the adherent stromal cells, including 3D-ASC and PLX, can be used to treat immune deficient subjects or recipients, for example, to mitigate acute radiation sickness. In particular, the subjects (or recipients) can be those which were exposed to lethal or sub-lethal irradiation. Moreover, the subjects (or recipients) can be those which were pretreated with chemotherapy.

Administration of adherent stromal cells, including 3D-ASC and PLX, can serve as a supportive treatment to improve hematopoietic recovery following radiation and chemotherapy. The ability of the 3D-adherent stromal cells to enhance hematopoietic stem and/or progenitor recovery may result from the 3D-adherent stromal cell ability to secrete HSC supporting cytokines that may improve the self-renewal and proliferation ability of the haematopoietic cells, or from the ability of those cells to rebuild the damaged hematopoietic microenvironment needed for the proliferation of the HSCs.

The use of adherent stromal cells as a treatment to re-populate the endogenous hematopoietic system shows promising advantages over transplanting bone marrow (BM) cells and human umbilical cord blood (HUCB) cells. In general, adherent stromal cells do not require tissue typing and matching to the recipient. In contrast, BM and HUCB require tissue matching which substantially limits their availability. Moreover, adherent stromal cells as demonstrated herein can be mass produced and provide a sustainable source of cells.

As described in more detail below, the cells/media of the invention may also be administered without HSC transplantation and yet still effect an increase in the number of viable HSC in the recipient BM. Likewise, the cells/media of the invention may be administered to a subject following exposure to harmful levels of radiation to mitigate the effects of exposure to the radiation, even though exogenous hematopoietic stem cells are not administered to the subject. Similarly, the cells/media of the invention may be administered to a subject receiving chemotherapy to mitigate the effects of the chemotherapy, even though exogenous hematopoietic stem cells are not administered to the subject.

Accordingly, in one aspect the invention provides methods for treating a subject following exposure to harmful levels of radiation, comprising administering to the subject a therapeutically effective amount of adherent stromal cells to mitigate effects of exposure to the radiation. In some embodiments of this aspect, exogenous hematopoietic stem cells are not administered to the subject.

In yet another aspect, the invention provides methods for treating a subject receiving chemotherapy, comprising administering to the subject a therapeutically effective amount of adherent stromal cells to mitigate effects of the chemotherapy. In some embodiments of this aspect, exogenous hematopoietic stem cells are not administered to the subject.

In still another aspect, the invention provides methods for treating a subject suffering from a compromised endogenous hematopoietic system, comprising administering to the subject a therapeutically effective amount of adherent stromal cells for inducing repopulation of endogenous hematopoietic cells and/or for mitigating reduction in the number of endogenous hematopoietic cells in the endogenous hematopoietic system. In some embodiments of this aspect, exogenous hematopoietic stem cells are not administered to the subject.

The terms "endogenous", "endogenous hematopoietic cell(s)" or "endogenous hematopoietic system" as used herein refers to hematopoietic cells naturally found or originating within a recipient mammal, human (i.e. the treated subject; the recipient being treated with the adherent stromal cells. These hematopoietic cells are naturally found or originating within a recipient mammalian body and are produced by the recipient body; i.e., they are not exogenous hematopoietic cells.

In some embodiments, these adherent stromal cells can be any of the adherent stromal cells disclosed herein. For example, the adherent stromal cells can be from placenta, adipose tissue, or bone marrow.

The terms "exogenous", "exogenous source" or "exogenous donor" as used herein refers to cells originating from an outside source with respect to the recipient or otherwise treated subject. That is, an exogenous cell is a cell derived from a donor other than the recipient subject.

In some embodiments, the exogenous adherent stromal cells are obtained from an allogeneic or xenogeneic donor(s). In some embodiments, the adherent stromal cells are administered without allogeneic or xenogeneic HSCs transplantation. In some embodiments, the adherent stromal cells are administered as primary treatment for the rebuilding or repopulating of the endogenous hematopoietic system.

It will generally be readily apparent whether cells/tissue is endogenous or exogenous relative to the recipient because it will be known whether the initial source of the cells/tissue was the recipient (endogenous) or another source (exogenous). Nevertheless, whether cells or tissue is endogenous or exogenous with respect to the recipient can also be determined by genotyping. The term "genotype" refers to a 5' to 3' sequence of nucleotide pairs found at a set of one or more polymorphic sites in a locus on a pair of homologous chromosomes in an individual or cells. As used herein, genotype includes a full genotype. By way of non-limiting illustration, the term full genotype includes sequence of nucleotide pairs found at a plurality of polymorphic sites on a pair of homologous chromosomes in a recipient individual.

The term "irradiation" refers to a situation or the condition of exposure to radiation of the recipient mammal, human, or treated subject. In some embodiments, the radiation is ionizing radiation. In other embodiments, the radiation is non-ionizing radiation. Radiation includes electromagnetic radiation, which includes X-rays and/or gamma rays. The term radiation also encompasses radioactive radiation. The term also encompasses radiation resulting from the decay of radioactive elements.

In some embodiments, the radiation is ionizing radiation. In one embodiment, the ionizing radiation is clinical ionizing radiation; that is, ionizing radiation produced in a hospital or clinic for at least one therapeutic purpose, such as treatment of a cancer or tumor. In another embodiment, the ionizing radiation is from a radioactive isotope. In another embodiment, the radiation is from nuclear fission or fusion.

In one embodiment, the radiation is not solar radiation.

The term "irradiated" vis-à-vis the recipient mammal, human, or subject means the recipient mammal, human, or subject has been exposed to radiation. The effects of irradiation may manifest in any of several ways, such as those described below. In some embodiments, irradiation means exposure to radiation that compromises the endogenous hematopoietic system. In some embodiments, the compromised hematopoietic system is manifested by a reduced hematopoietic cell count or number. In some embodiments, the compromised hematopoietic system is manifested by a reduced number of endogenous hematopoietic CD45+ expressing cells. In some embodiments, the compromised hematopoietic system is manifested by a reduced number of platelets. In these embodiments, the subject may exhibit bleeding. In some embodiments, the compromised hematopoietic system is manifested by a reduced number of red blood cells. In these embodiments, the subject may exhibit anemia.

In some embodiments, irradiation means exposure to radiation that produces gastrointestinal symptoms. In these embodiments, the gastrointestinal symptoms include, but are not limited to, one or more of nausea, vomiting, loss of appetite, or abdominal pain.

In some embodiments, irradiation means exposure to radiation that produces neurological symptoms. In these embodiments, neurological symptoms include, but are not limited to, one or more of dizziness, headache, or decreased level of consciousness.

In some embodiments, irradiation means exposure to radiation that produces cutaneous symptoms. In these embodiments, cutaneous symptoms include, but are not limited to, reddening, blistering, ulceration, hair loss, damaged sebaceous and/or sweat glands, atrophy, fibrosis, decreased or increased skin pigmentation, or necrosis.

Radiation is "harmful" when it causes one or more effect in a subject that is undesirable, such as a one or more of a compromised hematopoietic system, gastrointestinal symptoms, or neurological symptoms, whether or not the radiation also produces an intended or even beneficial effect. Accordingly, harmful irradiation encompasses therapeutic irradiation, as used in cancer therapy.

The term "chemical exposure" encompasses exposure to any cytotoxic substance compromising the endogenous hematopoietic system of the recipient mammal, human, or subject. One example of a chemical exposure is "chemotherapy." In some embodiments, chemotherapy encompasses a cytotoxic treatment regimen of the recipient mammal, human or treated subject. Thus in one embodiment, chemotherapy refers to anti-neoplastic drugs or compounds used to treat cancer or the combination of these drugs. In some embodiments, the recipient mammal, human, or subject receives chemotherapy in addition to radiation therapy. In other embodiments, the recipient mammal, human, or subject is exposed to harmful chemicals outside of a clinical setting, as may occur in a terrorist attack, in an accident at a chemical plant or research laboratory, an accident in shipping of chemicals, or other accidental exposure. In some embodiments, damage or compromise to the endogenous hematopoietic system of the recipient mammal, human, or treated subject is caused by exposure to a cytotoxic substance which is a chemical substance(s) used as chemical warfare for their toxic properties.

The effects of chemical exposure or chemotherapy may manifest in any of several ways. In some embodiments, the damage to the hematopoietic system is manifested by a reduced hematopoietic cell count or number. In some embodiments, the compromised hematopoietic system is manifested by a reduced number of endogenous hematopoietic CD45+ expressing cells. In some embodiments, the compromised hematopoietic system is manifested by a reduced number of platelets. In these embodiments, the subject may exhibit bleeding. In some embodiments, the compromised hematopoietic system is manifested by a reduced number of red blood cells. In these embodiments, the subject may exhibit anemia.

In some embodiments, the chemotherapy produces gastrointestinal symptoms. In these embodiments, the gastrointestinal symptoms include, but are not limited to, one or more of nausea, vomiting, loss of appetite, or abdominal pain.

In some embodiments, chemotherapy produces neurological symptoms. In these embodiments, neurological symptoms include, but are not limited to, one or more of dizziness, headache, or decreased level of consciousness.

The term "compromised endogenous hematopoietic system" means a condition which may benefit from adherent stromal cell administration (or treatment). By way of non-limiting example, the condition requires re-population and/or promotion of the endogenous hematopoietic system. Another non-limiting example includes a condition comprising low number of hematopoietic cells (such as CD45 expressing cells) in the BM of the treated subject. The skilled physician would know to determine reduced number of hematopoietic cells relative to a normal level of hematopoietic cells.

The term or phrase "transplantation" refers to the introduction of cells to a subject. The cells can be derived from the recipient or from an allogeneic or xenogeneic donor.

In some embodiments the subject will be further treated to avoid rejection of non-autologous cells. These treatments may include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al, Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In some of the methods described herein, the cells or media can be administered either per se or as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, for example, in physiologically compatible buffers such as Hank's solution, Ringer's solution, or physiological salt buffer. For transmucosal administration, penetrants appropriate to the barrier to be permeated are used in the formulation. Such penetrants are generally known in the art.

For any preparation used in the methods of the invention, the therapeutically effective amount or dose can be estimated initially from in vitro and cell culture assays. A dose is generally formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et ah, 1975, in "The Pharmacological Basis of Therapeutics", Ch. 1 p. 1). For example, a chemotherapy patient can be monitored symptomatically for improved gastrointestinal symptoms indicating positive response to treatment.

For injection, the active ingredients of the pharmaceutical composition may be formulated in aqueous solutions, for example, in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

In some embodiments, the cells or medium of the invention are administered by intravascular injection, intramuscular injection, intraperitoneal injection, subcutaneous injection, intratracheally, or by inhalation. In one embodiment, adherent stromal cells are administered by intravenous injection. In one embodiment, adherent stromal cells are administered by intramuscular injection.

Cells or medium of the invention may administered only once, or they may be administered at least two, three, four, five, or up to ten times or more. In the case of multiple administrations, the individual administrations may all be via the same route, or different routes of administration may be utilized for different administrations during the course of therapy.

Cells or medium of the invention may be administered before, during, after or in combination of times with respect to exposure to radiation or chemicals. When the administration comprises at least two administrations, each administration may be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days apart. Alternatively, each administration may be about one, two, three, four, five, or six months apart.

Dosing may be initiated on the day of exposure to radiation or chemicals. Dosing may begin about 1, 2, 3, 4, 5, 6, 7, 8, 9, or 10 days following exposure. Dosing may continue while exposure the radiation or chemicals is ongoing. In some embodiments, dosing begins about 1, 2, 3, 4, 5, 6, 7, 8, 9, or 10 days before exposure, for example, before a schedule radio or chemotherapy. When dosing begins prior to exposure, it may begin again on the day of or following exposure, as noted above.

In one exemplary dosing regimen, adherent stromal cells are administered intramuscularly at least two times and are administered 1, 2, 3, 4, or 5 days apart. Other exemplary dosing regimen are provided in the Examples.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated chemotherapy patient will be administered with an amount of cells which is sufficient to alleviate the symptoms of the chemotherapy, based on the monitoring indications.

In one embodiment, following transplantation, the cells of the present invention survive in the patient for a period of time such that a therapeutic effect is observed.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U. S; Food and Drug Administration for prescription drugs or of an approved product insert.

Some aspects of the invention comprise a kit. In one embodiment, the kit is for treating a subject following exposure to harmful levels of radiation, to mitigate the effects of exposure to the radiation. In one embodiment, the kit is for treating a subject receiving chemotherapy to mitigate effects of the chemotherapy. In one embodiment, the kit is for treating a subject suffering from a compromised endogenous hematopoietic system.

In some of these embodiments, the kit may comprise at least one therapeutically effective amount of adherent stromal cells in a sterile package, and instructions for administration of a therapeutically effective amount of the cells. The kit may further comprise instructions for administration within a specified period after the exposure to radiation or chemicals.

In one embodiment the kit comprises a first therapeutically effective amount of adherent stromal cells in a first sterile package, for administration within a specified period after the exposure to radiation or chemotherapy, for inducing repopulation of endogenous hematopoietic cells and/or mitigating reduction in the number of endogenous hematopoietic cells in the endogenous hematopoietic system, a second therapeutically effective amount of adherent stromal cells, optionally provided together with hematopoietic stems cells, in a second sterile package, for administration after a matching period following the exposure, for further enhancement of repopulation of endogenous hematopoietic cells in the endogenous hematopoietic system, and instructions for administration of the first and second therapeutically effective amounts.

In some embodiments, the therapeutically effective amount induces, or further induces, repopulation of endogenous hematopoietic cells in the subject. In some embodiments, the chemical exposure is chemotherapy. In some embodiments, the radiation is ionizing radiation. In one embodiment, the adherent stromal cells are adherent stromal cells from placenta, adipose tissue, or bone marrow that have been cultured under 3D conditions.

The sterile packages may be configured to enable administration by intravascular injection, intramuscular injection, intraperitoneal injection, intrathecal injection, subcutaneous injection, or inhalation, independently of each other and possibly adaptable to the subject. Different kits with different packages may be used according to the administration method.

Some embodiments of the invention comprise a use of adherent stromal cells for the manufacture of a medicament for use in the treatment at a specified dosage regime, of a compromised endogenous hematopoietic system due to exposure to radiation or chemicals. For example, the specified dosage regime may comprise a therapeutically effective amount of adherent stromal cells administered within ten days after the exposure to radiation or chemicals. In another example, the specified dosage regime may comprise a first therapeutically effective amount of adherent stromal cells within ten days after the exposure to radiation or chemicals and at least one second therapeutically effective amount of adherent stromal cells after a second specified period. In some embodiments, the therapeutically effective amount induces, or further induces, repopulation of endogenous hematopoietic cells in the subject. In some embodiments, the chemical exposure is chemotherapy. In some embodiments, the radiation is ionizing radiation. In one embodiment, the adherent stromal cells are adherent stromal cells from placenta, adipose tissue, or bone marrow that have been cultured under 3D conditions.

In those embodiments involving at least one second therapeutically effective amount, the second therapeutic amount optionally may comprise matched allogeneic cord blood or bone marrow cells. These embodiments may optionally include a (second) specified period that may be a matching period of matching the cells to the subject. For example, the first therapeutically effective amount may be administered within two days after the exposure, and the matching period may be at least four days.

The at least one second therapeutically effective amount may be administered, for example, every week, every month, every one to four months, or every four to six months following the exposure.

The first and the optional at least one second therapeutically effective amounts may be administered by intravascular injection, intramuscular injection, intraperitoneal injection, subcutaneous injection, or inhalation.

In another aspect, the present invention is directed to a method for treating a subject suffering from a hematopoietic disease, disorder, deficiency or syndrome which causes a compromised endogenous hematopoietic system; the method comprising administering a therapeutically effective amount of adherent stromal cells.

The present invention also relates to a method for treating a subject suffering from a compromised endogenous hematopoietic system, comprising administering to the subject a therapeutically effective amount of adherent stromal cells for inducing repopulation of endogenous hematopoietic cells and/or mitigating reduction in the number of endogenous hematopoietic cells in the endogenous hematopoietic system.

In yet another aspect, the present intention relates to a pharmaceutical composition comprising a therapeutically effective amount of adherent stromal cells. In one embodiment, the pharmaceutical composition comprises a therapeutically effective amount of adherent stromal cells for treating a subject following exposure to harmful levels of radiation to mitigate effects of exposure to the radiation. In another embodiment, the pharmaceutical composition comprises a therapeutically effective amount of adherent stromal cells for treating a subject receiving chemotherapy to mitigate effects of the chemotherapy. In one embodiment, the pharmaceutical composition comprises a therapeutically effective amount of adherent stromal cells for inducing repopulation of endogenous hematopoietic cells and/or mitigating reduction in the number of endogenous hematopoietic cells in the endogenous hematopoietic system in a subject suffering from a compromised hematopoietic system.

In one embodiment, the pharmaceutical composition does not further comprise exogenous hematopoietic stem cells.

In another aspect, the present invention relates to the use of a therapeutically effective amount of adherent stromal cells in the preparation of a pharmaceutical composition. In one embodiment, the pharmaceutical composition comprises a therapeutically effective amount of adherent stromal cells for use in treating a subject following exposure to harmful levels of radiation to mitigate effects of exposure to the radiation. In another embodiment, the pharmaceutical composition comprises a therapeutically effective amount of adherent stromal cells for use in treating a subject receiving chemotherapy to mitigate effects of the chemotherapy. In one embodiment, the pharmaceutical composition comprises a therapeutically effective amount of adherent stromal cells for use in inducing repopulation of endogenous hematopoietic cells and/or mitigating reduction in the number of endogenous hematopoietic cells in the endogenous hematopoietic system in a subject suffering from a compromised hematopoietic system.

In one embodiment, the pharmaceutical composition does not further comprise exogenous hematopoietic stem cells.

In some embodiments, the endogenous hematopoietic cells are produced by the subject's hematopoietic system. Thus, in some embodiments, the endogenous hematopoietic cell(s) are of the recipient mammal, for example, a human (i.e. the treated subject). The endogenous hematopoietic cell(s) can have the full genotype of the recipient mammal, for example, a human (i.e. the treated subject). In some embodiments, the genotype of the transplanted adherent stromal cells is different or not identical to the genotype of the endogenous hematopoietic cell(s) of the recipient.

In some embodiments, the repopulation of endogenous hematopoietic cells in the endogenous hematopoietic system comprises increasing the number of endogenous hematopoietic cells in the hematopoietic system of the subject.

In some embodiments, the repopulation of endogenous hematopoietic cells in the endogenous hematopoietic system comprises increasing the number of endogenous hematopoietic cells expressing the CD45 marker.

In some embodiments, the subject has been exposed to radiation.

In some embodiments, the subject is immune deficient due to chemotherapy. In some embodiments, the subject has been exposed to a cytotoxic substance which compromises the endogenous hematopoietic system.

In some embodiments, the origin of the adherent stromal cells is placenta, adipose tissue, or bone marrow.

In some embodiments, the adherent stromal cells were cultured under three dimensional culturing conditions supporting cell expansion. In some embodiments, the cultured adherent stromal cells secrete Flt-3 ligand, IL-6, and SCF into the culture medium.

In some embodiments, the origin of the adherent stromal cells is placenta, adipose tissue, or bone marrow, and the adherent stromal cells were cultured under three dimensional culturing conditions supporting cell expansion.

In some embodiments, the origin of the adherent stromal cells is placenta, adipose tissue, or bone marrow, and the adherent stromal cells were cultured under three dimensional culturing conditions supporting cell expansion in the absence of differentiation.

The adherent stromal cells can be derived from the treated subject or from an allogeneic or xenogeneic donor.

By way of non-limiting example, any of the methods of the present invention can be used without exogenous HSC transplantation. Accordingly, in some embodiments of the various aspects, there is provided the proviso that the method does not comprise administering exogenous HSC to the patient or subject.

In some embodiments, the compromised endogenous hematopoietic system is manifested by a reduced hematopoietic cell count or number. In some embodiments, the compromised hematopoietic system is manifested by a reduced number of endogenous hematopoietic CD45 expressing cells.

Without wishing to be bound by theory, it is believed that the adherent stromal cells generally act by supporting repopulation of the hematopoietic system and/or by mitigating reduction in the number of endogenous hematopoietic cells of the treated subject. Thus, as described, in some embodiments, the adherent stromal cells act by increasing the endogenous hematopoietic cell expression, proliferation and/or differentiation in the subject in need thereof. In other embodiments, the adherent stromal cells act by supporting engraftment of exogenous hematopoietic stem cells in the subject. In other embodiments, the therapeutic effect of the administered adherent stromal cells is to treat a subject exposed to radiation or a chemical agent or to improve one or more symptoms of exposure to radiation or a chemical agent in an exposed subject.

Accordingly, in another aspect, the invention also provides methods of treating a subject exposed to radiation or chemicals comprising administering to the exposed subject a therapeutically effective amount of adherent stromal cells. In some embodiments, the treatment prolongs the survival of a subject, for example, a subject exposed to a lethal dose of radiation. By lethal dose is meant an exposure of about 2-8 Gy ionizing radiation (IR) (generally lethal within about 2-4 weeks), of about 8-30 Gy IR (generally lethal within about 2 days to 2 weeks), or of greater than about 30 Gy IR (generally lethal within about 1-2 days). The invention also provides, in additional aspects, methods of reducing symptoms associated with exposure to radiation, for example, ionizing radiation, or symptoms associated with exposure to toxic chemicals, such as following chemotherapy, comprising administering to the exposed subject a therapeutically effective amount of adherent stromal cells. In these embodiments, symptoms include, but are not limited to, nausea, vomiting, diarrhea, headache, fever, weight loss, neurological symptoms (e.g., cognitive impairment, seizures, tremor, ataxia, lethargy), leukopenia, anemia, thrombocytopenia, fatigue, weakness, purpura, hemorrhage, epilation, and shock. The symptoms may also manifest as damage to one or more of the respiratory system, nervous system, gastrointestinal system, cardiovascular system, the skin, or the renal system, as previously noted.

In some of the various embodiments of these aspects of the invention, the timing of the administration, the number of doses, and the route(s) of administration include those described for the various aspects involving repopulation of the hematopoietic system and/or involving mitigating reduction in the number of endogenous hematopoietic cells.

Figure 15:
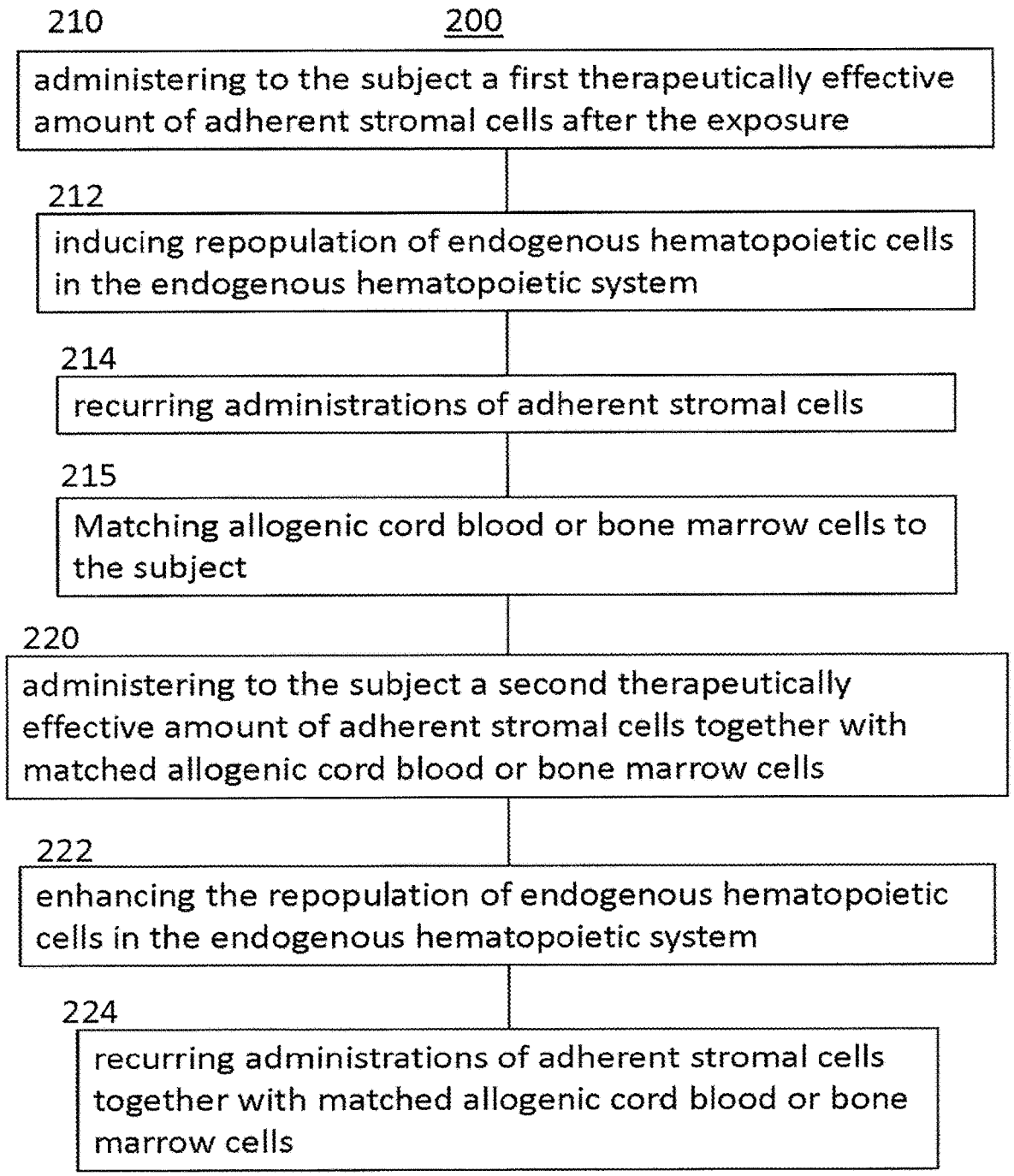
FIG. 15 is a high level flowchart illustrating a method 200 of treating a subject suffering from a compromised endogenous hematopoietic system due to exposure to radiation or chemotherapy.

FIG. 15 is a high level flowchart illustrating a method 200 of treating a subject suffering from a compromised endogenous hematopoietic system due to exposure to radiation or toxic chemicals, such as chemotherapy.

Method 200 comprises administering to the subject a first therapeutically effective amount of adherent stromal cells within a specified period (e.g. within 10 days, for example within 7-10 days, within 5-6 days, within 3-4 days, within 1-2 days, or within about 1 day) after the exposure to radiation or chemotherapy (stage 210), for inducing repopulation of endogenous hematopoietic cells and/or mitigating reduction in the number of endogenous hematopoietic cells in the endogenous hematopoietic system (stage 212), and administering to the subject a second therapeutically effective amount of adherent stromal cells together with matched allogeneic cord blood or bone marrow cells after a matching period (e.g. 4-21 days) following the exposure (stage 220), for further enhancement the repopulation of endogenous hematopoietic cells in the endogenous hematopoietic system (stage 222).

Method 200 may further comprise recurring administrations of either adherent stromal cells alone (stage 214) or adherent stromal cells together with matched allogeneic cord blood or bone marrow cells (stage 224).

In embodiments, method 200 may comprise only recurring administrations (e.g. every week, every month, every 1-4 months, or every 4-6 months) of adherent stromal cells alone (stage 214) or only recurring administrations (e.g. every week, every month, every 1-4 months, or every 4-6 months) of adherent stromal cells together with matched allogeneic cord blood or bone marrow cells (stage 224).

Method 200 may further comprise matching the allogeneic cord blood or bone marrow cells to the subject (stage 215).

Administrations 210, 220 may be carried out by intravascular, intramuscular, intraperitoneal, subcutaneous injection, or inhalation administration. The administration method may be adapted to the subject and may differ between administrations 210, 220.

Figure 16:
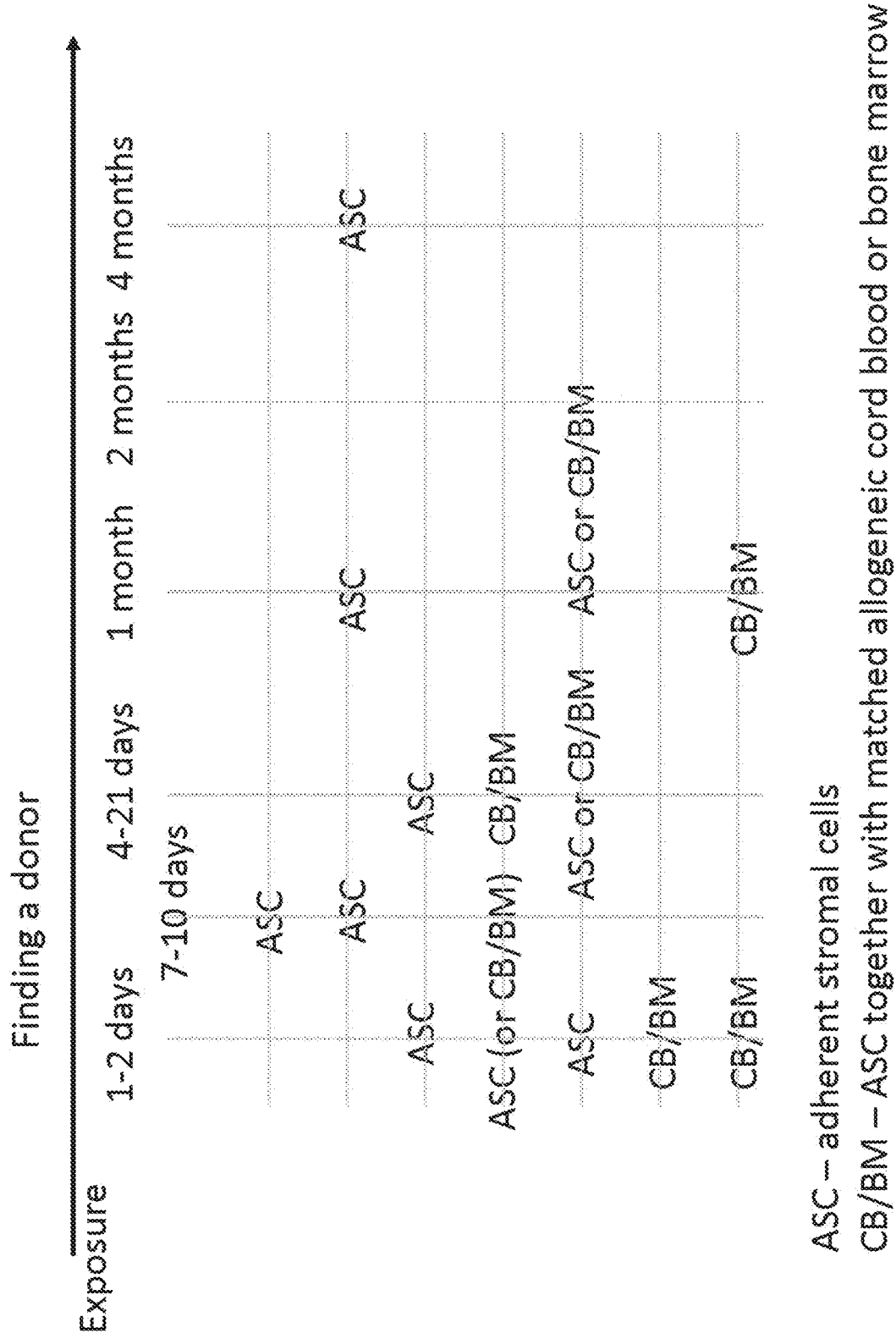
FIG. 16 illustrates some administration regimes, according to some embodiments of the invention. Administration of adherent stromal cells (ASC) and of ASC with matched allogeneic cord blood or bone marrow cells (CB/BM) is illustrated in respect to time after the exposure to radiation or chemotherapy.

FIG. 16 illustrates some administration regimes, according to some embodiments of the invention. Administration of adherent stromal cells (ASC) and of ASC with hematopoietic stem cells, for example, matched allogeneic cord blood or bone marrow cells (CB/BM), is illustrated in respect to time after the exposure to radiation or chemotherapy. The period of donor finding (that is, the "matching period") is typically 2-5 days, but may be longer or shorter, determining the possibility of administering allogeneic cord blood or bone marrow cells to support hematopoiesis. Generally speaking, the first immediate administration of ASC (optionally including CB/BM) protects against acute toxicity, while the following administrations of either ASC or ASC with CB/BM supports hematopoiesis and may be carried out according to the subject's recovery.

The following list illustrates various dosage regimes applicable for the disclosed use and method.

1—Administrating adherent stromal cells (ASC) only, for example, within about 10 days, such as within 7-10 days, within 5-6 days, within 3-4 days, within 1-2 days, or within about 1 day after exposure.

2—Following 1—Additional administrations of adherent stromal cells only, for example, every week, every month, every 1-4 months, or every 4-6 months.

3—If a cord blood or bone marrow donor is found—Administrating adherent stromal cells and matched allogeneic cord blood or bone marrow cells (CB/BM) within about 10 days, such as within 7-10 days, within 5-6 days, within 3-4 days, within 1-2 days, or within about 1 day after the exposure.

4—Following 3—additional administrations of adherent stromal cells with or without matched allogeneic cord blood or bone marrow cells, for example every week, every month, every 1-4 months, or every 4-6 months.

5—Administrating adherent stromal cells only, at least twice within about 0-5 days after exposure, such as on days 1 and 5 after exposure, via an intramuscular route.

6—If a cord blood or bone marrow donor is found—Administrating adherent stromal cells and matched allogeneic cord blood or bone marrow cells within 2 days after the exposure 7—Following 5 or 6—Administrating matched allogeneic cord blood or bone marrow cells, 4-21 days after exposure (time required to find a cord blood or bone marrow donor).

8—After 7—Additional administrations of adherent stromal cells with or without matched allogeneic cord blood or bone marrow cells at need.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057'; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. L, ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. AU the information contained therein is incorporated herein by reference.

Example 1

Production and Culturing of Adherent Stromal Cells (ASC) from Bone Marrow, Placenta and Adipose Tissues Adherent stromal cells were cultured in a bioreactor system containing 3D carriers to produce 3D-ASC cells, characterized by a specific cell marker expression profile. Growth efficiency was tested through cell count. The differentiation capacity of these cells was tested by culturing in a differentiation medium.

Materials and Experimental Procedures

Bone Marrow Adherent Stromal Cells—

Bone marrow (BM) adherent stromal cells were obtained from aspirated sterna marrow of hematologically healthy donors undergoing open-heart surgery or BM biopsy. Marrow aspirates were diluted 3-fold in Hank's Balanced Salts Solution (HBSS; GIBCO BRL/Invitrogen, Gaithersburg Md.) and subjected to Ficoll-Hypaque (Robbins Scientific Corp. Sunnyvale, Calif.) density gradient centrifugation. Thereafter, marrow mononuclear cells (<1.077 gm/cm$^3$) were collected, washed 3 times in HBSS and resuspended in growth media [DMEM (Biological Industries, Beit Ha'emek, Israel) supplemented with 10% FCS (GIBCO BRL), 10$^{-4}$ M mercaptoethanol (Merck, White House Station, N.J.), Pen-Strep-Nystatin mixture (100 U/ml:100 ug/ml:1.25 un/ml; Beit Ha'Emek), 2 mM L-glutamine (Beit Ha'Emek)]. Cells from individual donors were incubated separately in tissue culture flasks (Corning, Acton, Mass.) at 37° C. (5% $CO_2$) with weekly change of culture media. Cells were split every 3-4 days using 0.25% trypsin-EDTA (Beit Ha'Emek). Following 2-40 passages, when reaching 60-80% confluence, cells were collected for analysis or for culturing in bioreactors.

Placenta Derived Adherent Stromal Cells—

Inner parts of a full-term delivery placenta (Bnei Zion medical center, Haifa, Israel) were cut under sterile conditions, washed 3 times with Hank's Buffer and incubated for 3 h at 37° C. with 0.1% Collagenase (1 mg/ml tissue; Sigma-Aldrich, St. Lewis, Mo.). Using gentle pipeting, suspended cells were then washed with DMEM supplemented with 10% FCS, Pen-Strep-Nystatin mixture (100 U/ml:100 ug/ml:1.25 un/ml) and 2 mM L-glutamine, seeded in 75 cm$^2$ flasks and incubated at 37° C. in a tissue culture incubator under humidified condition with 5% $CO_2$. Thereafter, cells were allowed to adhere to a plastic surface for 72 hours after which the media was changed every 3-4 days. When reaching 60-80% confluence (usually 10-12 days), cells were detached from the growth flask using 0.25% trypsin-EDTA and seeded into new flasks. Cultured cells were thereafter collected for analysis or for culturing in bioreactors.

Adipose Derived Adherent Stromal Cells—

Adherent stromal cells were obtained from human adipose tissue of liposuction procedures (Rambam Haifa, Israel). Adipose tissue was washed extensively with equal volumes of PBS and digested at 37° C. for 30 min with collagenase (20 mg/ml). Cells were then washed with DMEM containing 10% FCS, Pen-Strep-Nystatin mixture (100 U/ml:100 ug/ml:1.25 un/ml) and L-Glutamin and centrifuged at 1200 rpm for 10 min RT, resuspended with lysing solution (1:10; Biological Industries, Beit Ha'emek, Israel, in order to discard red-blood cells) centrifuged and resuspended with DMEM containing 10% FCS, Pen-Strep-Nystatin mixture (100 U/ml:100 ug/ml:1.25 un/ml) and L-Glutamin. Washed cells were then seeded in a sterile tissue culture medium flask at 3-10×10$^7$ cells/flask. At the next day cells were washed with PBS to remove residual RBC and dead cells. The cells were kept at 37° C. in a tissue culture incubator under humidified condition with 5% $CO_2$. The medium was changed every 3 to 4 days. At 60-80% confluence, the cells were detached from the growth flask using 0.25% trypsin-EDTA and seeded into new flasks. Following 2-40 passages, when cells reached 60-80% confluence, cells were collected for analysis or for culturing in bioreactors.

PluriX™ Plug Flow Bioreactor—

The PluriX™ Plug Flow bioreactor (Pluristem, Haifa, Israel; as illustrated in FIG. 1G, see also U.S. Pat. No. 6,911,201), was loaded with 1-100 ml packed 3D porrosive carriers (4 mm in diameter) made of a non woven fabric matrix of polyester. These carriers enable the propagation of large cell numbers in a relatively small volume. Glassware was designed and manufactured by Pluristem. The bioreactor was maintained in an incubator of 37° C., with flow rate regulated and monitored by a valve (6a in FIG. 1G), and peristaltic pump (9 in FIG. 1G). The bioreactor contains a sampling and injection point (4 in FIG. 1G), allowing the sequential seeding of cells. Culture medium was supplied at pH 6.7-7.4 from a reservoir (1 in FIG. 1G). The reservoir was supplied by a filtered gas mixture (2,3 in FIG. 1G), containing air/$CO_2$/$O_2$ at differing proportions, depending on cell density in the bioreactor. The $O_2$ proportion was suited to the level of dissolved $O_2$ at the bioreactor-exit, determined by a monitor (6 in FIG. 1G). The gas mixture was supplied to the reservoir via silicone tubes or diffuser (Degania Bet, Emek Hayarden, Israel). The culture medium was passed through a separating container (7 in FIG. 1G) which enables collection of circulating, nonadherent cells. Circulation of the medium was obtained by a peristaltic pump (9 in FIG. 1G). The bioreactor was further equipped with an additional sampling point (10 in FIG. 1G) and containers for continuous medium exchange.

Production of 3D-Adherent Stromal Cells (3D-ASC)—

Non-confluent primary human adherent stromal cell 2D cultures, grown as described above, were trypsinized, washed, resuspended in DMEM supplemented with 10% FBS, Pen-Strep-Nystatin mixture (100 U/ml:100 ug/ml:1.25 un/ml) and 2 mM L-glutamine, and seeded (10$^3$-10$^5$ cells/ml) via an injection point onto the 3D carriers in a sterile Plug Flow bioreactor (see FIG. 1G). Prior to inoculation, bioreactor was filled with PBS-Ca-Mg (Biological Industries, Beit Ha'emek, Israel), autoclaved (120° C., 30 min) and washed with Dulbecco's growth medium containing 10% heat-inactivated fetal calf serum and a Pen-Strep-Nystatin mixture (100 U/ml:100 ug/ml:1.25 un/ml). Flow was kept at a rate of 0.1-5 ml/min. Seeding process involved cease of circulation for 2-48 hrs, thereby allowing the cells to settle on the carriers. Bioreactor was kept under controlled temperature (37° C.) and pH conditions (pH=6.7-7.4); using an incubator supplied with sterile air and $CO_2$ as needed. Growth medium was replaced 2-3 times a week. Circulation medium was replaced with fresh DMEM media, every 4 hr to 7 days. At a density of 1×10$^6$-1×10$^7$ cells/ml (following 12-40 days of growth), total medium volume was removed from the bioreactor and bioreactor and carriers were washed 3-5 times with PBS. 3D-ASC cells were then detached from the carriers with Trypsin-EDTA; (Biological Industries, Beit Ha'emek, Israel; 3-15 minutes with gentle agitation, 1-5 times), and were thereafter resuspended in DMEM and cryopreserved.

3D-ASC Quality Biological Assays—

Cryopreserved 3D-ASC cells were thawed and counted. For cell viability evaluation, 2×10$^5$ cells were seeded in a 150 cm$^2$ tissue culture flask and their adherence capability and repopulation was evaluated within 7 days following seeding. Thereafter, the 3D-ASC membrane marker phenotype was analyzed using fluorescence monoclonal antibodies flow-cytometer (Beckman Coulter, Fullerton, Calif.).

Comparison Between the Cell Membrane Marker Profile of 3D and 2D Cultured Adherent Stromal Cells Using Flow Cytometery Assays 100,000-200,000 adherent stromal cells from 2D cultures and 3D flow system cultures were suspended in 0.1 ml of culture medium in a 5 ml tube and incubated (4° C., 30 min, dark conditions) with saturating concentrations of each of the following MAbs: FITC-conjugated anti-human CD90 (Chemicon International Inc. Temecula, Calif.), PE conjugated anti human CD73 (Bactlab Diagnostic, Ceasarea, Israel), PE conjugated anti human CD 105 (eBioscience, San Diego, Calif.), FITC conjugated anti human CD29 (eBioscience, San Diego, Calif.), Cy7-PE conjugated anti-human CD45 (eBiosience), PE-conjugated anti-human CD19 (IQProducts, Groningen, The Netherlands), PE conjugated anti human CD14 MAb (IQProducts), FITC conjugated anti human CD11b (IQProducts) and PE conjugated anti human CD34 (IQProducts) or with FITC conjugated anti human HLA-DR MAb (IQProducts). Following incubation the cells were washed twice in ice-cold PBS containing 1% heat-inactivated FCS, resuspended in 500 µl formaldehyde 0.5% and analyzed using the FC-500 flow-cytometer (Beckman Coulter, Fullerton, Calif.).

Comparison Between the Protein Profile of 3D and 2D Cultured Adherent Stromal Cells Using Mass Spectrometry Analysis—

2D and 3D derived culturing procedures ASCs were produced from the placenta as described above. Briefly, the 2D cultures were produced by culturing $0.3-0.75\times10^6$ cells in 175 cm$^2$ flasks for 4 days under humidified 5% $CO_2$ atmosphere at 37° C., until reaching 60-80% confluence. The 3D cultures were produced by seeding $2-10\times10^6$ cells/gram in a bioreactor containing 2000 carriers, and culturing for 18 days. Following harvesting, cells were washed (×3) to remove all the serum, pelleted and frozen. Proteins were isolated from pellets [using Tri Reagent kit (Sigma, Saint Louis, USA) and digested with trypsin and labeled with iTRAQ reagent (Applied Biosciences, Foster City, Calif.)], according to the manufacturers protocol. Briefly, iTRAQ reagents are non-polymeric, isobaric tagging reagents. Peptides within each sample are labeled with one of four isobaric, isotope-coded tags via their N-terminal and/or lysine side chains. The four labeled samples are mixed and peptides are analyzed with mass spectrometery. Upon peptide fragmentation, each tag releases a distinct mass reporter ion; the ratio of the four reporters therefore gives relative abundances of the given peptide in a sample, (information at: http://docs.appliedbiosystems.com/pebiodocs/00113379.pdf).

Proteomics analysis of 2D culture versus 3D culture of placenta derived ASCs was performed in the Smoler proteomic center (department of Biology, Technion, Haifa, Israel) using LC-MS/MS on QTOF-Premier (Waters, San Francisco, Calif.), with identification and analysis done by Pep-Miner software [Beer, I., et al., Proteomics, 4, 950-60 (2004)] against the human part of the nr database. The proteins analyzed were: heterogeneous nuclear ribonucleoprotein H1 (Hnrphl GeneBank Accession No. NP_005511), H2A histone family (H2AF, GeneBank Accession No. NP_034566.1), eukaryotic translation elongation factor 2 (EEEF2, GeneBank Accession No. NP_031933.1), reticulocalbin 3, EF-hand calcium binding domain (RCN2, GeneBank Accession No. NP 065701), CD44 antigen isoform 2 precursor (GeneBank Accession No. NPA00 1001389, calponin 1 basic smooth muscle (CNN1, GeneBank Accession No. NP_001290), 3 phosphoadenosine 5 phosphosulfate synthase 2 isoform a (Papss2, GeneBank Accession No. NP 004661), ribosomal protein L7a (rpL7a, GeneBank Accession No. NP_000963) and Aldehyde dehydrogenase X (ALDH X, GeneBank Accession No. P47738). Every experiment was done twice. Because of the nature of the analysis, every protein was analyzed according to the number of peptides of which appeared in a sample (2-20 appearances of a protein in each analysis)

Comparison Between Secreted Proteins in 3D and 2D Cultured Adherent Stromal Cells Using ELISA—

2D and 3D derived culturing procedures ASCs produced from the placenta, were produced as described above, with 3D cultures for the duration of 24 days. Conditioned media were thereafter collected and analyzed for Flt-3 ligand, IL-6, Trombopoietin (TPO) and stem cell factor (SCF), using ELISA (R&D Systems, Minneapolis, Minn.), in three independent experiments. Results were normalized for $1\times10^6$ cells/ml.

Results

The PluriX™ Bioreactor System Creates a Physiological-Like Microenvironment.

In order to render efficient culture conditions for adherent stromal cells, a physiological-like environment (depicted in FIG. 1A) was created artificially, using the PluriX Bioreactor (Pluristem, Haifa, Israel; carrier is illustrated in FIG. 1G and shown before seeding in FIG. 1B). As is shown in FIGS. 1C-1F, bone marrow produced 3D-ASC cells were cultured successfully and expanded on the 3D matrix, 20 days (FIGS. 1B-1C, magnified X 150 and 250 respectively) and 40 days (FIGS. 1C-1D, magnified X 350 and 500 respectively) following seeding.

Cells grown in the PluriX Bioreactor system were significantly expanded—Different production lots of placenta derived 3D-ASC cells were grown in the PluriX bioreactor systems. The seeding density was 13,300 cells/carrier (to a total of $2\times10^6$ cells). Fourteen days following seeding, cell density multiplied by 15 fold, reaching approximately 200,000 cells/carrier (FIG. 2), or $30\times10^6$ in a bioreactor of 150 carriers. In a different experiment, cells were seeded into the bioreactor at density of $1.5\times10^4$ cells/ml and 30 days following seeding the carriers contained an over 50-fold higher cell number, i.e. approx. $0.5\times10^6$ cells/carrier, or $0.5\times10^7$ cells/ml. The cellular density on the carriers at various levels of the growth column was consistent, indicating a homogenous transfer of oxygen and nutrients to the cells. The 3D culture system was thus proven to provide supporting conditions for the growth and prolonged maintenance of high-density mesenchymal cells cultures, which can be grown efficiently to an amount sufficient for the purpose of supporting engraftment and successful transplantation.

3D-ASCs Show Unique Membrane Marker Characteristics—

Figure 3A:
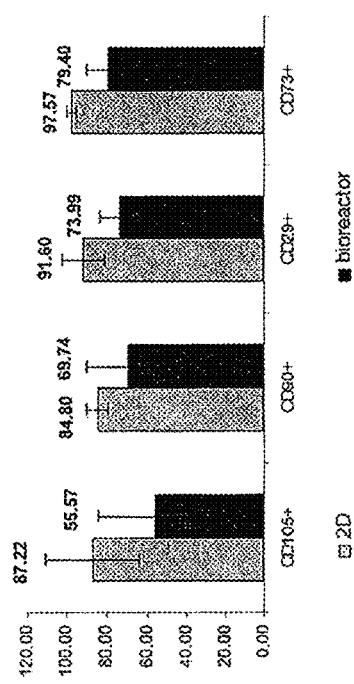
FIGS. 3A-3B are bar graphs depicting difference in expression levels of expressed membrane markers in placenta derived 3D-ASC (dark purple) as compared to membrane markers in placenta cells cultured in conventional 2D culture conditions (light purple). Adherent cells were grown for 4-6 weeks in flasks (2D) or for 2-3 weeks in the bioreactor system, on polystyrene carriers (3D). Following harvesting from either flasks or carriers, cells were incubated and bound to a panel of monoclonal antibodies (MAb), which recognize membrane markers characteristic of mesenchymal cells (FIG. 3A), or hematopoietic cells (FIG. 3B). Note the significantly higher expression of membrane markers in 2D cultured cells as shown for CD90, CD105, CD73 and CD29 membrane markers, compared to membrane markers expressed in 3D-cultured adherent cells, especially CD105 which showed 56% expression in 3D cultured cells vs. 87% in the 2D cultured cells (FIG. 3A). ASCs of both 2D and 3D cultures, did not express any hematopoietic membrane markers (FIG. 3B).
Figure 3B:
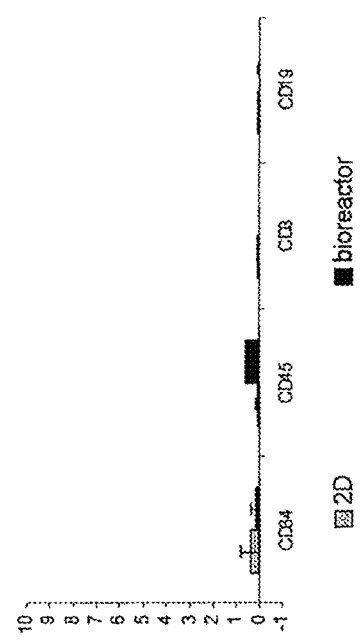

In order to define the difference in the secretion profile of soluble molecules and protein production, effected by the bone environment mimicking 3D culturing procedure, FACs analysis was effected. As is shown in FIG. 3A, FACS analysis of cell markers depict that 3D-ASCs display a different marker expression pattern than adherent stromal cells grown in 2D conditions. 2D cultured cells expressed significantly higher levels of positive membrane markers CD90, CD105, CD73 and CD29 membrane markers as compared to 3D cultured cells. For example, CD105 showed a 56% expression in 3D cultured cells vs. 87% in 2D cultured cells. ASCs of both 2D and 3D placenta cultures, did not express any hematopoietic membrane markers (FIG. 3B).

3D-ASCs Show a Unique Profile of Soluble Factors—

The hematopoietic niche includes supporter cells that produce an abundance of cytokines, chemokines and growth factors. In order to further define the difference between 2D and 3D cultured ASCs, the profile of the four main hematopoietic secreted proteins in the conditioned media of 2D and 3D ASC cultures was effected by ELISA. FIGS. 4A-4C show that cells grown in 3D conditions produced condition media with higher levels of Flt-3 ligand (FIG. 4A), IL-6 (FIG. 4B), and SCF (FIG. 4C), while low levels of IL-6, and close to zero level of Flt-3 ligand and SCF, were detected in the condition media of 2D cultures. Production of Trombopoietin (TPO) was very low and equal in both cultures.

3D-ASCs Show a Unique Protein Profile in Mass Spectrometry Analysis—

Figure 4D:
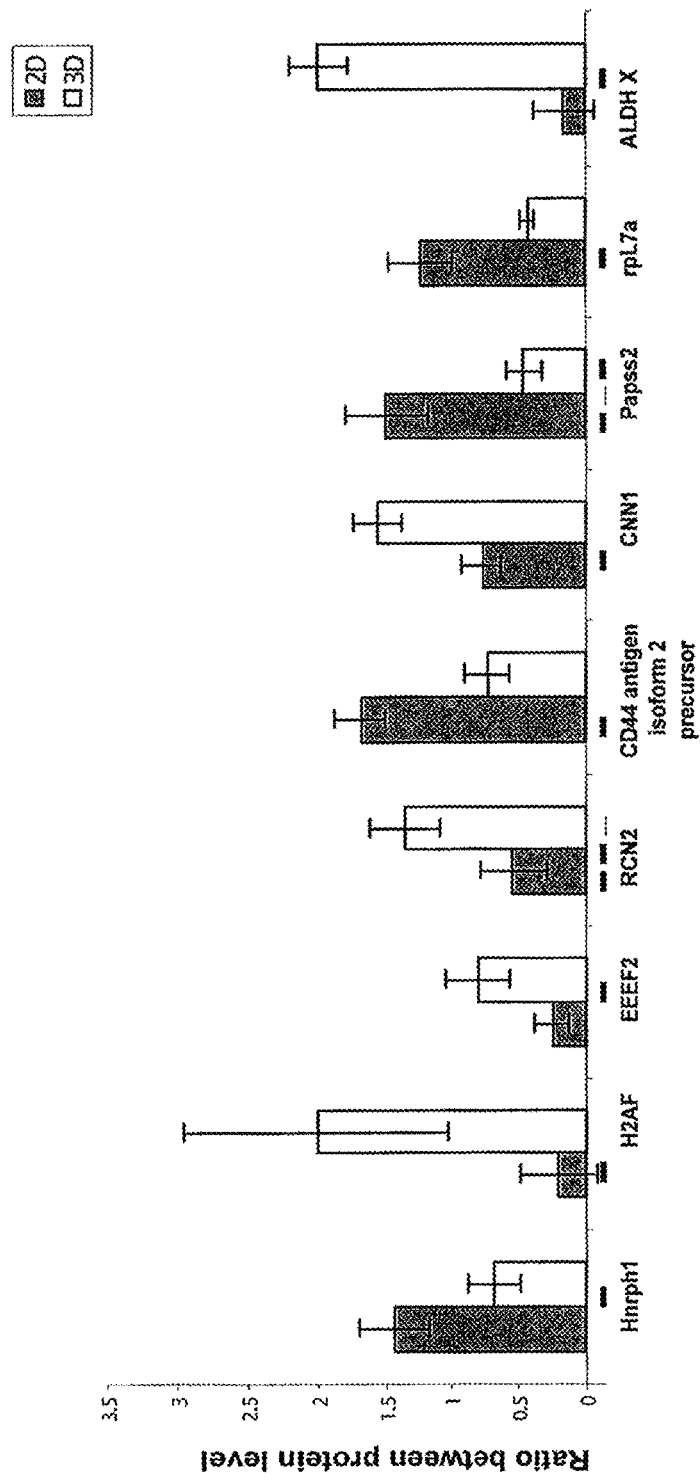

In order to further define the difference between 2D and 3D cultured ASCs, the protein profile of these cells was analyzed by mass spectrometry. FIG. 4D shows that 2D and 3D cultured ASCs show a remarkably different protein expression profile. As is shown in Table 1 below, 3D cultured cells show a much higher expression level of H2AF and ALDH X (more than 9 and 12 fold higher, respectively) and a higher level of the proteins EEEF2, RCN2 and CNN1 (ca. 3, 2.5 and 2 fold, respectively). In addition, 3D cultured cells show ca. half the expression levels of the proteins Hnrphl and CD44 antigen isoform 2 precursor and ca. a third of the expression levels of Papss2 and rpL7a.

TABLE 1

| | Protein level (relative to iTRAQ reporter group) | | | |
|---|---|---|---|---|
| | 2D adherent stromal cells | | 3D adherent stromal cells | |
| protein | Av | SD | Av | SD |
| Hnrphl | 1.434493 | 0.260914 | 0.684687 | 0.197928 |
| H2AF | 0.203687 | 0.288058 | 1.999877 | 0.965915 |
| EEEF2 | 0.253409 | 0.130064 | 0.799276 | 0.243066 |
| RCN2 | 0.54 | 0.25 | 1.34 | 0.26 |
| CD44 antigen isoform 2 precursor | 1.68 | 0.19 | 0.73 | 0.17 |
| CNN1 | 0.77 | 0.15 | 1.55 | 0.17 |
| Papss2 | 1.48352 | 0.314467 | 0.45627 | 0.137353 |
| rpL7a | 1.22 | 0.24 | 0.43 | 0.05 |
| ALDH X | 0.15847 | 0.22411 | 1.986711 | 0.212851 |

Example 2

The Suppression of Lymphocyte Response by 2D and 3D Cultured ASCs

Adherent stromal cells, and particularly 3D-ASCs, were found to suppress the immune reaction of human cord blood mononuclear cells in an MLR assay.

Materials and Experimental Procedures

Mixed Lymphocyte Reaction (MLR) Assay—

The immunosuppressive and immunoprivileged properties of 2D and 3D derived culturing procedures ASCs produced from the placenta, were affected by the MLR assay, which measures histocompatibility at the HLA locus, as effected by the proliferation rate of incompatible lymphocytes in mixed culturing of responsive (proliferating) and stimulating (unproliferative) cells. Human cord blood (CB) mononuclear cells ($2 \times 10^5$) were used as responsive cells and were stimulated by being co-cultured with equal amounts ($10^5$) of irradiated (3000Rad) human peripheral blood derived Monocytes (PBMC), or with 2D or 3D cultured adherent stromal cells, produced from the placenta, or a combination of adherent stromal cells and PBMCs. Each assay was replicated three times. Cells were co-cultured for 4 days in RPMI 1640 medium (containing 20% FBS under humidified 5% $CO_2$ atmosphere at 37° C.), in a 96-well plate. Plates were pulsed with 1 μC $^3$H-thymidine during the last 18 hr of culturing. Cells were then harvested over fiberglass filter and thymidine uptake was quantified with a scintillation counter.

Results

FIG. 7 shows the immune response of CB cells as represented by the elevated proliferation of these cells when stimulated with PBMCs, which, without being bound by theory, is probably associated with T cell proliferation in response to HLA incompatibility. However, a considerably lower level of immune response was exhibited by these cells when incubated with the adherent stromal cells of the present invention. Moreover, the CB immune response to PBMCs was substantially reduced when co-incubated with these adherent cells. Thus, ASCs were found to have the potential ability to reduce T cell proliferation of donor cells, typical of GvHD. Although both cultures, 2D and 3D, reduced the immune response of the lymphocytes, and in line with the other advantages of 3D-ASCs described hereinabove, the 3D ASCs were more immunosuppressive.

Example 3

Assessment of the Ability of Placenta Derived 3D-ASC to Improve HSC Engraftment

3D-ASC support of HSC engraftment was evaluated by the level of human hematopoietic cells (hCD45+) detected in sub lethally irradiated or chemotherapy pretreated immune deficient NOD-SCID mice.

Materials and Experimental Procedures

Isolation of CD34+ Cells—

Umbilical cord blood samples were taken under sterile conditions during delivery (Bnei Zion Medical Center, Haifa, Israel) and mononuclear cells were fractionated using Lymphoprep (Axis-Shield PoC As, Oslo, Norway) density gradient centrifugation and were cryopreserved. Thawed mononuclear cells were washed and incubated with anti-CD34 antibodies and isolated using midi MACS (Miltenyl Biotech, Bergish Gladbach, Germany). Cells from more than one sample were pooled for achieving the desired amount (50,000-100,000 cells).

Detection of Transplanted Cells in Irradiated Mice—

Seven week old male and female NOD-SCID mice (NOD-CB 17-Prkdcscid/J; Harlan/Weizmann Inst., Rehovot Israel) were maintained in sterile open system cages, given sterile diets and autoclaved acidic water. The mice were sub lethally irradiated (350 cGy), and thereafter (48 hr post irradiation) transplanted with 50,000-100,000 hCD34$^+$ cells, with or without additional ASCs ($0.5 \times 10^6$-$1 \times 10^6$) derived from placenta or adipose tissue (3-7 mice in each group), by intravenous injection to a lateral tail vein. Four to six weeks following transplantation the mice were sacrificed by dislocation and BM was collected by flushing both femurs and tibias with FACS buffer (50 ml PBS, 5 ml FBS, 0.5 ml sodium azide 5%). Human cells in the mice BM were detected by flow cytometry, and the percentage of the human and murine CD45 hematopoietic cell marker expressing cells in the treated NOD-SCID mice was effected by incubating cells with anti-human CD45-FITC (IQ Products, Groningen, The Netherlands). The lowest threshold for unequivocal human engraftment was designated at 0.5%.

Detection of Transplanted Cells in Mice Treated with Chemotherapy—

6.5 week old male NOD-SCID mice (NOD.CB17/Jh-kiHsd-scid; Harlan, Rehovot Israel), maintained as described hereinabove for irradiated mice, were injected intraperitoneally with Busulfan (25 mg/kg-for 2 consecutive days). Two days following the second Busulfan injection, mice were injected with CD34+ cells alone, or together with $0.5 \times 10^6$ ASCs, produced from the placenta. 3.5 weeks following transplantation, mice were sacrificed, and the presence of human hematopoietic cells was determined as described for irradiated mice.

Results

3D-ASC Improved Engraftment of HSC in Irradiated Mice—

Figure 5:
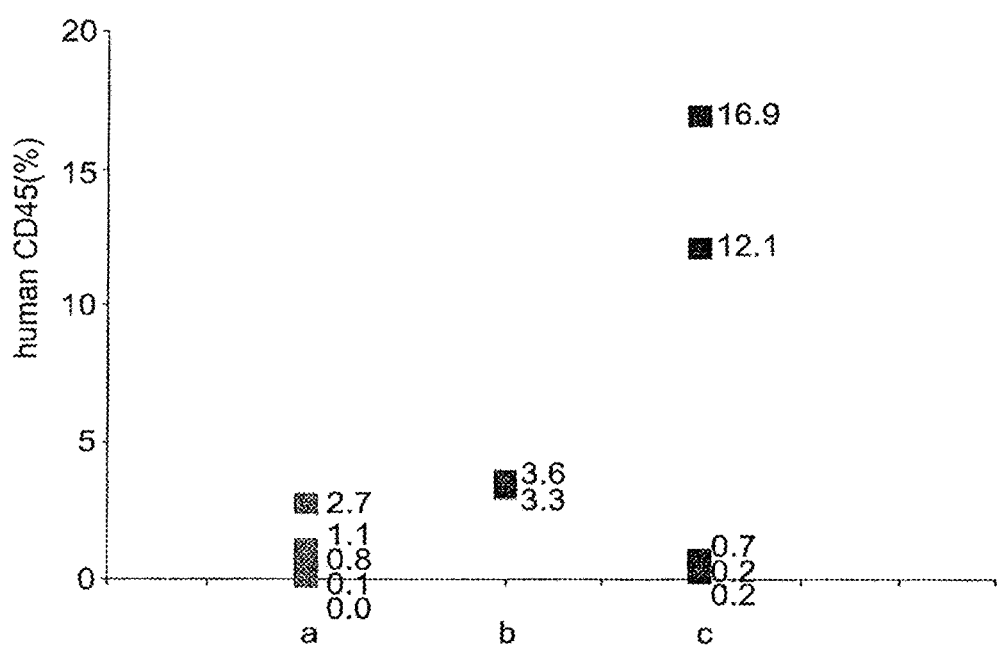
FIG. 5 is a graph depicting percentage of human CD45+ cells detected in bone marrow (BM) of NOD-SCID mice, treated with chemotherapy (25 mg/kg busulfan intraperitoneal injections for two consecutive weeks) 3.5 weeks following transplantation. CD34+ cells (100,000) purified from mononuclear cord blood derived cells, were transplanted alone (5 mice, a) or co-transplanted with $0.5\times10^6$ placenta derived adherent cells cultured in 2D conditions (2D-ASC; 2 mice, b), or placenta derived adherent cells cultured in 3D conditions (3D-ASC), in the pluriX™ bioreactor (5 mice, c). Bone marrow (BM) was then collected from mice femurs and tibias. Human cells in the BM were detected by flow cytometry. The percentage of CD45 expressing human cells was determined by incubating cells with anti-human CD45-FITC. Note the higher percentage of human cells (hCD45+) in the bone marrow of mice co-transplanted with 2D-ASC (b) as well as with 3D-ASC (c) in comparison to the percentage of human cells in the mice treated with HSCs alone (a). The higher engraftment seen in mice treated with 3D-ASC cultured cells in comparison to mice treated with 2D-ASC cultured cells indicates a higher therapeutic advantage unique to 3D cultured ASCs.

Human CD34+ hematopoietic cells and 3D-ASC derived from placenta or adipose were co-transplanted in irradiated NOD-SCID mice. Engraftment efficiency was evaluated 4 weeks following co-transplantation, and compared to mice transplanted with HSC alone. As is shown in Table 2 and FIG. 5, co-transplantation of 3D-ASC and UCB CD34+ cells resulted in considerably higher engraftment rates and higher levels of human cells in the BM of recipient mice compared to mice treated with UCB CD34+ cells alone.

TABLE 2

| Transplanted cells | Average h-CD45 | STDEV |
| --- | --- | --- |
| CD34 | 3.8 | 7.9 |
| CD34 + 3D-ASC from placenta | 5.1 | 12.2 |
| CD34 + 3D-ASC from adipose | 8.7 | 9.6 |

Figure 14:
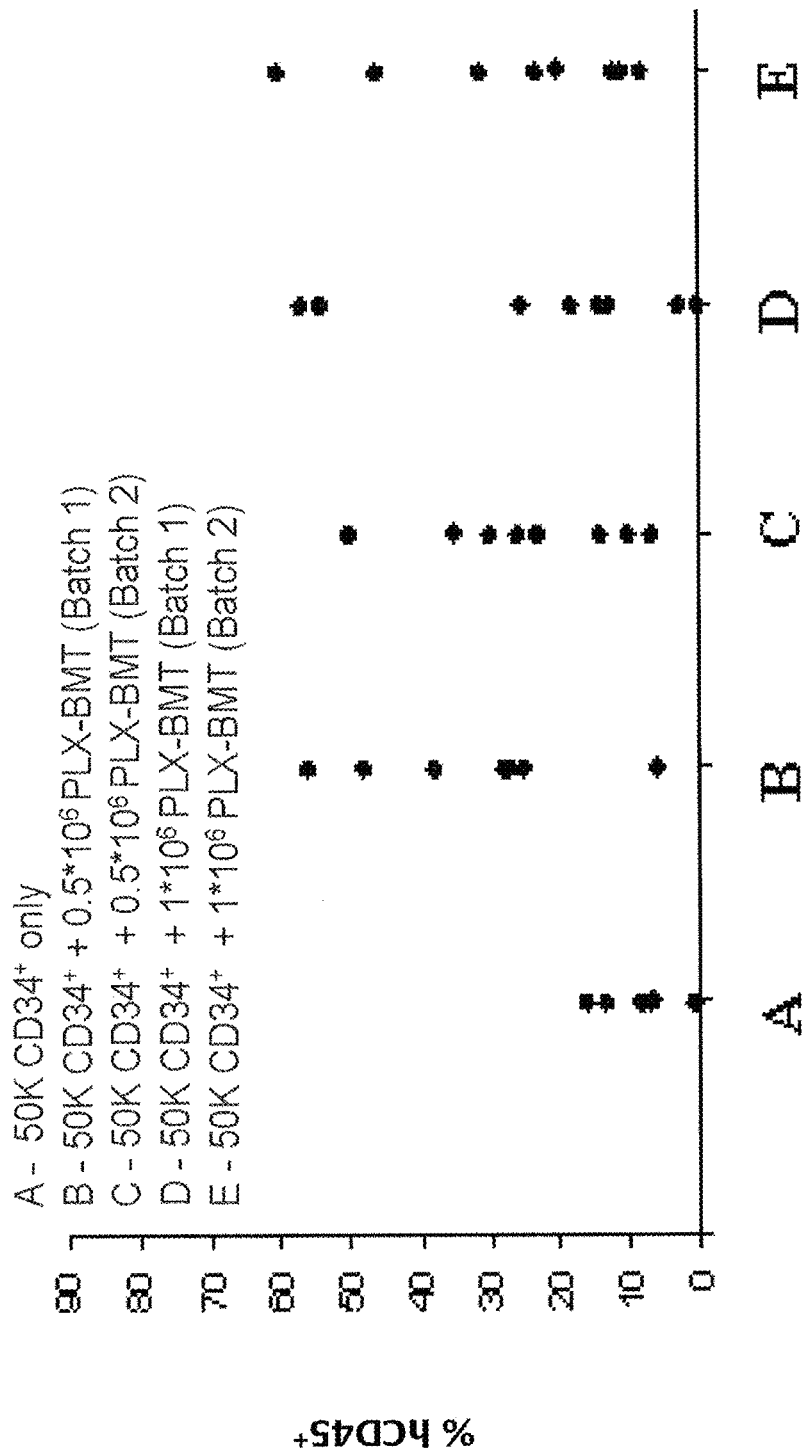
FIG. 14 presents results illustrating the combined effect of treatment with 3D-ASC and allogeneic bone marrow transplantation (PLX-BMT), namely enhancement of the engraftment of human umbilical cord blood (hUCB). The results were obtained with 350 rad irradiated NOD mice, with engraftment taking place 5 weeks after injection. Similar engraftment results were obtained when busulfan was used instead of irradiation, illustrating the efficacy and synergy of the combined treatment also for treating compromised endogenous hematopoietic system due to irradiation or chemotherapy.

FIG. 14 presents engraftment results showing the percentage of hCD45+ cells for different batches and doses of 3D-ASC. Similar engraftment results were obtained when busulfan was used instead of irradiation, illustrating the efficacy and synergy of the combined treatment also for treating compromised endogenous hematopoietic system due to irradiation or chemotherapy.

3D-ASC Improved Engraftment of HSC in Mice Treated with Chemotherapy—

Human CD34+ hematopoietic cells were co-transplanted with 500,000-2D-ASC or 3D-ASC derived from placenta, into NOD-SCID mice pretreated with chemotherapy. Engraftment efficiency was evaluated 3.5 weeks following co-transplantation, and compared to mice transplanted with HSC alone. As is shown in Table 3, co-transplantation of ASC and UCB CD34+ cells resulted in higher engraftment levels in the BM of the recipient mice compared to UCB CD34+ cells alone. Moreover, as is shown in Table 3, the average level of engraftment was higher in mice co-transplanted with placenta derived adherent stromal cells grown in the PluriX bioreactor system (3D-ASC) than in the mice co-transplantation with cells from the same donor, grown in the conventional static 2D culture conditions (flask).

TABLE 3

| Transplanted cells | Average h-CD45 | STDEV |
| --- | --- | --- |
| CD34 | 0.9 | 1.1 |
| CD34 + conventional 2D cultures from placenta | 3.5 | 0.2 |
| CD34 + 3D-adherent stromal cell from placenta | 6.0 | 7.9 |

FACS analysis results shown in FIGS. 6A-6B demonstrate the advantage of co-transplanting ASC with hHSCs (FIG. 6B), and the ability of ASC to improve the recovery of the hematopoietic system following HSC transplantation.

Taken together, these results show that ASCs may serve as supportive cells to improve hematopoietic recovery following HSCs transplantation (autologous or allogeneic). The ability of the 3D-ASCs to enhance hematopoietic stem and/or progenitor cell engraftment following HSCs transplantation may result from the 3D-ASC ability to secrete HSC supporting cytokines that may improve the homing, self-renewal and proliferation ability of the transplanted cells, or from the ability of those cells to rebuild the damaged hematopoietic microenvironment needed for the homing and proliferation of the transplantable HSCs.

Example 4

Assessment of the Ability of Placenta Derived 3D-Adherent Stromal Cells to Improve HSC Restoration Following Irradiation and Chemical Damage 3D-adherent stromal cell's support of endogenous HSC restoration of recipient was evaluated by the level of murine hematopoietic cells (mCD45+) detected in sub lethally irradiated or chemotherapy pretreated immune deficient NOD-SCID mice.

Materials and Experimental Procedures

Detection of Restored Cells in Irradiated Mice—

Seven week old male and female NOD-SCID mice (NOD-CB17-Prkdcscid/J; Harlan/Weizmann Inst., Rehovot Israel) were maintained in sterile open system cages, given sterile diets and autoclaved acidic water. The mice were sub lethally irradiated (350 cGy), and thereafter (48 hr post irradiation) transplanted with 50,000-100,000 hCD34$^+$ cells with or without adherent stromal cells ($0.5 \times 10^6$-$1 \times 10^6$) derived from placenta grown under 2D or 3D conditions (3-7 mice in each group). Cells were administered by intravenous injection to a lateral tail vein. Four to six weeks following transplantation the mice were sacrificed by dislocation and BM was collected by flushing both femurs and tibias with FACS buffer (50 ml PBS, 5 ml FBS, 0.5 ml sodium azide 5%). Measurement of murine CD45 hematopoietic cell marker expressing cells in the treated NOD-SCID mice was effected by incubating cells with anti-Mouse CD45-FITC (IQ Products, Groningen, The Netherlands) representing restoration of the mouse Haematopoetic system.

Detection of Restored Cells in Mice Treated with Chemotherapy—

6.5 week old male NOD-SCID mice (NOD.CB17/Jh-kiHsd-scid; Harlan, Rehovot Israel), maintained as described hereinabove for irradiated mice, were injected intraperitoneally with Busulfan (25 mg/kg—for 2 consecutive days). Two days following the second Busulfan injection, mice were injected human CD34+ cells alone, or together with $0.5 \times 10^6$ adherent stromal cells, produced from the placenta. 3.5 weeks following transplantation, mice were sacrificed, and the restoration of human hematopoietic cells was determined as described hereinabove for irradiated mice.

Results

3D-Adherent Stromal Cells Improved Engraftment of HSC in Irradiated Mice—

Human CD34+ hematopoietic cells and 3D-adherent stromal cells derived from placenta or adipose tissues were co-transplanted in irradiated NOD-SCID mice. Recovery efficiency of the mouse hematopoietic system was evaluated 4 weeks following co-transplantation, and compared to the self recovery in mice transplanted with hHSC without placenta adherent stromal cells. As is shown in Table 4, co-transplantation of both 2D and 3D-adherent stromal cells and UCB CD34+ cells resulted in considerably higher recovery rates compared to mice treated with UCB CD34+ cells alone as reflected by levels of expression of mCD45. Note that improvement was higher in 3D expanded cells.

TABLE 4

| Transplanted cells | Average m-CD45 | STDEV |
|---|---|---|
| hCD34 | 8.3 | 1.925 |
| hCD34 + 2D-adherent stromal cells from placenta | 12.46 | 0.66 |
| hCD34 + 3D-adherent stromal cells from placenta | 18.86 | 3.08 |

3D-Adherent Stromal Cells Improved Engraftment of HSC in Mice Treated with Chemotherapy—

Human CD34+ hematopoietic cells were co-transplanted with placenta derived adherent stromal cells into NOD-SCID mice pretreated with chemotherapy. Recovery efficiency of the recipient mouse hematopoietic system was evaluated 3.5 weeks following co-transplantation, and compared to mice transplanted with HSC alone. As is shown in Table 5 co-transplantation of adherent stromal cells and UCB CD34+ cells resulted in higher recovery rates of the hematopoietic system of the recipient mice compared to UCB CD34+ cells alone. Moreover, as is shown in Table 5, the average level of recovery was dose dependent to the number of administered adherent stromal cells.

TABLE 5

| Transplanted cells | Average m-CD45 | STDEV |
|---|---|---|
| CD34 | 13.3 | 1.1 |
| CD34 + 3D-ASC from placenta $0.25 * 10^6$ | 15.2 | 1.9 |
| CD34 + 3D-ASC from placenta $0.5 * 10^6$ | 16.1 | 3.3 |
| CD34 + 3D-ASC from placenta $0.75 * 10^6$ | 29.0 | NA |

Figure 8B:
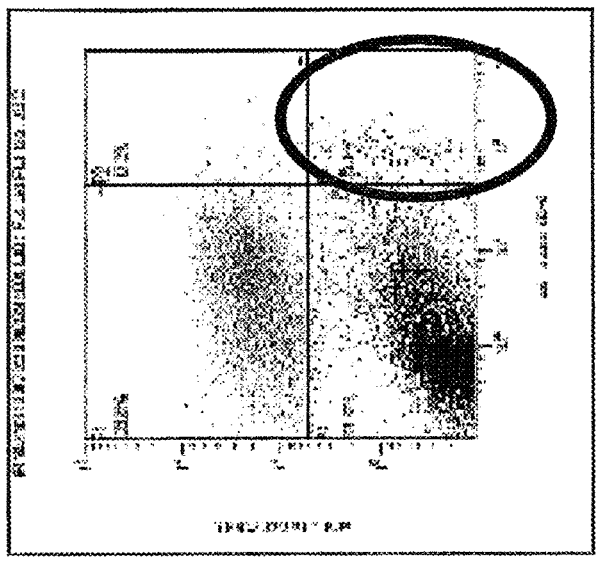
FIGS. 8A-8B are FACS analyses of mouse CD45+ cells in mice transplanted with human CD34+ cells only (FIG. 8A) in comparison to mice transplanted with human CD34+ cells together with human adipose tissue derived adherent stromal cells (FIG. 8B). Note the significantly higher percentage of mouse hematopoietic population (mCD45+) (FIG. 8B—9.42%) in a mouse co-transplanted with adipose tissue derived adherent cell in comparison to a mouse treated with human CD34+ alone (FIG. 8A—5.57%).
Figure 8A:
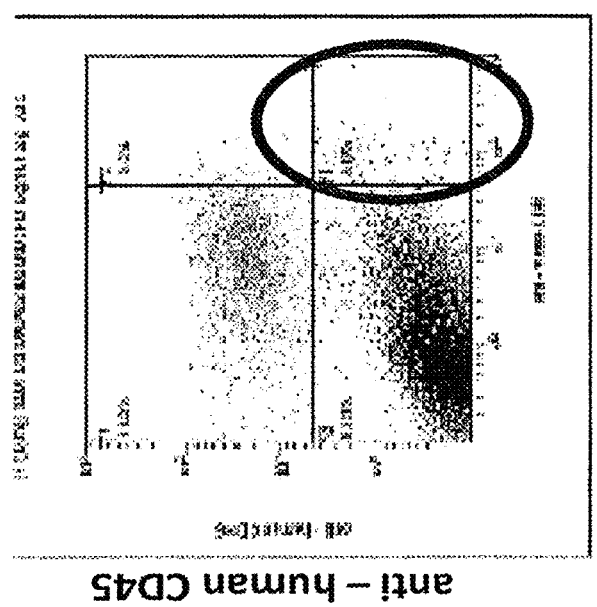

FACS analysis results shown in FIGS. 8A-8B demonstrate the advantage of co-transplanting hHSCs with adipose derived adherent stromal cells (FIG. 8B), compared to hHSCs alone (FIG. 8A) and the ability of adherent stromal cells to improve the recovery of the recipient hematopoietic system.

FIGS. 8A-8B further demonstrate that following transplantation or administration of the adherent stromal cells of the present invention, the endogenous hematopoietic system of the recipient was substantially restored. This resulted with increasing count of endogenous hematopoietic cells. The adherent stromal cells of the present invention, inter alia, improve or induce the recovery of the recipient endogenous hematopoietic system and/or constituents. Presumably recovery is facilitated by providing the soluble or resident cytokines needed for controlled hematopoietic cell differentiation and proliferation.

Example 5

The effect of 3D-ASC (PLX) cells on the survival of irradiated mice was examined following intravenous administration of 3D expanded ASC into C3H mice 24 hours post irradiation (850 cGy).

Materials and Experimental Procedures

Preparation.

Mice (C3H males, 20 gram, ~8 weeks old) were purchased from Harlan Company. Animals were housed for 1 week in an SPF facility for acclimation before experiment. 30 C3H male mice were exposed to total body radiation (850 cGy). 24 hours after the irradiation, 15 mice were injected with 3D-ASC cells ($1\times10^6$) in 250 µl plasmaLyte A/mouse by slow intravenous injection (~1 minute) to the one of the lateral tail veins. Cells were gently mixed all along the injection step to prevent aggregation. The remaining control group of 15 mice were injected with the same volume (250 µl) of plasmaLyte A (vehicle).

On day 9, 3 animals from each group along with additional 3 control mice (which were not irradiated or injected with 3D-ASC cells were sacrificed. Spleens and bone marrow were harvested. Total nucleated cell number in BM was counted and spleens were taken to colony formation assay.

Follow up for survival of the remaining mice was performed for 23 days. During the experiment mice were monitored under SPF conditions. Animals were inspected and weighed 2-3 times a week. Mice that survived till the final time point were sacrificed by $CO_2$ inhalation and their BM was harvested for nucleated BM cells enumeration.

Results

Figures 9A, 9B:
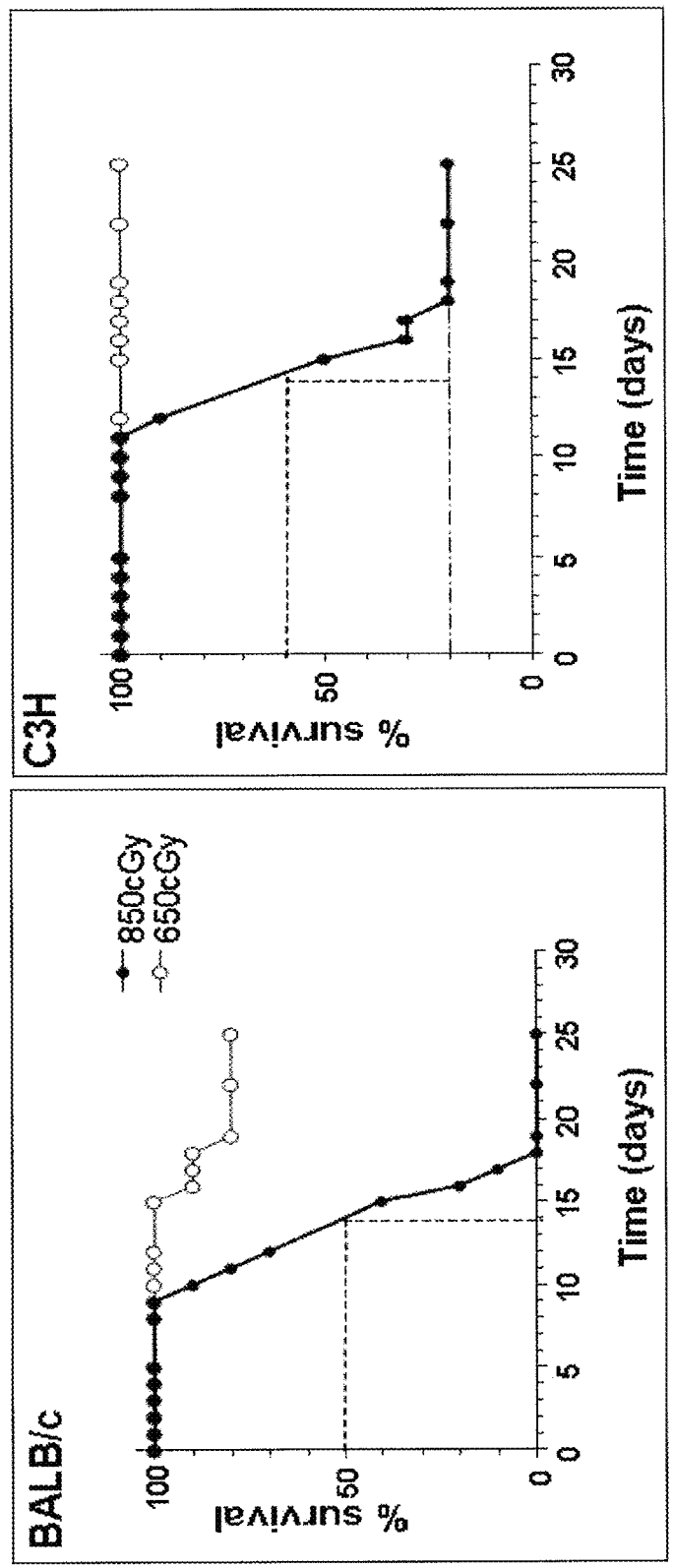
FIGS. 9A and 9B illustrate a follow up of mouse survival after two doses of ionizing radiation (without 3D-ASC treatment) in BALB/c (FIG. 9A) and C3H (FIG. 9B) mice.

FIGS. 9A and 9B illustrate a follow up of mouse survival after two doses of ionizing radiation (without 3D-ASC treatment) in BALB/c and C3H mice.

Figures 10A, 10B:
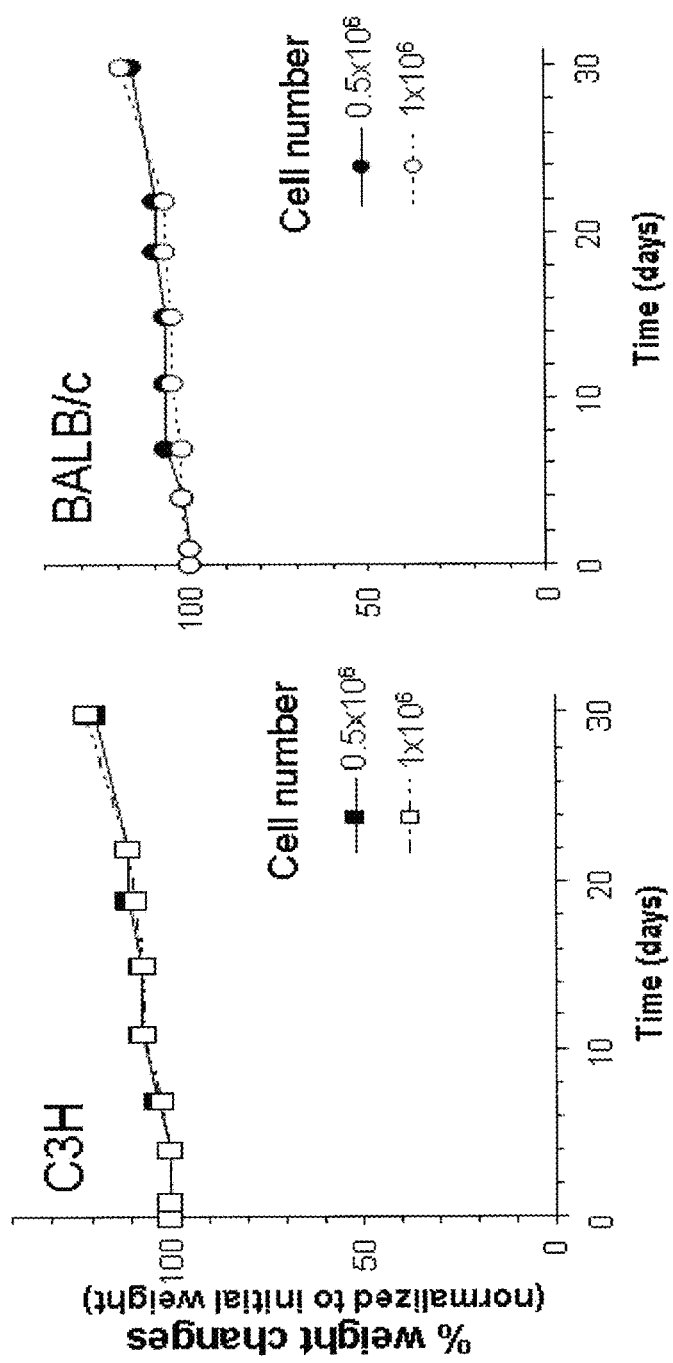
FIGS. 10A and 10B illustrate the effect of different doses of 3D-ASC (PLX) cells on weight changes of non-irradiated C3H (FIG. 10A) and BALB/c (FIG. 10B) mice, illustrating the safety of intravenous injection of the 0.5 and 1×10$^6$ cells doses.

FIGS. 10A and 10B illustrate the effect of different doses of 3D-ASC (PLX) cells on weight changes of non-irradiated C3H and BALB/c mice, illustrating the safety of intravenous injection of the 0.5 and $1\times10^6$ cells doses.

Figures 11A, 11B:
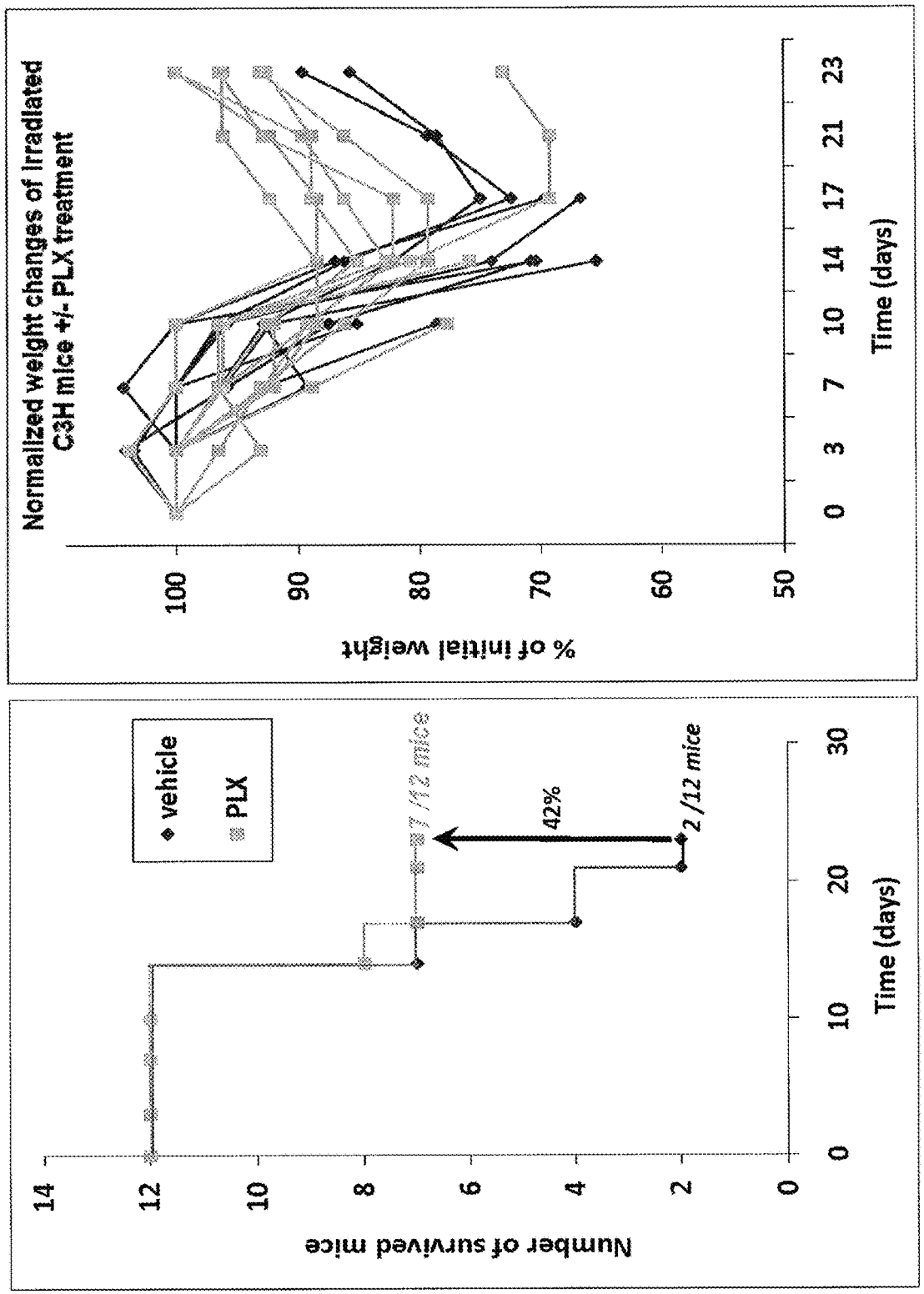
FIGS. 11A and 11B illustrate C3H mice survival (FIG. 11A) and normalized weight changes (FIG. 11B) following exposure to radiation. "PLX" denotes the treatment with 3D-ASC cells. "Vehicle" denotes the control mice which did not receive PLX cells.

FIGS. 11A and 11B illustrate C3H mice survival (FIG. 11A) and normalized weight changes (FIG. 11B) following exposure to radiation. "PLX" denotes the treatment with 3D-ASC cells. "Vehicle" denotes the control mice which receive plasmaLyte A without PLX cells.

FIGS. 12A-12C illustrate fixed spleen weight in irradiated mice either untreated (left) or treated (right) with PLX cells and further visually illustrates exemplary prepared spleens from the corresponding groups of mice. The preparation was carried out 9 days after C3H mice were exposed to sub-lethal irradiation, followed by 3D-ASC (PLX) injection, BM cell regeneration was tested by the spleen colony formation assay. The colonies originated from progenitor cells re-suspended in BM.

Figure 13B:
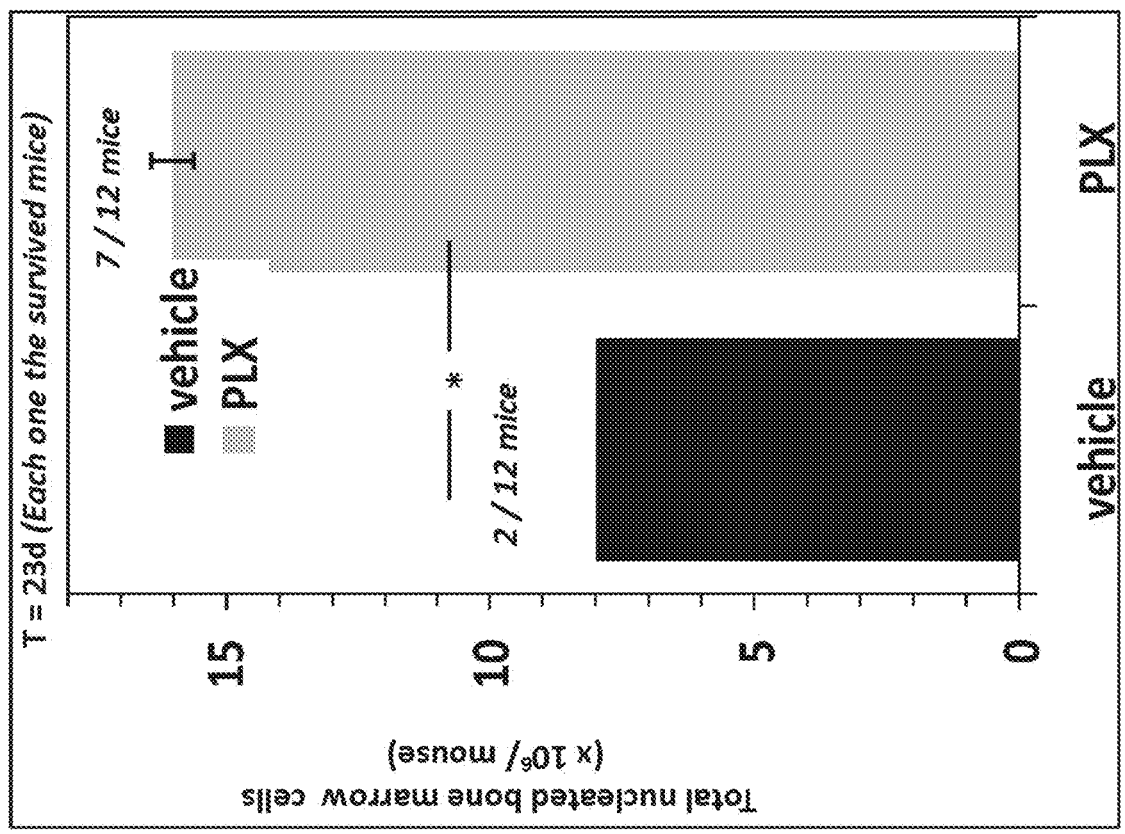
FIGS. 13A-13B illustrate bone marrow progenitor cells repopulation. Nucleated BM cells were collected from the femur and tibia of both hind extremities of the mice by flushing with PBS followed by RBCs lysis using lysing solution and then enumerated by direct count. Normal BM cell counts in non-irradiated mice ranges ~30×10$^6$. Mice treated with 3D-ASC (PLX) had a much higher level of total nucleated bone marrow cells after 9 days and 23 days following exposure to radiation.
Figure 13A:
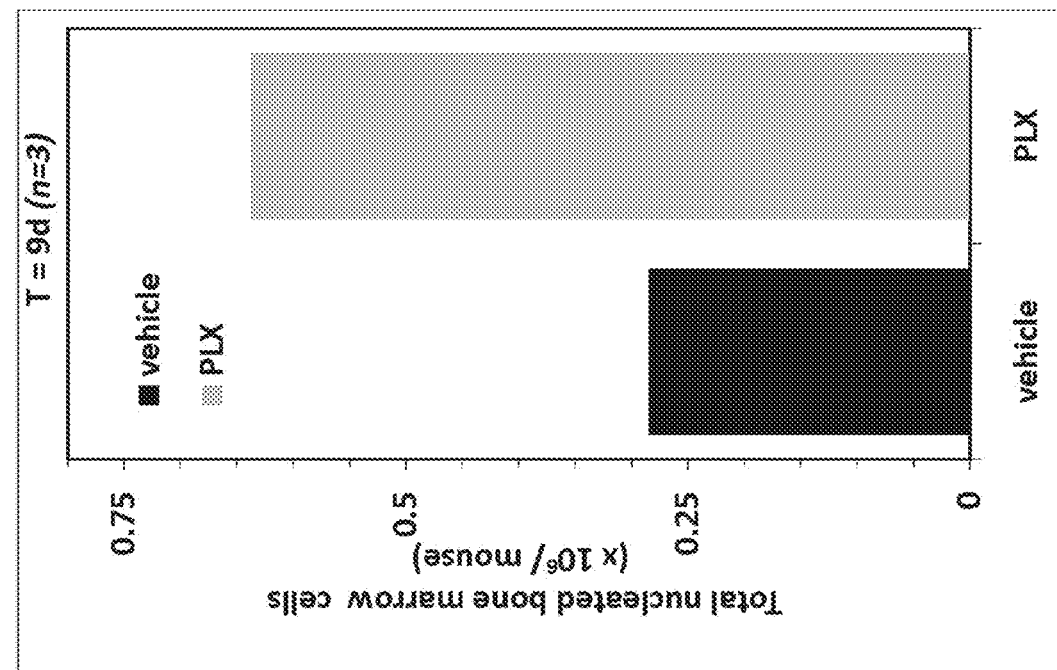

FIGS. 13A-13B illustrate bone marrow progenitor cells repopulation. Nucleated BM cells were collected from the femur and tibia of both hind extremities of the mice by flushing with PBS followed by RBCs lysis using lysing solution and then enumerated by direct count. Normal BM cell counts in non-irradiated mice ranges ~$30\times10^6$. Mice treated with 3D-ASC (PLX) had a much higher level of total nucleated bone marrow cells after 9 days and 23 days following exposure to radiation.

To summarize, the following aspects of the effect of 3D-ASC treatment on sub lethally radiated mice were demonstrated: tissue histology (lungs, spleen, intestines, liver, skin), BM reconstitution as a function of total number of BM cells, spleen colonies and survival.

Example 6

The effect of 3D-expanded Adherent Stromal Cells from placenta (PLX) on the survival of irradiated mice was examined following intravenous administration into C3H mice 24 hours post irradiation (770 cGy).

Materials and Experimental Procedures

Preparation.

Mice (C3H males, 20 gram, ~6 weeks old) were purchased from Harlan Company. Animals were housed for 2 weeks in an SPF facility for acclimation before beginning the experiment. Thirty C3H male mice were exposed to total body radiation (770 cGy). Twenty-four hours after the irradiation, 15 mice were injected with 3D-ASC cells ($1\times10^6$) in 250 µl plasmaLyte A/mouse by slow intravenous injection (~1 minute) to one of the lateral tail veins. Cells were gently mixed all along the injection step to prevent aggregation. The remaining control group of 15 mice were injected with the same volume (250 µl) of plasmaLyte A (vehicle).

On day 8, 3 animals from each group along with additional 3 control mice (which were not irradiated or injected with 3D-ASC cells) were sacrificed. Blood for a complete blood chemistry (CBC) was taken before sacrificing. Bone marrow (BM) was harvested and the total nucleated cell number in BM was determined by counting. Liver, lung, and intestine were fixed for histology.

Follow up for survival of the remaining mice was performed for 18 days. During the experiment mice were monitored under SPF conditions. Animals were inspected and weighed 2-3 times a week. Mice that survived until the final time point were sacrificed by $CO_2$ inhalation. Prior to sacrificing, blood from retro-orbital sinus was sampled for CBC. Afterwards, bone marrow was harvested. The total cell nucleated BM cells amount from 1 leg (tibia and femur) were enumerated by direct count, and smears were prepared from the other leg (tibia and femur). Liver, lung, and intestine were taken for histology.

Results

Figure 17:
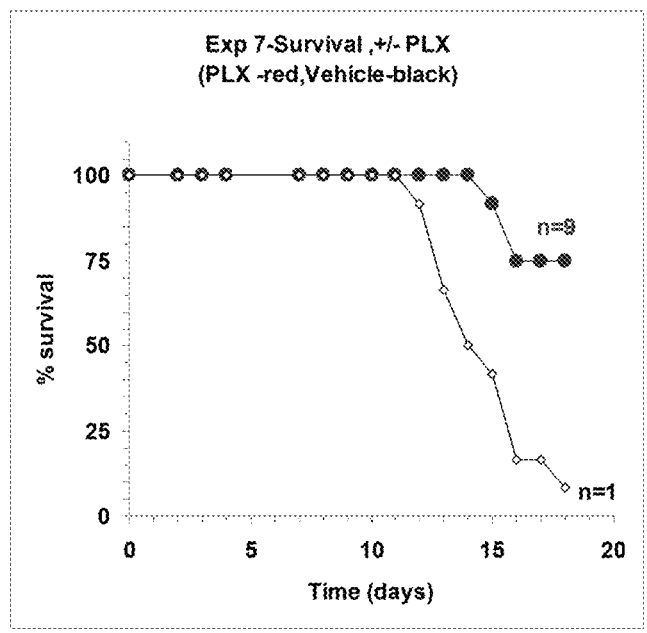
FIG. 17 illustrates the survival data for mice treated intravenously with PLX cells 24 hours following irradiation (filled circles) and mice not receiving PLX treatment (open circles).
Figure 18A:
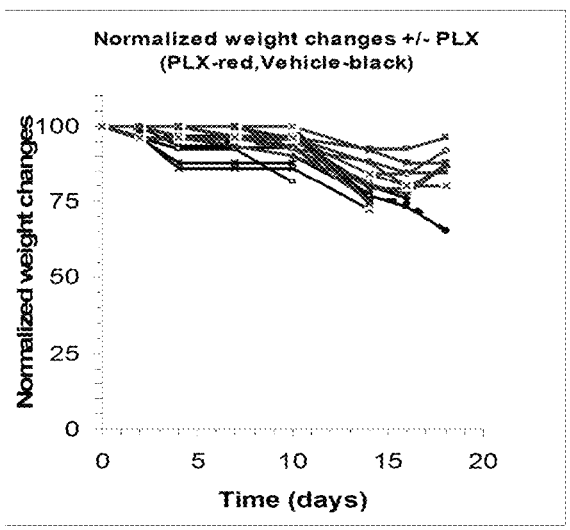
FIGS. 18A-18B present the weight change with time through day 18 as either a normalized weight change (FIG. 18A) or an average weight change (FIG. 18B).
Figure 18B:
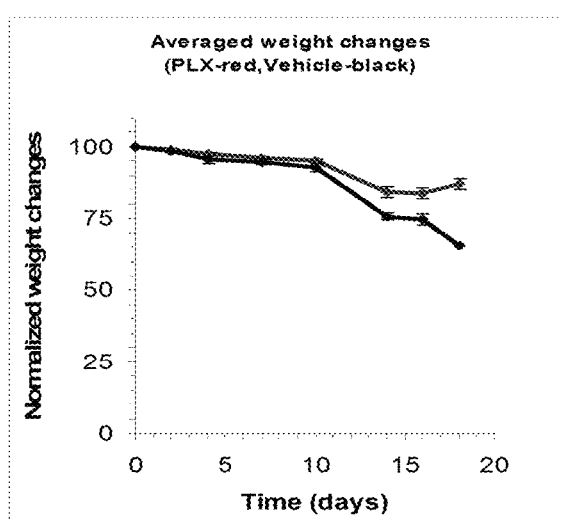

Survival following irradiation with a dose of 770cGy is shown in FIG. 17 for mice treated with PLX cells (filled circles) and mice not receiving PLX treatment (open circles). FIGS. 18A and 18B present the weight change with time through day 18 as either a normalized weight change (FIG. 18A) or an average weight change (FIG. 18B).

Figure 19A:
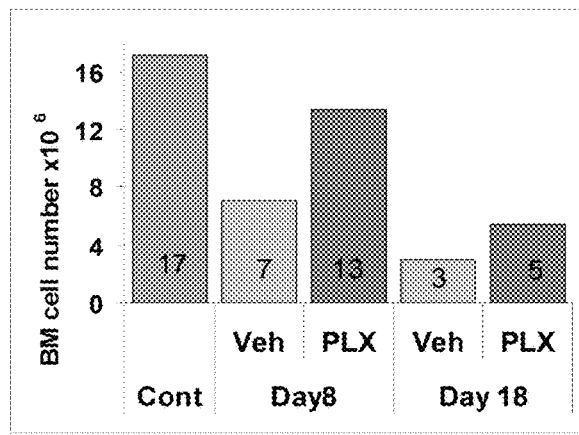
FIGS. 19A-19B present the whole marrow cell count for control, vehicle treated, and PLX treated mice at day 8 (FIG. 19A; all groups n=3) and day 18 (FIG. 19B; control n=2, PLX n=9, and vehicle n=1).
Figure 19B:
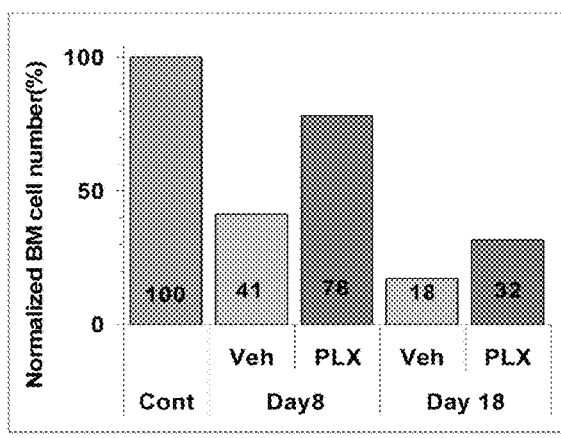
Figure 20A:
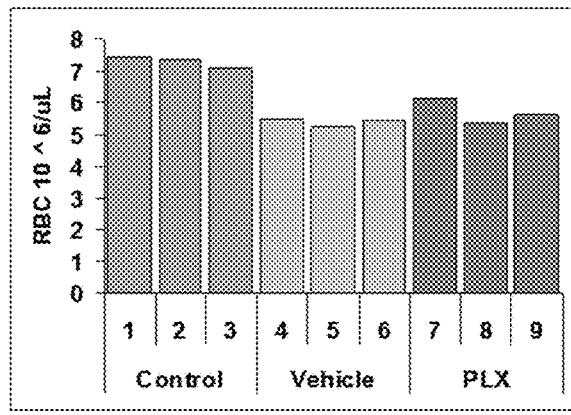
FIGS. 20A-20B present the red blood cell (RBC) numbers on day 8 (FIG. 20A) and day 18 (FIG. 20B).
Figure 20B:
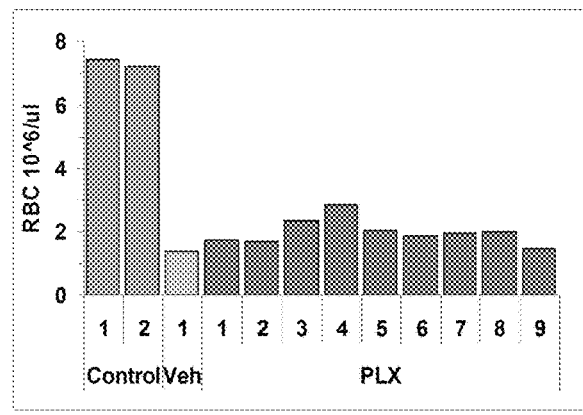

FIGS. 19A and 19B present the whole marrow cell count (tibia and femur from one side) for control, vehicle treated, and PLX treated mice at day 8 (FIG. 19A; all groups n=3) and day 18 (FIG. 19B; control n=2, PLX n=9, and vehicle n=1). On day 8, the number of BM cells of the PLX group was similar to the number for controls, while the number of BM cells in the vehicle group was much lower. The number of bone marrow cells on day 18 was lower, but the groups showed the same trend of a higher cell number in the PLX group compared to vehicle treated FIGS. 20A and 20B present the red blood cell (RBC) numbers in the different groups on day 8 (FIG. 20A) and day 18 (FIG. 20B). On day 18 the RBC number in the irradiated groups was very low compared to control mice. But in most PLX treated mice, the RBC number was higher than in the vehicle treated mouse.

Figure 21A:
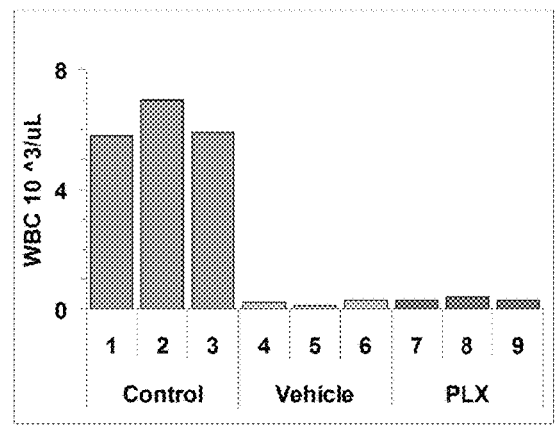
FIGS. 21A-21B show the white blood cell (WBC) counts on day 8 (FIG. 21A) and day 18 (FIG. 21B).
Figure 21B:
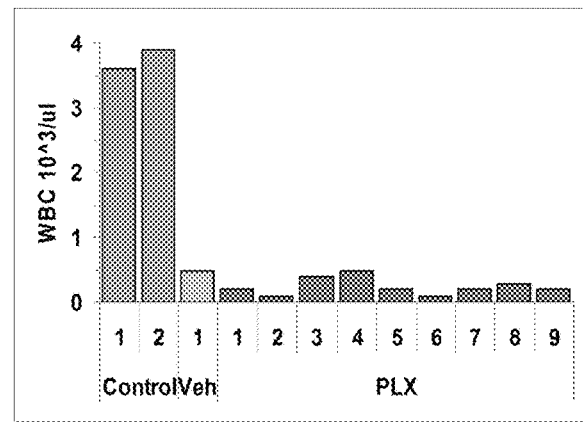

In FIGS. 21A-21B, the white blood cell (WBC) counts are compared on day 8 (FIG. 21A) and day 18 (FIG. 21B). The WBC are sharply depressed in both groups of irradiated mice on day 8. The counts remain low on day 18.

Figure 22A:
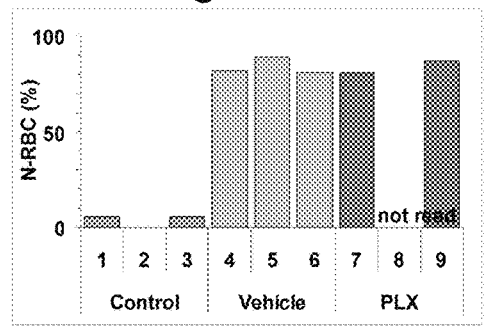
FIGS. 22A-22D present data for nucleated RBC on day 8 (FIG. 22A, FIG. 22C) and day 18 (FIG. 22B, FIG. 22D). Upper graphs (FIG. 22A, FIG. 22B) present the percentage of nucleate RBC. The lower graphs (FIG. 22C, FIG. 22D) present the absolute numbers of nucleated RBC×10$^3$ per microliter.
Figure 22B:
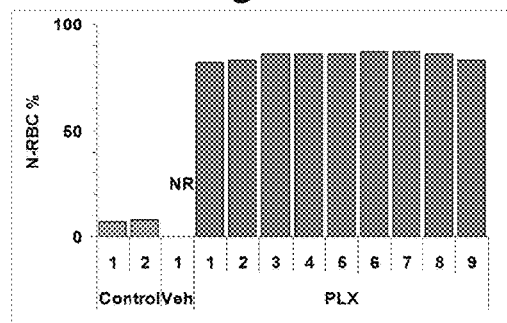
Figure 22C:
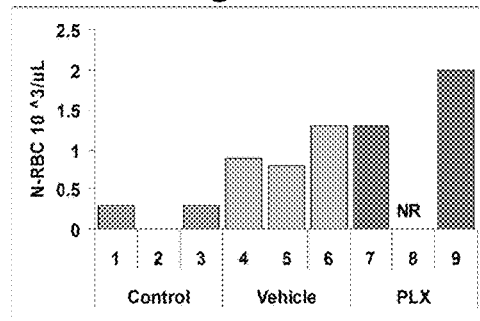
Figure 22D:
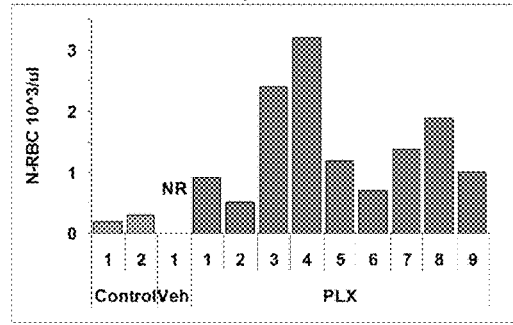

FIGS. 22A-22D present data for nucleated RBC on day 8 (FIG. 22A, FIG. 22C) and day 18 (FIG. 22B, FIG. 22D). Upper graphs (FIG. 22A, FIG. 22B) present the percentage of nucleate RBC, an immature cell type. The lower graphs (FIG. 22C, FIG. 22D) present the absolute numbers of nucleated RBC x $10^3$ per microliter. Both the percentage and total number of nucleated RBC were increased compared to control mice. On day 18, the sole surviving vehicle control mouse had so few cells that the count was inaccurate and not reported.

Figure 23A:
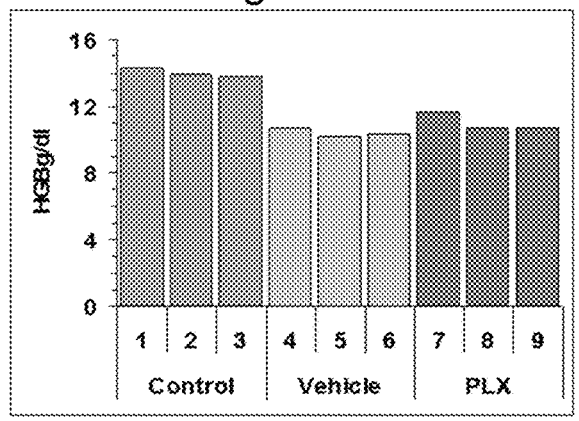
FIGS. 23A-23B present hemoglobin levels at day 8 (FIG. 23A) and day 18 (FIG. 23B).
Figure 23B:
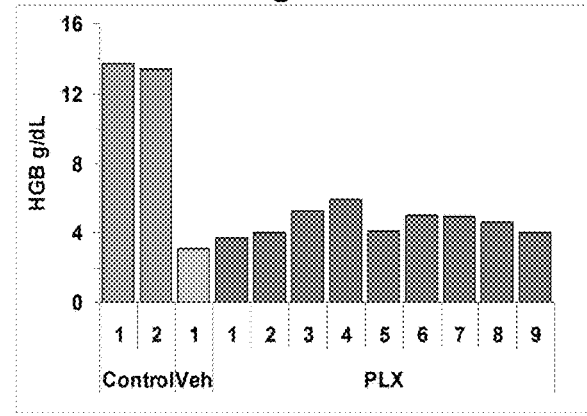
Figure 24A:
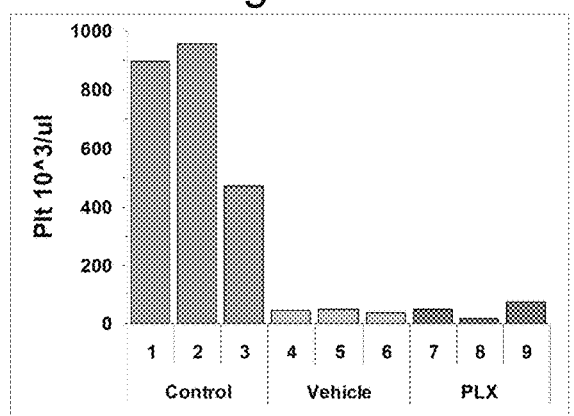
FIGS. 24A-24B present platelet numbers on day 8 (FIG. 24A) and day 18 (FIG. 24B).
Figure 24B:
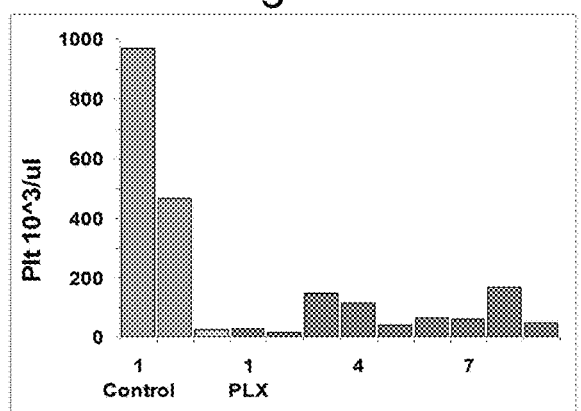
Figure 25A:
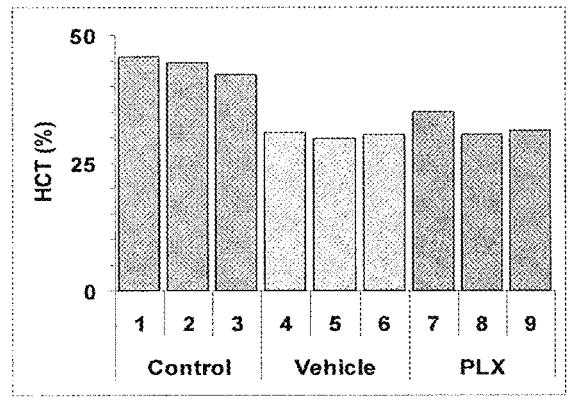
FIGS. 25A-25B present hematocrit values at day 8 (FIG. 25A) and day 18 (FIG. 25B).
Figure 25B:
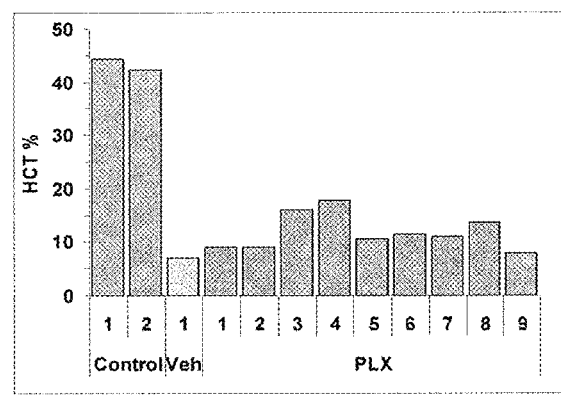

Other blood parameters measured included hemoglobin (FIGS. 23A-23B), platelet numbers (FIGS. 24A-24B), and hematocrit (FIGS. 25A-25B). In each figure, panel A presents the results on day 8, while panel B presents the results on day 18. As for the RBC counts, the hemoglobin was reduced at both time points for the vehicle control compared the mice treated with PLX cells. The platelet numbers were also elevated in PLX treated mice compared to vehicle controls. The hematocrit was also possibly elevated in PLX mice compared to vehicle controls. Unirradiated control mice are also presented for each day and assay as a comparison.

CONCLUSIONS

These results show that the dose of irradiation used was lethal in the mouse strain used. At 770cGy, only one of twelve mice survived to day 18 (an 8% survival rate) in the vehicle treated group. Intravenous injection of PLX cells increase the fraction of surviving mice to 75% (9/12) following the same dose of irradiation. Throughout the follow up period, PLX treated mice fared better than vehicle treated mice. At day 18 PLX mice were on average gaining weight, while the single surviving vehicle treated mouse was still losing weight. The group treated with IV PLX injection also had higher bone marrow cell counts at both day 8 and day 18. The blood parameters were also generally better in the PLX treated mice, especially the RBC and platelets on day 18. These effects were less evident at day 8, which was before the initiation of the phase of reduced survival.

Example 7

The effect of 3D-expanded Adherent Stromal Cells from placenta (PLX) on serum cytokines profile of irradiated mice was examined following intravenous administration into C3H mice 24 hours post irradiation (770 cGy) 1 day and 4 days following PLX administration.

Materials and Experimental Procedures

Preparation. Mice (C3H males, 20 gram, ~6 weeks old) were purchased from Harlan Company. Animals were housed for 2 weeks in an SPF facility for acclimation before experiment. Four mice served as control untreated mice, while 26 mice were irradiated by 770 cGy. Twenty four hours after irradiation, 8 mice were injected IV with PLX and 8 mice were injected with Plasmalyte. Six mice were kept in reserve in case of unexpected mortality after IV injection. One day and four days after PLX injection, arterial blood was collected from 2 control non-irradiated mice, 2 control-irradiated, 4 vehicle-injected mice, and 4 PLX-injected mice. Serum was separated from the blood, then pooled together from each 2 mice to yield a sufficient volume of 6500. The collected sera was kept at −20° C. until analyzed with "Mouse Inflammatory Cytokines Multi-Analyte ELISArray Kit" (SABiosciences; cat #MEM-004A) for the following cytokines/growth factors IL1A, IL1B, IL2, IL4, IL6, IL10, IL12, IL17A, IFNγ, TNFα, G-CSF, and GM-CSF.

Results

Figure 26A:
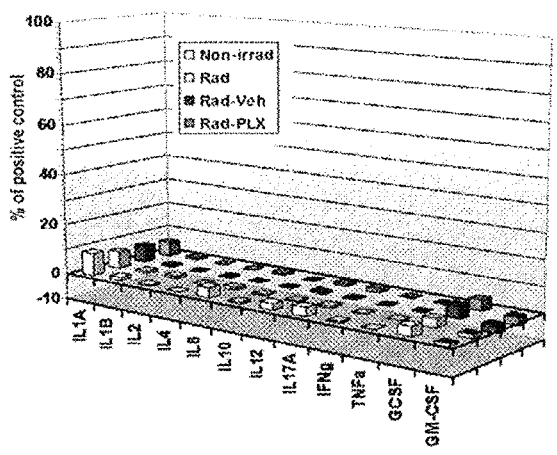
FIGS. 26A-26B present the cytokine profiles on day 1 (FIG. 26A) and on day 4 (FIG. 26B) following injection with PLX cells or vehicle.
Figure 26B:
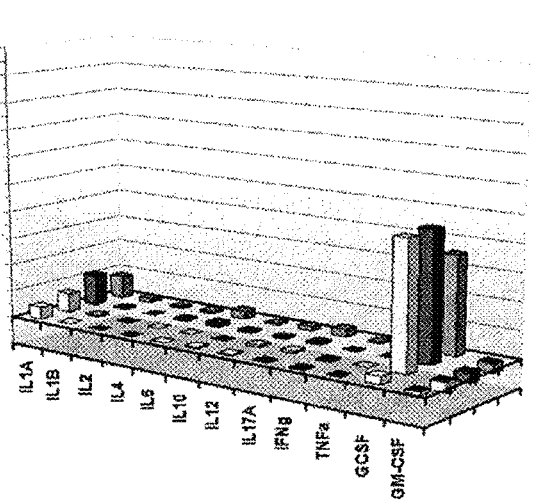

FIGS. 26A-26B present the cytokine profiles on day 1 (FIG. 26A) and on day 4 (FIG. 26B) following injection with PLX cells or vehicle. The most striking change was the increase in G-CSF levels in all mice treated with irradiation.

Example 8

The effect of 3D-ASC (PLX) cells on the survival of irradiated mice was examined following intramuscular administration of 3D expanded ASC into C3H mice 24 hours post irradiation (770 cGy).

Materials and Experimental Procedures

Preparation.

Mice (C3H males, ~24 gram, 7 weeks old) were purchased from Harlan Company. Animals were housed for 2 week in an SPF facility for acclimation before experiment. C3H male mice were exposed to total body radiation (770 cGy). Approximately twenty-four hours after the irradiation, 12 mice ("Irradiation+PLX" group) were injected with 50 µl of 3D-ASC cells (batch PD061210 153B04 at $20 \times 10^6$ cells/mL in plasmaLyte A) using an insulin syringe and 25 g needle into each caudal muscle, for a total dose of $2 \times 10^6$ cells/mouse. A second group ("Irradiation+PLX-2X") received the same initial injection, but in addition received a second $2 \times 10^6$ 3 D-ASC by intramuscular injections to each caudal muscle following a four day interval. For all injections, cells were gently mixed all along the injection step to prevent aggregation. A control group of irradiated mice were intramuscularly injected in the same manner with the same volume (1000 total, 50 µl per caudal muscle) of plasmaLyte A (vehicle).

The mice were followed for 21 days. During the experiment mice were monitored under SPF conditions. Animals were inspected and surviving mice weighed three times a week. Mice that survived until the final time point were sacrificed and their BM harvested for nucleated BM cells enumeration.

Results

FIGS. 27A-27B illustrate mouse survival (FIG. 27A) and weight change (FIG. 27B) in C3H mice given 770 cGy ionizing radiation. Mice receiving two intramuscular injections of $2 \times 10^6$ cells/dose on days 1 and 5 (circles) following irradiation had improved survival compared to either mice receiving a single intramuscular injection one day after irradiation or to the control irradiated mice that did not receive any PLX cells.

Example 9

The effect of 3D-expanded Adherent Stromal Cells from placenta (PLX) on the survival of irradiated mice was examined following intramuscular administration of two different doses (1 or 2 million cells/injection) of 3D-expanded ASCs into C3H mice 24 hours and/or 5 days post irradiation (770 cGy).

Materials and Experimental Procedures

Fourty-four C3H mice were exposed to total body radiation (770 cGy) at Sharett Institute of Oncology at Hadassah Hebrew University Medical Center. The irradiated mice were divided to 4 groups (11 mice/group) and treated as follows:
1. Injected twice with $1 \times 10^6$ PLX cells: 24 h after the irradiation and 5 days after irradiation (total number of injected cells $2 \times 10^6$).
2. Injected twice with $2 \times 10^6$ PLX cells: 24 h after the irradiation and 5 days after irradiation (total number of injected cells $4 \times 10^6$).
3. Injected once 5 days after irradiation with $2 \times 10^6$ PLX cells.
4. Injected with PlasmaLyte A (vehicle) only, as a control group.

All injections were performed intramuscularly (IM) in 100 microliter PlasmaLyte A/mouse (50 microliter injection to the muscles of each leg as 25 microliters×2 into 2 muscle sites of each leg).

Follow up for survival of the mice was monitored for 23 days. Animals were inspected daily and weighed 3 times a week. In critical time points the animals were tested twice daily. During the experiment the mice were monitored in SPF conditions.

On day 23 the surviving mice, along with 2 additional non-irradiated mice, were examined for complete blood chemistry (CBC) using blood from the retro-orbital sinus. Mice were then sacrificed and bone marrow harvested. The total number of bone marrow cells in both femurs and tibias in each surviving animal was also counted.

Results

Figure 28A:
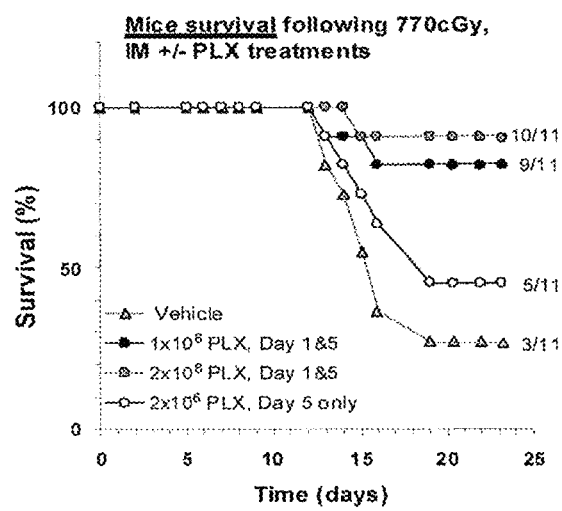
FIGS. 28A-28B present the survival (FIG. 28A) and average weight change (FIG. 28B) following irradiation with a dose of 770cGy and treated intramuscularly (IM) with the cell doses indicated on day 1 or days 1 and 5 following irradiation.
Figure 28B:
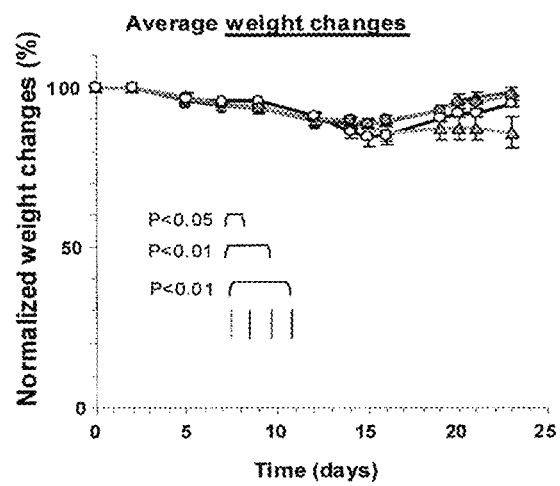

FIGS. 28A-28B present the survival (FIG. 28A) and average weight change (FIG. 28B) following irradiation with a dose of 770cGy. Three of eleven mice treated with vehicle (triangle) survived the monitoring period. Five of eleven mice treated with $2 \times 10^6$ PLX cells only on day 5 (open circles) survived. Nine of eleven mice treated with $1 \times 10^6$ PLX cells on days 1 and 5 (filled circles) survived. When $2 \times 10^6$ PLX cells were administered on day 1 and day 5 (top set of filled circles), 10 of 11 mice survived.

Figure 29:
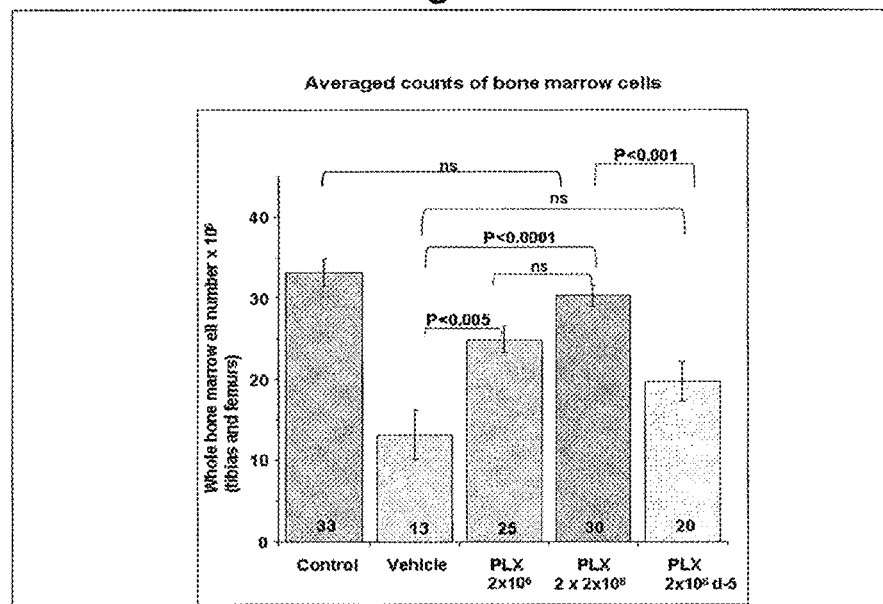
FIG. 29 illustrates the average cell counts on day 23 for bone marrow cells.

The average cell counts on day 23 for bone marrow cells in each group are presented in FIG. 29. Consistent with the survival data, mice treated with $2 \times 10^6$ PLX cells on days 1 and 5 had the highest total bone marrow cell counts.

Figure 30A:
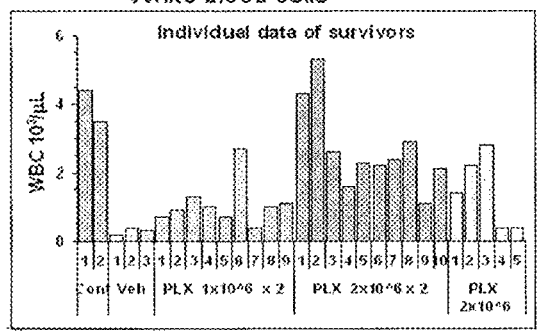
FIGS. 30A-30D present white blood cell (WBC) and red blood cell (RBC) counts at day 23. Individual counts for each mouse are presented in FIG. 30A (WBC) and FIG. 30B (RBC).
Figure 30B:
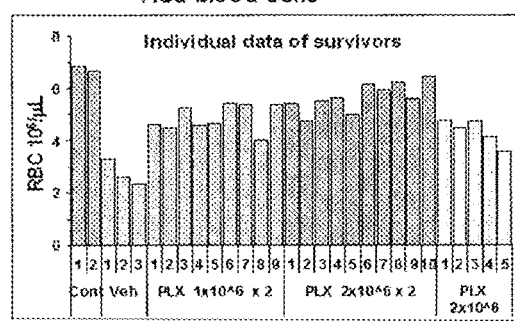
Figure 30C:
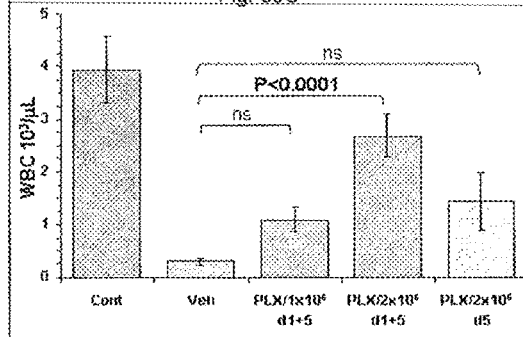
Figure 30D:
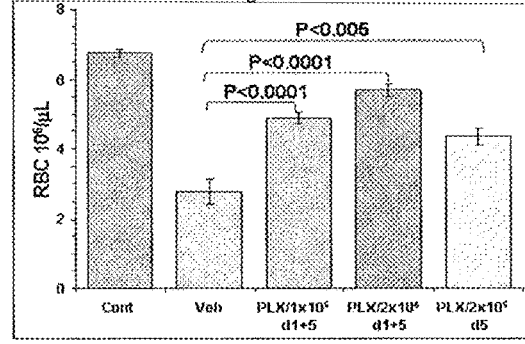

The white blood cell (WBC) and red blood cell (RBC) counts at the termination of the experiment (day 23) are shown in FIGS. 30A-30D. Individual counts for each mouse are presented in FIG. 30A (WBC) and FIG. 30B (RBC). FIG. 30C (WBC) and FIG. 30D (RBC) present the pooled data for each group. Once again, mice treated with $2 \times 10^6$ PLX cells on days 1 and 5 had the highest average counts for both WBC and RBC, although there was mouse to mouse variation. Compared to the average cell counts for vehicle treated mice, the WBC and RBC counts for the $2 \times 10^6$ PLX cells on days 1 and 5 group were significantly increased ($p<0.0001$). The average number of RBC were also significantly increased compared to vehicle treated mice in the $1 \times 10^6$ PLX cells on days 1 and 5 group ($p<0001$) and the $2 \times 10^6$ PLX cells on day 5 only group ($p<005$).

FIGS. 31A-31B present the day 23 platelet counts for individual mice (FIG. 31A) and the averaged groups (FIG. 31B). The increase in platelet counts was greatest in the $2 \times 10^6$ PLX cells on days 1 and 5 group. This increase was statistically significant compared to vehicle treated mice ($p<0.005$).

FIGS. 32A-32D present the day 23 results for hemoglobin (FIG. 32A, FIG. 32C) and hematocrit (FIG. 32B, FIG. 32D) for individual mice (FIG. 32A, FIG. 32B) and values averaged by group (FIG. 32C, FIG. 32D). For these parameters, all groups showed a significant increase relative to vehicle treated mice, but once again the increase was greatest in the $2 \times 10^6$ PLX cells on days 1 and 5 group.

Example 10

The effect of 3D-expanded maternal Adherent Stromal Cells from placenta (PLX) compared to 3D-expanded mixed maternal/fetal PLX cells on the survival of irradiated mice was examined following intramuscular administration of 2 million cells/injection of 3D expanded ASC into C3H mice 24 hours and 5 days post irradiation (770 cGy).

Placenta-derived adherent stromal cells that are at least about 90% maternal-derived cells (based on genotype or karyotype) were used as the "Maternal" PLX cells. "Mixed" PLX cells comprised about 70% maternal-derived cells and about 30% fetal-derived cells.

Twenty-seven 9 weeks old C3H mice were exposed to total body radiation (770cGy) at Sharett Institute of Oncology at Hadassah Hebrew University Medical Center. The irradiated mice were divided to 3 groups (9 mice/group) and treated as follows:

1. Injected twice with PLX-1 (mixed) at 2×10$^6$ cells/mouse: 24 h and 5 days after irradiation (total number of injected cells—4×10$^6$).
2. Injected twice with PLX-2 (maternal) at 2×10$^6$ cells/mouse: 24 h and 5 days after irradiation (total number of injected cells—4×10$^6$).
3. Injected twice with PlasmaLyte A: 24 h and 5 days after irradiation.

All injections were performed intramuscularly (IM) in 100 microliter PlasmaLyte A/mouse (50 microliter injection to the muscles of each leg as 25□ microliter into 2 muscle sites).

Survival was monitored for 23 days. Animals were inspected daily and weighed 3 times a week. During the experiment the mice were monitored in SPF conditions.

On day 23 the surviving mice, along with 2 additional non-irradiated mice, were examined for complete blood chemistry (CBC) using blood from the retro-orbital sinus. Mice were sacrificed and bone marrow harvested. The total number of bone marrow cells in both femurs and tibias in each surviving animal was also counted.

Results

Figure 33A:
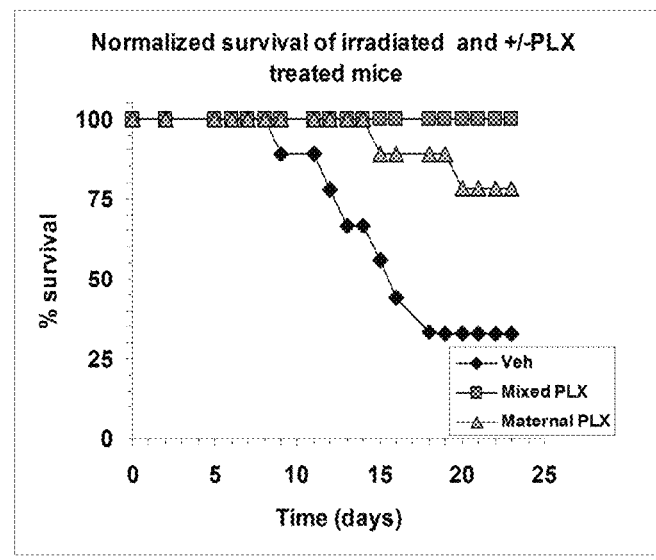
FIGS. 33A-33B present the survival (FIG. 33A) and average weight change (FIG. 33B) following irradiation with a dose of 770cGy. Mice were injected intramuscularly with either maternal derived cells or maternal/fetal mixed cells at a dose of 2×10^6 cells per injection at 24 hours and 5 days following irradiation.
Figure 33B:
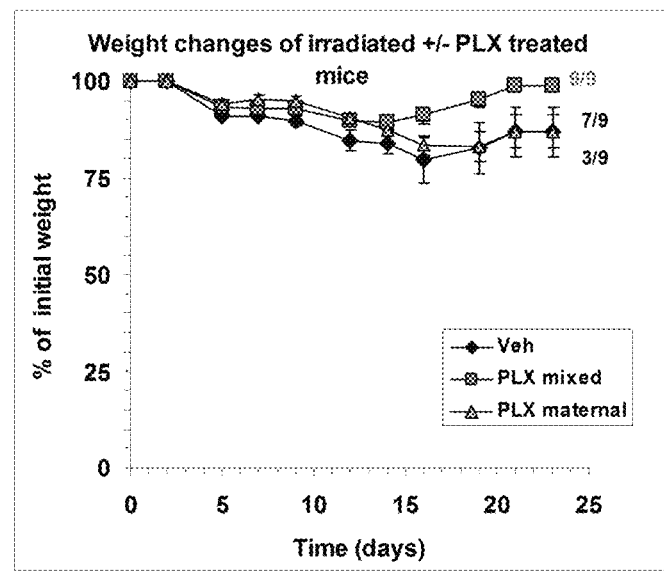

FIGS. 33A-33B present the survival (FIG. 33A) and average weight change (FIG. 33B) following irradiation with a dose of 770cGy. Mixed PLX cells (squares; 9/9 surviving) resulted in better day 23 survival than did maternal PLX (triangles; 7/9 surviving), although both groups had improved survival compared to vehicle treated mice (diamonds; 3/9 surviving). As shown in FIG. 33B, mice treated with mixed PLX cells also retained a higher percentage of their initial weight.

Figure 34A:
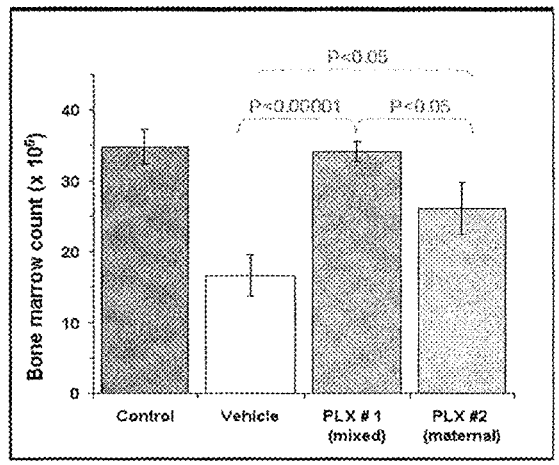
FIGS. 34A-34D illustrate day 23 hematology results.
Figure 34B:
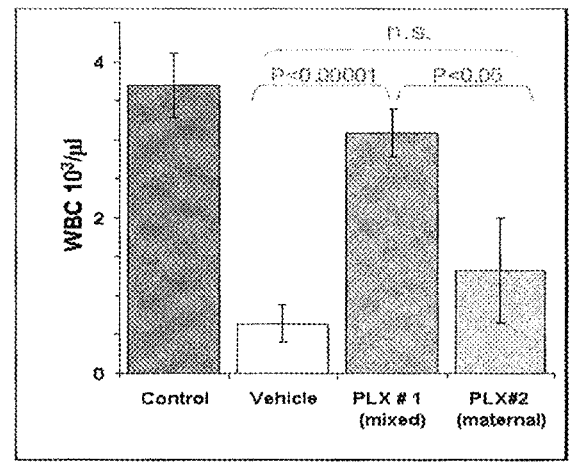
Figure 34C:
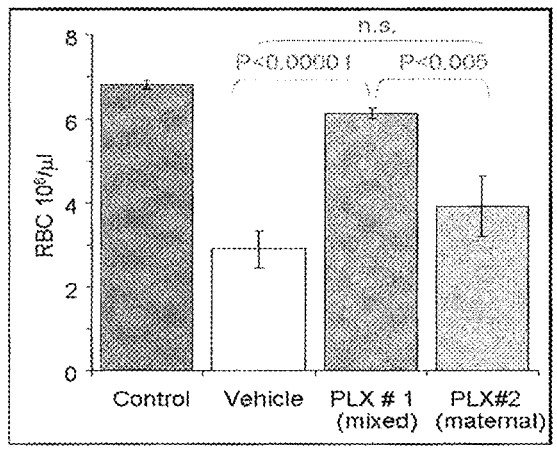
Figure 34D:
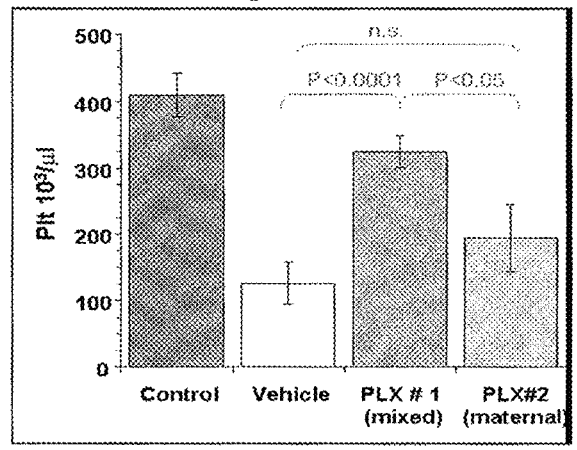
Figure 35A:
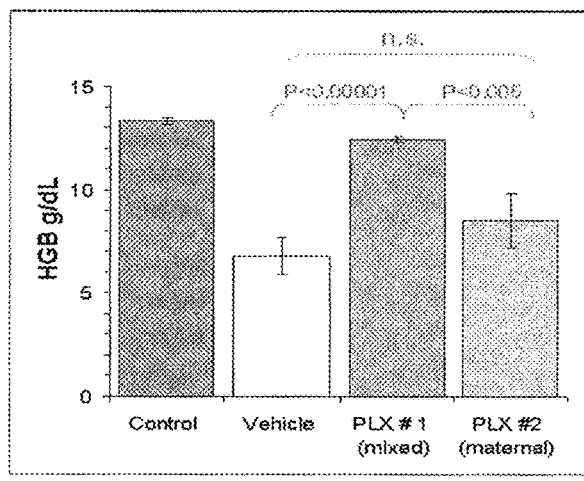
FIGS. 35A-35B present the hemoglobin (FIG. 35A) and hematocrit (FIG. 35B) on day 23.
Figure 35B:
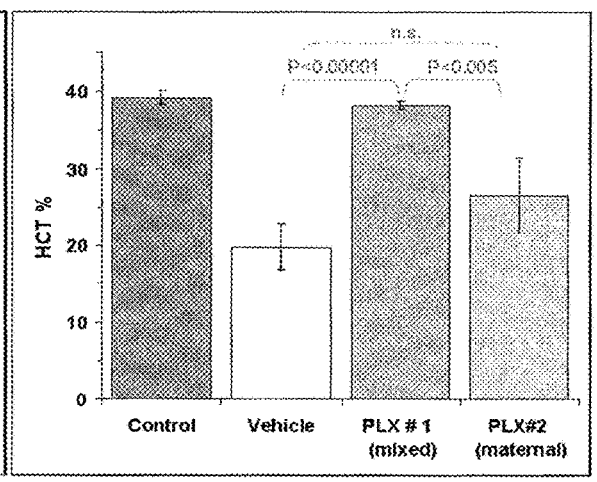

The day 23 hematology results are shown in FIGS. 34A-34D. FIG. 34A presents the total bone marrow counts, FIG. 34B the white blood cell counts, FIG. 34C the red blood cell counts, and FIG. 34D the platelet counts. FIGS. 35A and 35B present the hemoglobin (FIG. 35A) and hematocrit (FIG. 35B) on day 23. For each parameter, the mixed PLX cells resulted in better recovery values compared to either vehicle or maternal PLX-treated mice.

Conclusions

Both maternal and mixed batches of PLX cells administered I.M. improved survival. The mixed PLX batch more efficiently improved survival rate. Mixed PLX also was more efficient in effecting BM repopulation as shown by BM nucleated cell and peripheral blood differential count parameters.

Example 11

The effect of 3D-expanded maternal Adherent Stromal Cells from placenta (PLX) compared to 3D-expanded mixed maternal/fetal Adherent Stromal Cells from placenta on the serum cytokines of irradiated mice were examined following intramuscular administration of 2 million cells/injection of 3D-expanded ASC into C3H mice 24 hours and 5 days post irradiation (770 cGy).

Fifteen C3H males (~27 gram weight, 9 weeks old) were exposed to the dose of 770 cGy of total body typically by 8 MeV X-ray (photon) irradiation. The setup and accurate dose calibration were calculated by the physicists of the Sharett Institute. During the experiments the mice were kept and monitored under SPF conditions.

On day 8, the mice along with one additional control mouse (no cells and no irradiation) were analyzed for CBC using blood from the retro-orbital sinus. Serum was separated and tested using the "Mouse Inflammatory Cytokines Multi-Analyte ELISArray Kit" (SABiosciences; cat # MEM-004A) for the following cytokines/growth factors IL1A, IL1B, IL2, IL4, IL6, IL10, IL12, IL17A, IFNγ, TNFα, G-CSF, and GM-CSF.

Bone marrow from 1 leg (tibia and femur) was harvested for evaluation of bone marrow counts. In addition, the second hind limb femur was sent for decalcification and histopathology.

Results

Figure 36:
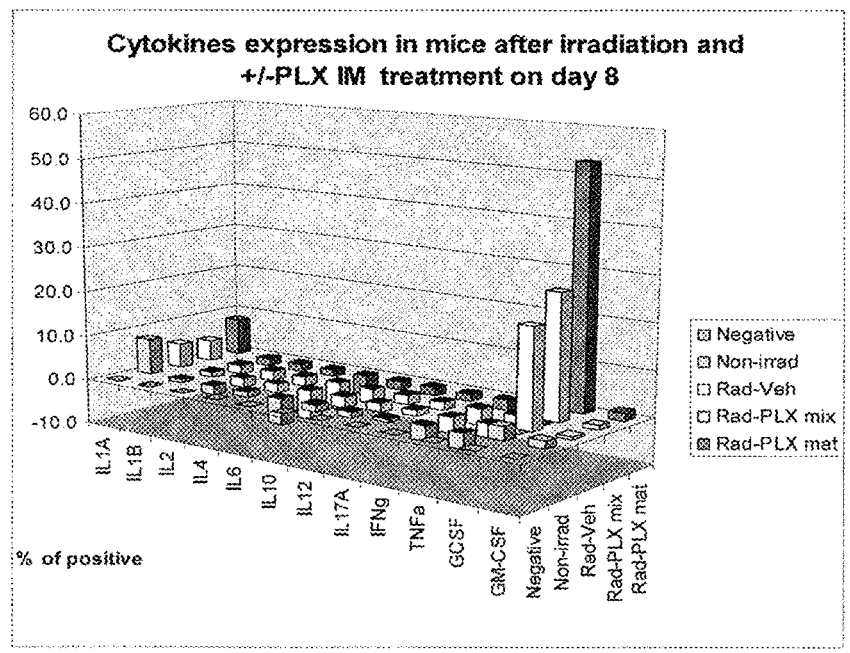
FIG. 36 presents the cytokine profiles on day 8 following injection with PLX cells or vehicle.

FIG. 36 presents the cytokine profiles on day 8 following injection with PLX cells or vehicle. G-CSF levels were increased in all mice treated with irradiation. This increase was greatest in mice treated with maternal PLX cells.

Figure 37A:
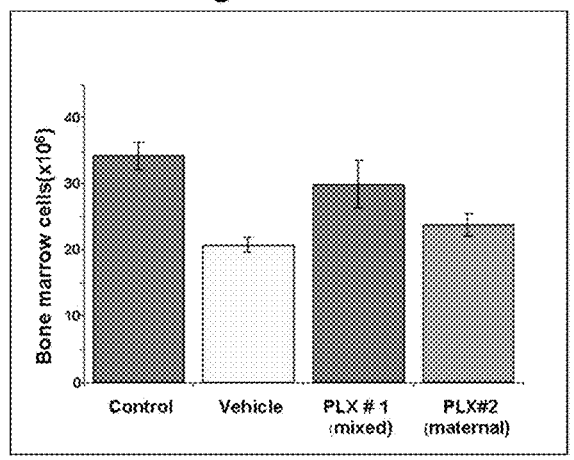
FIGS. 37A-37D illustrate differences among groups of mice in terms of total bone marrow count (FIG. 37A), white blood cell count (FIG. 37B), red blood cell count (FIG. 37C), and platelet counts (FIG. 37D) on day 8.
Figure 37B:
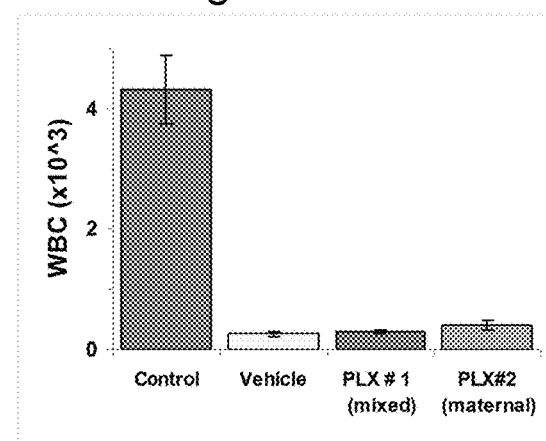
Figure 37C:
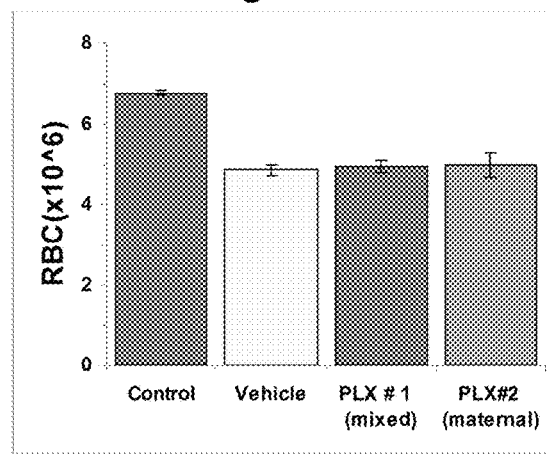
Figure 37D:
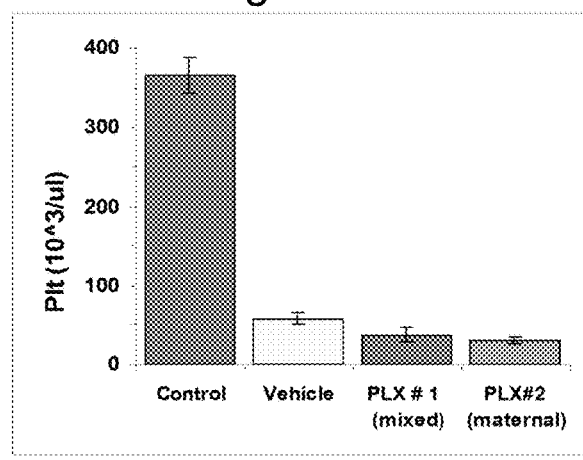

As shown in FIGS. 37A-37D, the differences among the irradiated groups in terms of total bone marrow count (FIG. 37A), white blood cell count (FIG. 37B), red blood cell count (FIG. 37C), and platelet counts (FIG. 37D) were not as apparent on day 8 as on day 23. But mice treated with mixed PLX cells had the highest total bone marrow count (FIG. 37A).

FIGS. 38A-38B similarly show that there was also little difference among the irradiated groups on day 8 with respect to hematocrit (FIG. 38A) or hemoglobin (FIG. 38B).

Histology for the decalcified femur is shown in FIG. 39. The square inset on the left of the low magnification composite pictures is magnified on the right for each sample.

Conclusions

No systemic inflammatory storm was detected in mice ser on day 8 after irradiation. The only notable change was in Granulocyte colony-stimulating factor (G-CSF) levels. G-CSF stimulates the bone marrow to produce granulocytes and stem cells and then stimulates the bone marrow to release them into the blood. G-CSF was elevated in sera of irradiated mice, especially in the maternal-PLX injected group.

Example 12

The effect of 3D-maternal (PLX) cells compared to 3D-mixed (PLX) cells on survival, hematological parameters, and serum cytokines of irradiated mice were examined following intramuscular administration of 2 million cells/injection of 3D expanded ASC into C3H mice 48 hours and 5 days post irradiation (770 cGy).

Thirty-six C3H mice were exposed to total body radiation (770cGy) at Sharett Institute of Oncology at Hadassah Hebrew University Medical Center. The irradiated mice were dividing to 3 groups (12 mice/group) as follows:
1. Injected twice with mixed 2×10$^6$ PLX cells: 48 h and 5 days after irradiation (total number of injected cells—4×10$^6$).
2. Injected twice with maternal 2×10$^6$ PLX cells: 48 h and 5 days after irradiation (total number of injected cells—4×10$^6$).
3. Injected twice with plasmaLyte A: 48 h and 5 days after irradiation.

All injections were performed intramuscularly in 100 microliter PlasmaLyte A/mouse (50 microliter injection to the muscles of each leg as 25 microliters×2 into 2 muscle sites of each leg).

Survival was monitored for 23 days. Animals were inspected daily and weighed 3 times a week. During the experiment the mice were monitored in SPF conditions.

On day 23 the surviving mice, along with 2 additional non-irradiated mice were examined for complete blood chemistry (CBC) using blood from the retro-orbital sinus. Mice were sacrificed and bone marrow harvested. The total number of bone marrow cells in both femurs and tibias in each surviving animal was also counted.

Results

Figure 40A:
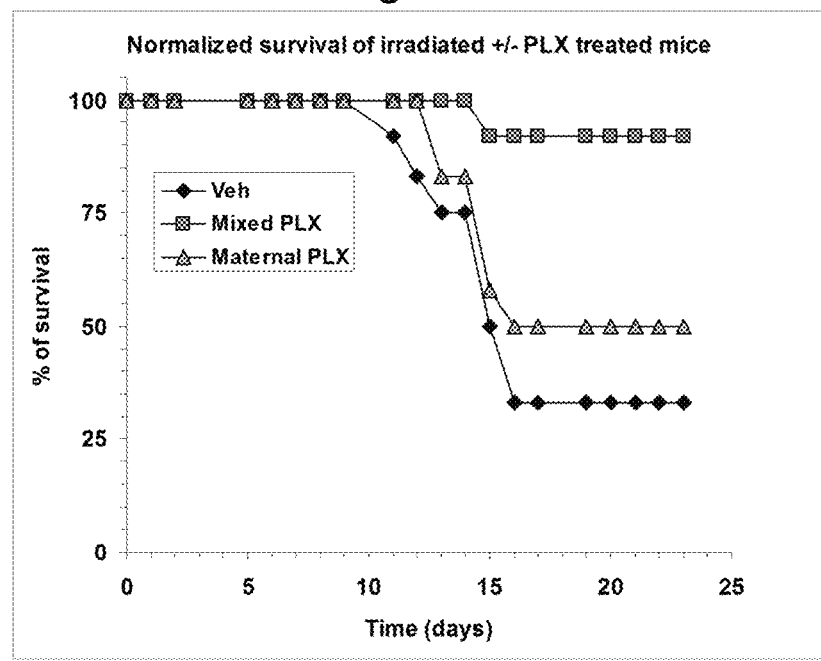
FIG. 40A-40B present the survival (FIG. 40A) and average weight change (FIG. 40B) following irradiation with a dose of 770cGy Mice were injected intramuscularly with either maternal derived cells or maternal/fetal mixed cells at a dose of 2×10^6 cells per injection at 48 hours and 5 days following irradiation.
Figure 40B:
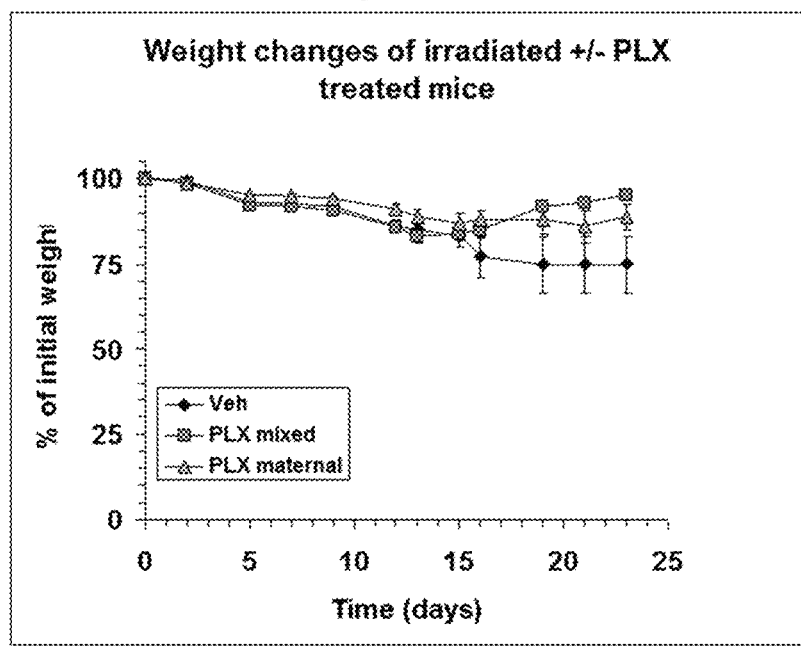

FIGS. 40A-40B present the survival (FIG. 40A) and average weight change (FIG. 40B) following irradiation with a dose of 770cGy and treatment at 48 hours and 5 days following irradiation. As was the case when the first injection was given at 24 hours following irradiation, mixed PLX cells (squares) resulted in better day survival than did maternal PLX (triangles), although both groups again had improved survival compared to vehicle treated mice (diamonds). As shown in FIG. 40B, mice treated with mixed PLX cells also retained a higher percentage of their initial weight compared to the control surviving mice. Compared to treatment at 24 hours and 5 days, delaying the first treatment to 48 hours decreased overall survival slightly, irrespective of the maternal vs mixed nature of the cells.

Figure 41A:
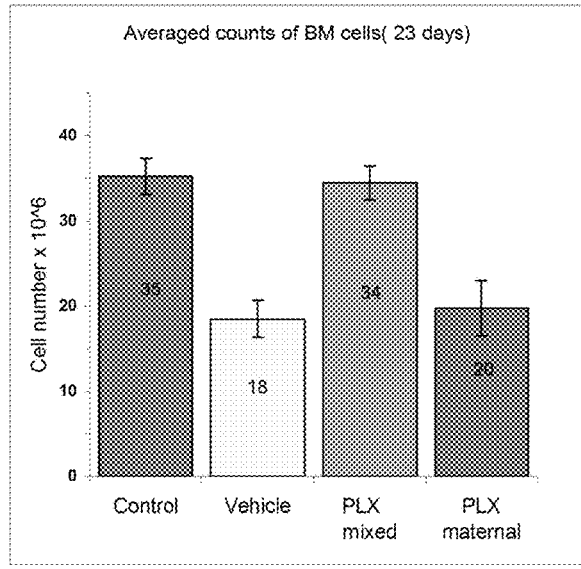
FIGS. 41A-41D illustrate day 23 hematology results in mice treated with maternal or mixed PLX cells at 48 hours and 5 days.
Figure 41B:
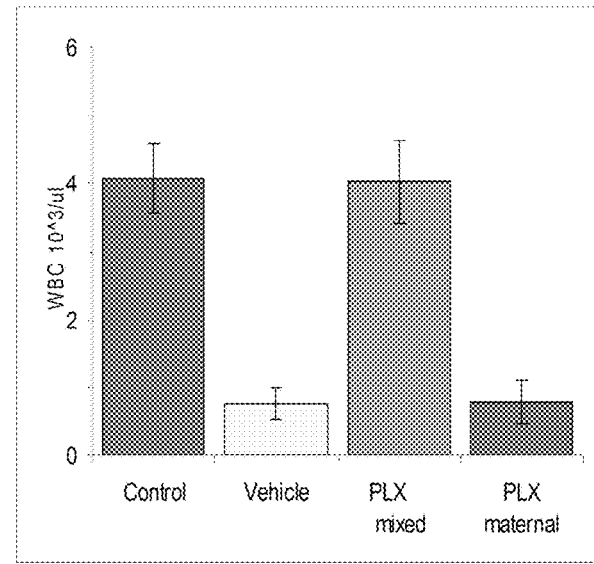
Figure 41C:
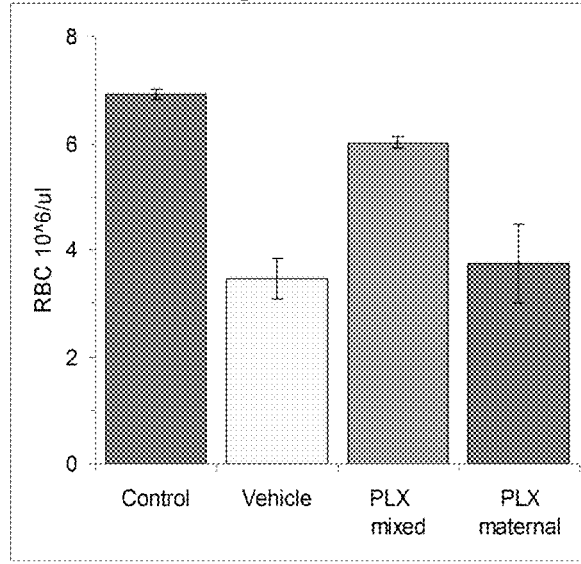
Figure 41D:
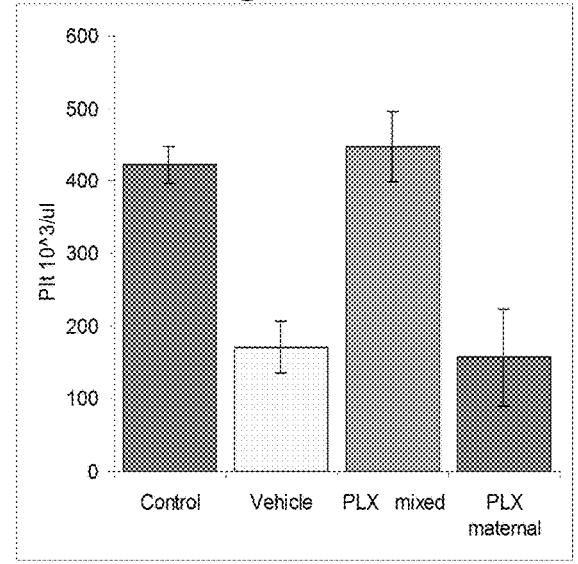

The hematology results for day 23 are shown in FIGS. 41A-41D. FIG. 41A presents the total bone marrow counts, FIG. 41B the white blood cell counts, FIG. 41C the red blood cell counts, and FIG. 41D the platelet counts. FIGS. 42A and 42B present the hemoglobin (FIG. 42A) and hematocrit (FIG. 42B) on day 23. For each parameter, the mixed PLX cells resulted in better recovery values compared to either vehicle or maternal PLX-treated mice.

Conclusions

Even when the first injection was delayed from 24 to 48 hours, both maternal and mixed batches of PLX cells administered I.M. again improved survival. Once again, however, the mixed PLX cells resulted in a better survival rate. Mixed PLX was also once again more efficient in effecting BM repopulation as shown by BM nucleated cell and peripheral blood differential count parameters.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are incorporated in their entirety by reference into the specification, to the same extent as if each individual publication, patent or patent application was specifically and individually indicated to be incorporated herein by reference. In the event the material incorporated by reference conflicts with the disclosure in the specification, the specification herein prevails. In addition, citation or identification of any reference in this application shall not be construed as an admission that such reference is available as prior art to the present invention.

We claim:

1. A method for treating a subject with acute radiation sickness, comprising intramuscularly administering to the subject a pharmaceutical composition comprising three-dimensionally cultured placental-derived adherent stromal cells,
wherein the pharmaceutical composition is administered at a dose sufficient to induce an increase in red blood cell counts or an increase in platelet counts, or both; and
wherein the dose is sufficient to induce an increase in white blood cell counts,
thereby treating the subject.

2. The method of claim 1, wherein exogenous hematopoietic stem cells are not administered to the subject for at least four days following exposure of the subject to radiation.

3. The method of claim 1, wherein the three-dimensionally cultured placental-derived adherent stromal cells are viable following expansion on three-dimensional carriers under conditions supporting cell expansion.

4. The method of claim 3, wherein the three-dimensionally cultured placental-derived adherent stromal cells are viable following detachment from said three-dimensional carriers.

5. The method of claim 4, wherein the three-dimensionally cultured placental-derived adherent stromal cells are viable following cryopreservation.

6. The method of claim 1, wherein the three-dimensionally cultured placental-derived adherent stromal cells exhibit enhanced immunosuppressive activity, relative to placental-derived adherent stromal cells cultured only under two-dimensional culturing conditions.

7. The method of claim 1, wherein the three-dimensionally cultured placental-derived adherent stromal cells exhibit enhanced secretion of Flt-3 ligand, relative to placental-derived adherent stromal cells cultured only under two-dimensional culturing conditions.

8. The method of claim 1, wherein the three-dimensionally cultured placental-derived adherent stromal cells exhibit enhanced secretion of IL-6, relative to placental-derived adherent stromal cells cultured only under two-dimensional culturing conditions.

9. The method of claim 1, wherein the three-dimensionally cultured placental-derived adherent stromal cells exhibit enhanced secretion of stem cell factor (SCF), relative to placental-derived adherent stromal cells cultured only under two-dimensional culturing conditions.

10. The method of claim 1, wherein the three-dimensionally cultured placental-derived adherent stromal cells are viable following culturing on three-dimensional carriers under conditions that support cell expansion without differentiation.

11. The method of claim 1, wherein at least 70% of said three-dimensionally cultured placental-derived adherent stromal cells express CD200.

12. The method of claim 1, wherein said three-dimensionally cultured placental-derived adherent stromal cells are a mixture of maternal-derived placental adherent cells and fetal-derived placental adherent cells.

13. A method for treating a subject with a compromised endogenous hematopoietic system, comprising intramuscularly administering to the subject a pharmaceutical composition comprising three-dimensionally cultured placental-derived adherent stromal cells to induce repopulation of endogenous hematopoietic cells,
wherein the pharmaceutical composition is administered at a dose sufficient to induce an increase in red blood cell counts or an increase in platelet counts, or both; and
wherein the dose is sufficient to induce an increase in white blood cell counts,
thereby treating the subject.

14. The method of claim 13, wherein the subject has been exposed to radiation or chemotherapy, and wherein exogenous hematopoietic stem cells are not administered to the subject for at least four days following the exposure of the subject to radiation or chemotherapy.

15. The method of claim 13, wherein the subject has been exposed to radiation.

16. The method of claim 13, wherein the subject has been exposed to chemotherapy.

17. The method of claim 13, wherein the three-dimensionally cultured placental-derived adherent stromal cells are viable following expansion on three-dimensional carriers under conditions supporting cell expansion.

18. The method of claim 17, wherein the three-dimensionally cultured placental-derived adherent stromal cells are viable following detachment from said three-dimensional carriers.

19. The method of claim 18, wherein the three-dimensionally cultured placental-derived adherent stromal cells are viable following cryopreservation.

20. The method of claim 13, wherein the three-dimensionally cultured placental-derived adherent stromal cells exhibit one or more of the following properties relative to placental-derived adherent stromal cells cultured only under two-dimensional culturing conditions: enhanced immunosuppressive activity, enhanced secretion of Flt-3 ligand, enhanced secretion of IL-6, and enhanced secretion of stem cell factor (SCF).

21. The method of claim 13, wherein the three-dimensionally cultured placental-derived adherent stromal cells are viable following culturing on three-dimensional carriers under conditions that support cell expansion without differentiation.

22. The method of claim 13, wherein at least 70% of said three-dimensionally cultured placental-derived adherent stromal cells express CD200.

23. The method of claim 13, wherein said three-dimensionally cultured placental-derived adherent stromal cells are a mixture of maternal-derived placental adherent cells and fetal-derived placental adherent cells.

24. The method of claim 1, further comprising administering at least one additional therapeutically effective amount of three-dimensionally cultured placental-derived adherent stromal cells together with exogenous hematopoietic stem cells to the subject after a matching period following exposure to radiation.

25. The method of claim 1, wherein the three-dimensionally cultured placental-derived adherent stromal cells are first cultured under two-dimensional culturing conditions and then cultured under three-dimensional culturing conditions.

26. The method of claim 1, wherein exogenous hematopoietic stem cells are administered to the subject after a matching period following exposure to radiation.

27. The method of claim 1, wherein exogenous hematopoietic stem cells are not administered to the subject.

28. The method of claim 1, wherein the pharmaceutical composition is administered at least 2 days following exposure of the subject to radiation.

* * * * *